(12) United States Patent
Saiki et al.

(10) Patent No.: US 9,134,286 B2
(45) Date of Patent: Sep. 15, 2015

(54) ANALYZING DEVICE, ANALYZING APPARATUS USING THE DEVICE, AND ANALYZING METHOD

(75) Inventors: Hiroshi Saiki, Ehime (JP); Kouzou Tagashira, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 265 days.

(21) Appl. No.: 12/740,486

(22) PCT Filed: Oct. 28, 2008

(86) PCT No.: PCT/JP2008/003052
§ 371 (c)(1),
(2), (4) Date: Apr. 29, 2010

(87) PCT Pub. No.: WO2009/057273
PCT Pub. Date: May 7, 2009

(65) Prior Publication Data
US 2010/0255589 A1    Oct. 7, 2010

(30) Foreign Application Priority Data

| Oct. 30, 2007 | (JP) | 2007-281056 |
|---|---|---|
| Feb. 6, 2008 | (JP) | 2008-025809 |
| Feb. 6, 2008 | (JP) | 2008-025810 |
| Mar. 24, 2008 | (JP) | 2008-074785 |
| Apr. 10, 2008 | (JP) | 2008-101995 |
| Aug. 28, 2008 | (JP) | 2008-218887 |
| Sep. 16, 2008 | (JP) | 2008-235828 |
| Oct. 16, 2008 | (JP) | 2008-266931 |

(51) Int. Cl.
*G01N 21/07* (2006.01)
*G01N 33/02* (2006.01)
*G01N 35/00* (2006.01)
*B01L 3/00* (2006.01)
*G01N 35/04* (2006.01)

(52) U.S. Cl.
CPC ............ *G01N 33/02* (2013.01); *B01L 3/50273* (2013.01); *B01L 3/502738* (2013.01);
(Continued)

(58) Field of Classification Search
CPC .............................................. Y10T 436/111666
USPC .......................................................... 422/72
See application file for complete search history.

(56) References Cited

U.S. PATENT DOCUMENTS

| 5,061,381 A | * | 10/1991 | Burd | 210/789 |
|---|---|---|---|---|
| 5,242,606 A | * | 9/1993 | Braynin et al. | 210/787 |

(Continued)

FOREIGN PATENT DOCUMENTS

| CN | 1439058 | 8/2003 |
|---|---|---|
| CN | 1535377 | 10/2004 |

(Continued)

OTHER PUBLICATIONS

Software translation of Saeki H. et al., JP-2007-078676-A; Mar. 29, 2007.*

(Continued)

*Primary Examiner* — Yelena G Gakh
*Assistant Examiner* — Michelle Adams
(74) *Attorney, Agent, or Firm* — Hamre, Schumann, Mueller & Larson, P.C.

(57) ABSTRACT

An analyzing device including a capillary cavity and an inlet protruding circumferentially outward from an axial center. The capillary cavity and the inlet are connected by a guide section formed so as to extend circumferentially inward and on which a capillary force acts. A sample liquid collected from a leading end of the inlet is transferred to a separation cavity. A bent section and a recess are formed at a connected section of the guide section and the capillary cavity so as to change the direction of a passage.

8 Claims, 89 Drawing Sheets

(52) U.S. Cl.
CPC .......... *G01N21/07* (2013.01); *G01N 35/00029* (2013.01); *B01L 2200/0605* (2013.01); *B01L 2300/0803* (2013.01); *B01L 2300/0883* (2013.01); *B01L 2400/0406* (2013.01); *B01L 2400/0409* (2013.01); *G01N 2035/00237* (2013.01); *G01N 2035/0449* (2013.01); *Y10T 436/111666* (2015.01)

(56) References Cited

U.S. PATENT DOCUMENTS

| | | | |
|---|---|---|---|
| 5,286,454 | A * | 2/1994 | Nilsson et al. ............... 422/548 |
| 6,315,738 | B1 | 11/2001 | Nishikawa et al. |
| 6,830,669 | B2 | 12/2004 | Miyazaki et al. |
| 7,485,118 | B2 | 2/2009 | Blankenstein et al. |
| 7,582,259 | B2 | 9/2009 | Ogawa et al. |
| 7,736,907 | B2 | 6/2010 | Blankenstein et al. |
| 8,158,079 | B2 | 4/2012 | Sugimoto et al. |
| 2003/0114785 | A1 * | 6/2003 | Kikuchi et al. ............... 604/6.09 |
| 2004/0043477 | A1 | 3/2004 | Schibli |
| 2004/0120856 | A1 | 6/2004 | Andersson et al. |
| 2004/0197233 | A1 | 10/2004 | Nagaoka et al. |
| 2006/0078873 | A1 | 4/2006 | Ogawa et al. |
| 2009/0123338 | A1 | 5/2009 | Guan et al. |
| 2009/0205447 | A1 * | 8/2009 | Sugimoto et al. .......... 73/864.21 |
| 2011/0060203 | A1 | 3/2011 | Katsuki et al. |
| 2011/0256572 | A1 | 10/2011 | Amano et al. |

FOREIGN PATENT DOCUMENTS

| | | |
|---|---|---|
| CN | 1542454 | 11/2004 |
| CN | 1551802 | 12/2004 |
| CN | 1624448 | 6/2005 |
| CN | 1695808 | 11/2005 |
| CN | 1708691 | 12/2005 |
| CN | 1715932 | 1/2006 |
| CN | 1751239 | 3/2006 |
| CN | 1890566 | 1/2007 |
| CN | 1930480 | 3/2007 |
| CN | 1987480 | 6/2007 |
| CN | 1993611 | 7/2007 |
| EP | 1424040 | 6/2004 |
| JP | 4-504758 | 8/1992 |
| JP | 7-500910 | 1/1995 |
| JP | 2001-159618 | 6/2001 |
| JP | 2004-239743 | 8/2004 |
| JP | 2005-114438 | 4/2005 |
| JP | 2006-343206 | 12/2006 |
| JP | 2007-078676 | 3/2007 |
| JP | 2007-268486 | 10/2007 |
| JP | 2008-032695 | 2/2008 |
| WO | 90/13016 | 11/1990 |
| WO | 93/08893 | 5/1993 |
| WO | WO 00/66995 | 11/2000 |
| WO | WO 02/074438 | 9/2002 |
| WO | WO 03/020424 | 3/2003 |
| WO | 2004/074846 | 9/2004 |
| WO | WO-2008/001796 A1 * | 1/2008 |

OTHER PUBLICATIONS

International Search Report of PCT/JP2008/003052, dated Jan. 27, 2009.

Partial Supplementary European Search Report, May 8, 2015; European Patent Application No. 08845691 (7 pages).

* cited by examiner

FIG. 12
(a)
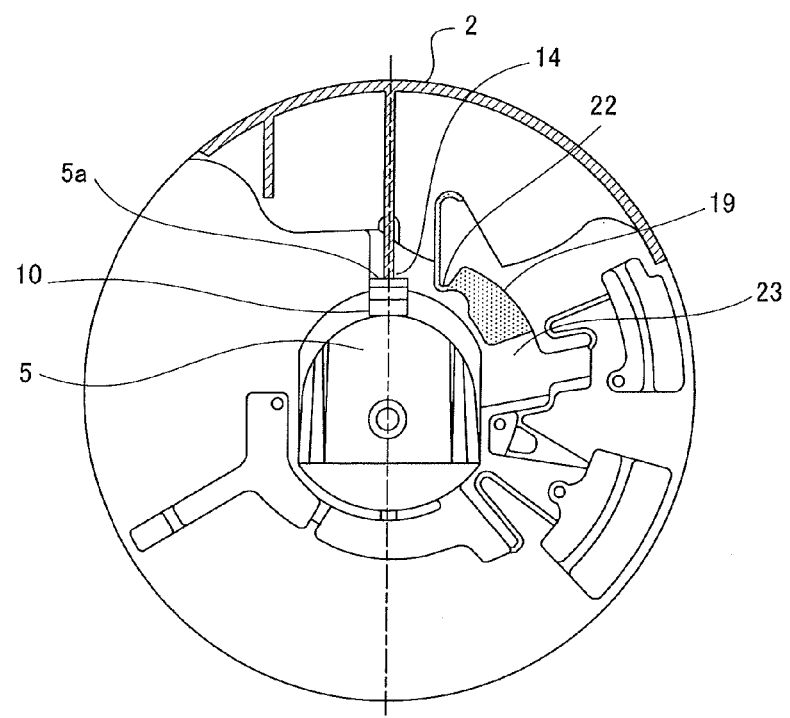
(b)
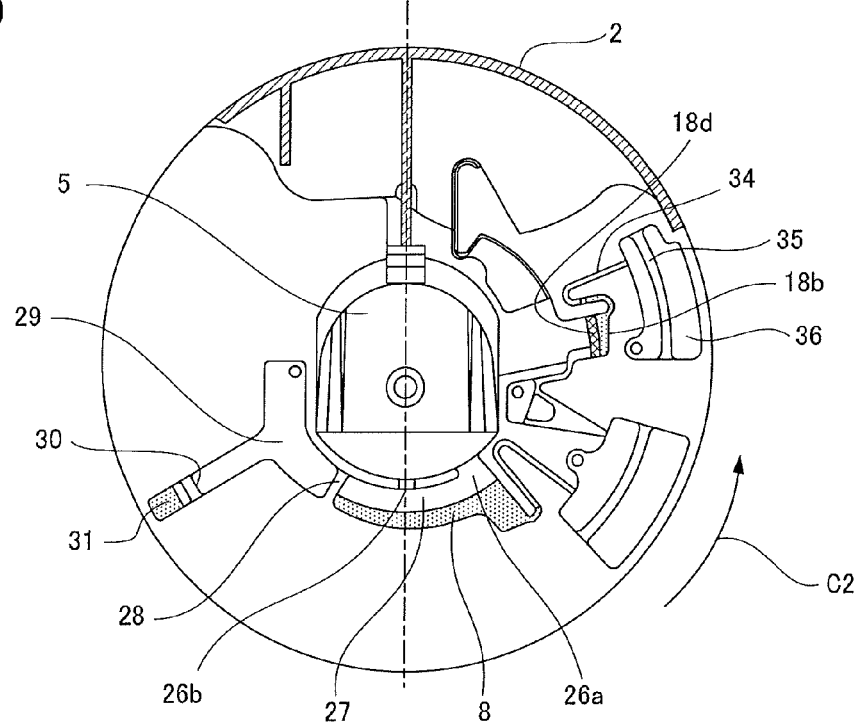

FIG. 14
(a)
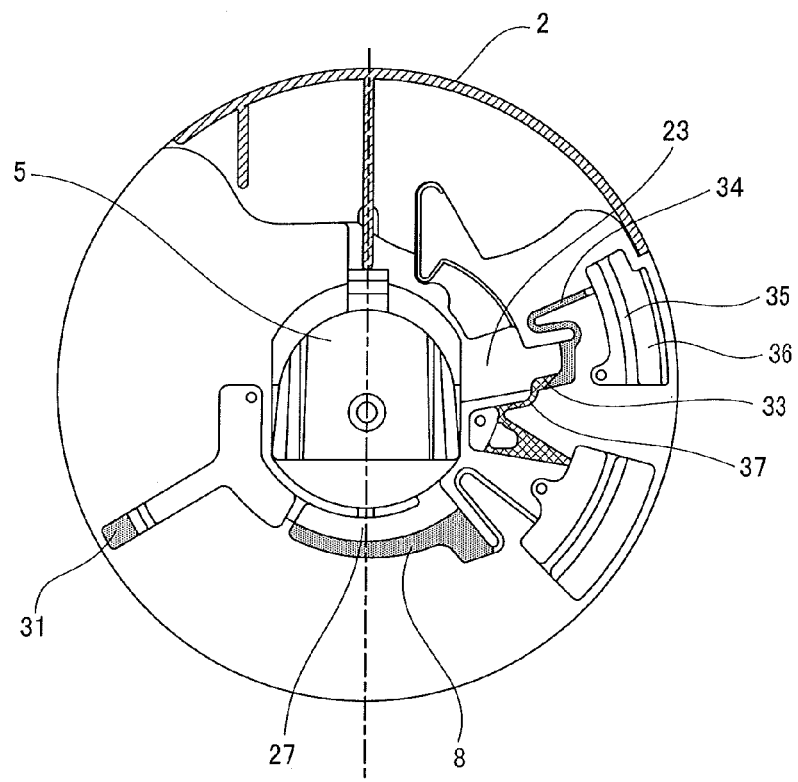
(b)
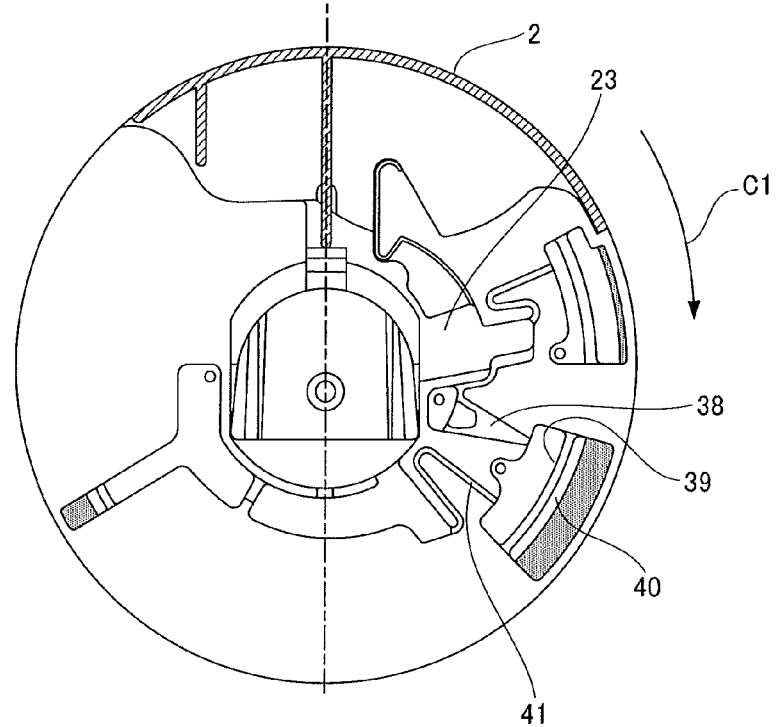

FIG. 17
(a)
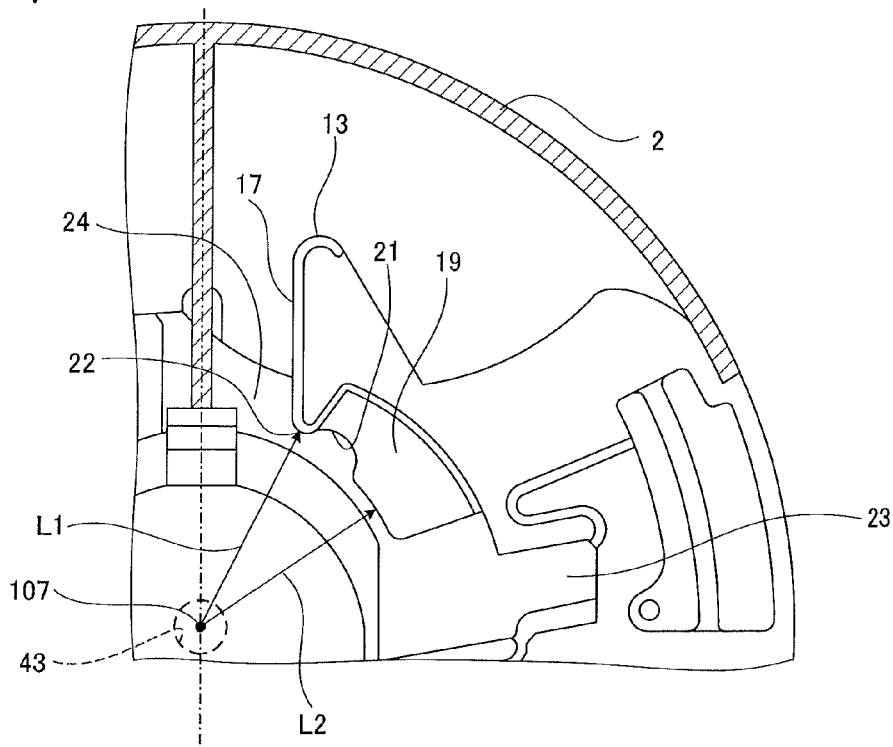
(b)
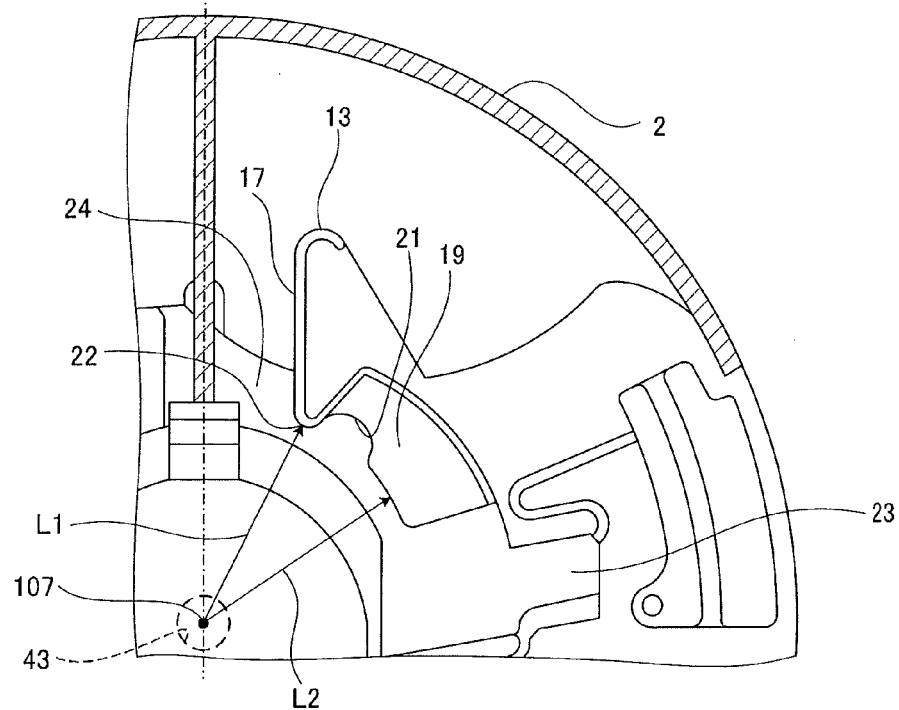

FIG. 40
(a)
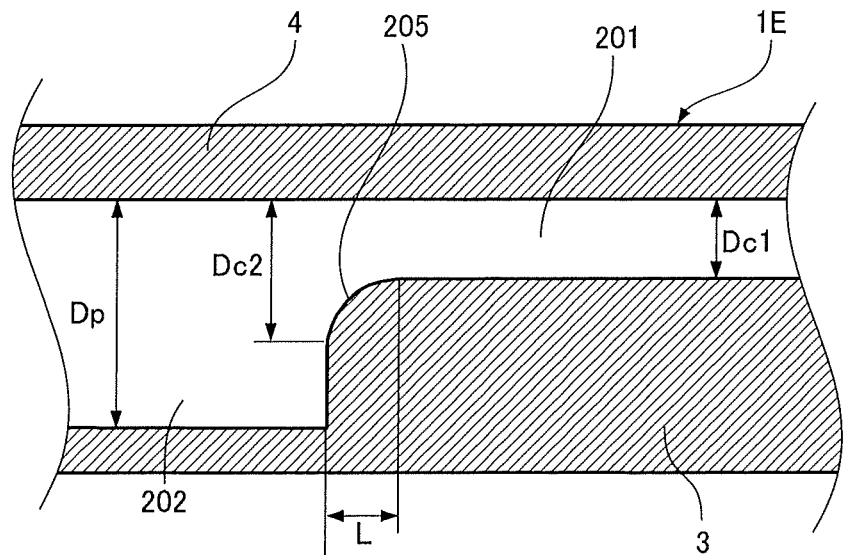
(b)
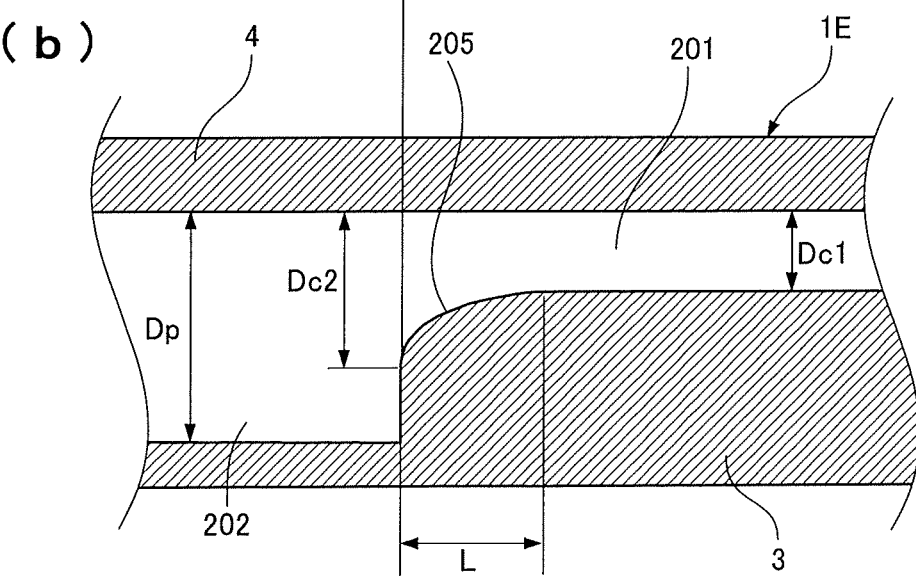

FIG. 60
(a) 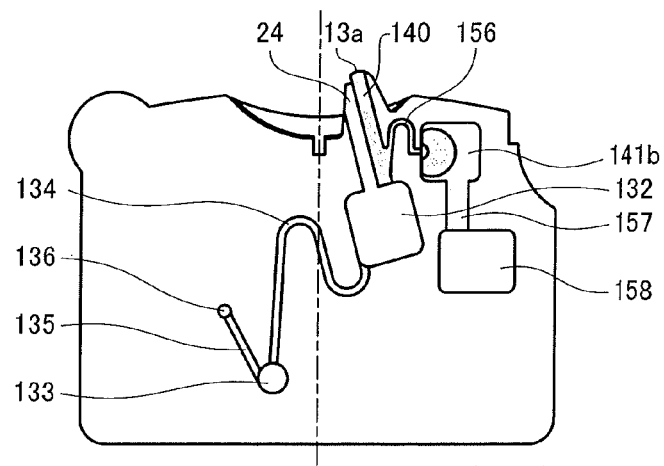
(b) 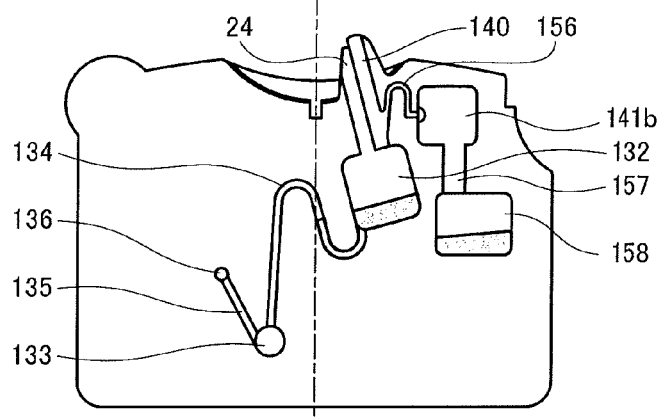
(c) 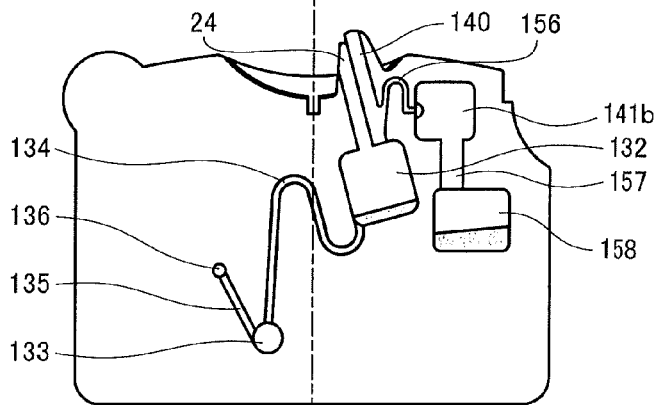
(d) 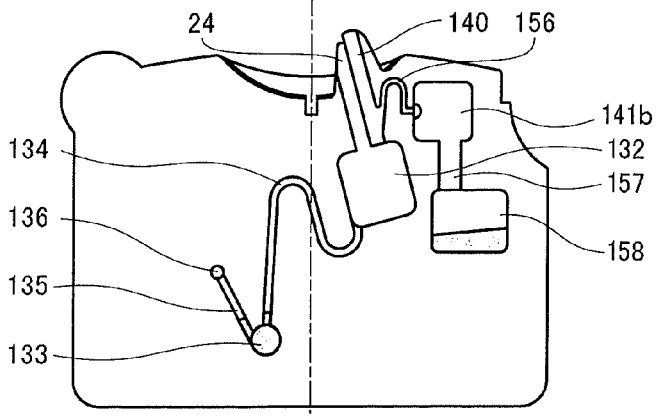

(a)

(b)

ANALYZING DEVICE, ANALYZING APPARATUS USING THE DEVICE, AND ANALYZING METHOD

TECHNICAL FIELD

The present invention relates to an analyzing device to be used to analyze a liquid collected from a living organism or the like, and to an analyzing apparatus and an analyzing method using the same. More specifically, the present invention relates to a technique of causing an analyzing device to directly collect a sample liquid.

BACKGROUND ART

Conventionally, as a method of analyzing a liquid collected from a living organism or the like, an analyzing method is known that uses an analyzing device in which a liquid channel is formed. The analyzing device is capable of controlling a fluid using a rotating apparatus. Since the analyzing device is capable of performing dilution of a sample liquid, solution measurement, separation of solid components, transfer and distribution of a separated fluid, mixing of a solution and a reagent, and the like by utilizing centrifugal force, various biochemical analyses can be carried out.

An analyzing device 50 described in Patent Document 1 which transfers a solution using centrifugal force is arranged as illustrated in FIG. 107 such that after injecting a sample liquid into a measuring chamber 52 from an inlet 51 with an insertion tool such as a pipette and holding the sample liquid by a capillary force of the measuring chamber 52, the sample liquid is transferred to a separating chamber 53 by a rotation of the analyzing device. By providing such an analyzing device which uses a centrifugal force as a power source for liquid transfer with a disk-like shape, microchannels for performing liquid transfer control can be arranged radially. Since no wasted area is created, the disk-like shape is used as a favorable shape.

In addition, as illustrated in FIG. 108A, an analyzing device 54 described in Patent Document 2 is arranged so as to collect a sample liquid by a capillary action from an inlet 55 to fill a first cavity 56 and transfer the sample liquid in the first cavity 56 to a separation cavity 58 by a rotation of the analyzing device 54 around an axial center 57. Since a sample liquid can be directly collected from the inlet 55, there is an advantage that the sample liquid can be injected into the analyzing device by a simple operation that does not require an insertion tool such as a pipette.

Conventionally, analyzing apparatuses which use an analyzing device that internally collects a sample liquid and which analyze characteristics of the sample liquid while rotating the analyzing device around the axial center of the same have been put to practical use.

In recent years, there has been an increase in market demands for reductions in sample liquid volume, downsizing of apparatuses, short-time measurement, simultaneous multiple measurement, and the like. An analyzing apparatus with higher accuracy is desired which is capable of causing a reaction between a sample liquid such as blood and various analytical reagents, detecting a mixture of the sample liquid and the reagent, and testing stages of progression of various diseases within a short period of time.

FIG. 109 illustrates an analyzing device according to Patent Document 3 which includes a capillary measurement segment and a hydrophilic stopper.

The analyzing device is made up of air ducts V1, V2, V3, and V4 which communicate with the atmosphere, sample reservoirs R1, R2, and R3, a measurement segment L formed by a capillary, and a hydrophilic stopper S1.

The measurement segment L ensures that an accurate amount of a liquid sample is to be measured and distributed for the purpose of improving analytical precision. A liquid sample injected into the sample reservoir R1 flows into the measurement segment L from the sample reservoir R1 by a capillary force and fills the U-shaped measurement segment L.

Both ends of the measurement segment L communicate with the atmosphere via the air ducts V1 and V2. The sample liquid is moved by a capillary force to the hydrophilic stopper S1, but stops at a connected section of the measurement segment L and the hydrophilic stopper S1.

This is because a configuration in which the width of the hydrophilic stopper S1 is broader than the width of the measurement segment L prevents the liquid sample from coming into contact with a wall face of the hydrophilic stopper S1 and consequently halting the capillary force.

When the analyzing device is set on a rotary platform and is rotated at sufficient speed to overcome the resistance of the hydrophilic stopper S1, the liquid contained in the measurement segment L passes the stopper S1 and enters the sample reservoir R2 by a centrifugal force and a capillary force. When the sample liquid passes the hydrophilic stopper S1 due to a centrifugal force, air enters from the air ducts V1 and V2, consequently determining a length of a liquid column of the measurement segment L and, in turn, a sample amount to be sent to the sample reservoir R2.

A further sample reservoir R3 is provided underneath the sample reservoir R2, which can be used to cause a reaction with the sample liquid or to prepare the sample liquid for subsequent analysis. A liquid injected in the sample reservoir R2 is transported from the sample reservoir R2 to the sample reservoir R3 by a centrifugal force.

Conventionally, there are methods of electrochemically or optically analyzing a biological fluid using an analyzing device in which a microchannel is formed. Methods of electrochemical analysis include, as a biosensor that analyzes a specific component in a sample liquid, determining a blood glucose level or the like by measuring a current value obtained by a reaction between blood glucose and a reagent such as glucose oxidase held in a sensor.

In addition, with an analyzing method using an analyzing device, fluid control can be realized using a rotating apparatus having a horizontal axis, and sample liquid measurement, separation of cytoplasmic material, transfer and distribution of separated fluids, mixing/agitation of liquids and the like can be performed utilizing a centrifugal force. Therefore, various biochemical analyses can be carried out.

Conventional methods of collecting a sample liquid for introducing a sample into an analyzing device include an electrochemical biosensor illustrated in FIG. 110.

The electrochemical biosensor is formed by bonding an insulated substrate 225 to a cover 226 with a spacer 227 and a reagent layer 228 sandwiched in-between. A sample liquid is introduced into a cavity 230 by a capillary action through a suction port 229 on the cover 226. The sample liquid is guided to the positions of an action pole 231 and an antipole 232 on the insulated substrate 225 and the reagent layer 228. Reference numeral 233 denotes an air relief hole.

In this case, a quantitative collection of the sample is performed by a cubic capacity of the cavity 230. The current value created by a reaction between the sample liquid and the reagent at the action pole 231 and the antipole 232 is connected to and read by an external measurement apparatus, not shown, via leads 234 and 235 (for example, refer to Patent Document 4).

Furthermore, with a centrifugal transfer biosensor illustrated in FIG. 108B, a sample liquid is quantitatively collected into a first capillary cavity 312 by a capillary action from an inlet port 313. By subsequently causing a centrifugal force to act, the sample liquid in the capillary cavity 312 is transferred to a receiving cavity 317 via a filtering material 315, a first channel 314, a second cavity 316, and a core 318. The sample liquid involved in a reaction with a reagent in the receiving cavity 317 is centrifugally separated. Only a solution component is collected by a capillary force into the second cavity 316 and a reaction state is optically read (for example, refer to Patent Document 2).

Moreover, with a centrifugal transfer biosensor 400 illustrated in FIG. 111, a sample is transferred from an inlet port 409 to an outlet port 410 by a capillary force through a serpentine continuous microconduit 411. After filling respective capillary cavities 404a to 404f with the sample liquid, the sample liquid in the respective capillary cavities are distributed at positions of respective ventilation holes 406a to 406g by a centrifugal force generated by a rotation of the biosensor. The sample liquid is then transferred to a next processing chamber (not shown) through respective coupling microconduits 407a to 407f (for example, refer to Patent Document 5). Reference characters 408a to 408f denote valve function sections.

Patent Document 1: National Publication of International Patent Application No. 1995-500910
Patent Document 2: National Publication of International Patent Application No. 1992-504758
Patent Document 3: National Publication of International Patent Application No. 2005-518531
Patent Document 4: Japanese Patent Laid-Open No. 2001-159618
Patent Document 5: National Publication of International Patent Application No. 2004-529333

DISCLOSURE OF THE INVENTION

Problems to be Solved by the Invention

However, with Patent Document 1, since a sample liquid cannot be directly collected, work efficiency when supplying a sample liquid is problematically low. In addition, with Patent Document 2, while a sample liquid can be directly collected, the lack of an axial center in the analyzing device results in a large turning radius, which problematically causes an increase in the size of an analyzing apparatus and to a greater load on the apparatus.

The present invention overcomes such conventional problems, and an object of the present invention is to provide an analyzing device capable of directly collecting and internally supplying a sample liquid and an analyzing apparatus that can be downsized compared to what is conventional.

Furthermore, with Patent Document 3, since a sample liquid does not come to a complete stop at a connected section of the measurement segment L and the hydrophilic stopper S1 when the sample liquid moves across a hydrophilic face of the measurement segment L, a portion of the sample liquid problematically overflows into the hydrophilic stopper S1 and an accurate measurement cannot be made by the measurement segment L.

The present invention overcomes the conventional problem described above and an object of the present invention is to provide an analyzing device capable of accurately stopping a flow of a liquid by a capillary force.

However, with such conventional configurations, since a leading end of a spot application section is rectangular, a sample liquid problematically adheres during spot application to external wall faces of the analyzing device other than the spot application section.

The present invention overcomes the conventional problem described above and an object of the present invention is to provide an analyzing device capable of having a sample liquid adhere to only a spot application section.

Moreover, with the analyzing devices according to Patent Document 2 and Patent Document 5, when injecting a sample from a sample injection tool such as a syringe, a dropper, or a pipette, it is required that a leading end of the sample injection tool is brought into contact with a sample inlet of the analyzing device, and the sample must be suctioned by a capillary force by spot-applying small amounts of the sample a number of times which can be held at the outside of the inlet by surface tension. Alternatively, a sample must be dropped from a sample injection tool onto a sheet-like test specimen made of plastic or glass and suctioned by bringing a sample inlet of the analyzing device into contact with the dropped sample. As a result, work to be performed by a user ends up becoming very cumbersome and complicated. In particular, forms of injection using a sample injection tool are frequently seen at hospitals, clinical testing firms, and research institutions, and are in high demand from users.

The present invention overcomes the conventional problem described above and an object of the present invention is to provide an analyzing device capable of suctioning a sample injected from a sample injection tool from an inlet without causing leakage, quantifying the sample by a rotational movement, and collecting a sample from the sample injection tool in addition to performing methods using conventional puncture tools.

When classifying analyzing devices according to methods of introducing a sample liquid, in addition to a type in which an appropriate amount is injected by a syringe such as seen in Patent Document 1, a type is conceivable in which an opening 240 of a capillary channel is brought into contact with a drop of sample liquid to suction the sample liquid with a capillary force as illustrated in FIG. 75.

With an analyzing device 1 illustrated in FIG. 75, the opening 240 is provided on a spot application section 13A formed so as to protrude from an analyzing device main body 241. As illustrated in FIG. 76, the analyzing device 1 is constructed by bonding together a base substrate 3 and a cover substrate 4.

An internal recess to become a holding chamber 19a, a reagent chamber 132a, a channel 134, a measurement chamber 133, and a channel 135 is formed on a bonding face 3a of the base substrate 3 with the cover substrate 4. The reagent chamber 132a holds an analytical reagent (not shown). The cover substrate 4 covers respective opening faces of the internal recess so as to form cavities having predetermined gaps to enable respective functions such as transferring of a sample liquid by a capillary force and retention of a predetermined amount of liquid. Reference character 136b denotes an air open hole formed on the cover substrate 4 in correspondence to a position of an outlet port 136a on a side of the base substrate 3.

The spot application section 13A is formed by a bonding of a protrusion 242 of the base substrate 3 and a protrusion 243 of the cover substrate 4. A protrusion length L3 of the protrusion 242 from the analyzing device main body 241 is formed so as to equal a protrusion length L4 of the protrusion 243 from the analyzing device main body 241. A supplying capillary channel 17a formed between the base substrate 3 and the cover substrate 4 as illustrated in FIGS. 77 and 78 connects a leading end of the spot application section 13A and the holding chamber 19a.

When performing an analysis of blood as a sample liquid, as illustrated in FIG. 79, by setting the analyzing device 1 to a vertical posture and bringing the spot application section 13A into contact with a blood drop 121 on a fingertip 120 of a testee, blood as a sample is suctioned up to the holding chamber 19a by capillary forces of the supplying capillary channel 17a and the holding chamber 19a.

However, the speed of suctioned blood is affected by the postures of the supplying capillary channel 17a and the holding chamber 19a. When a period of time in which the spot application section 13A is brought into contact with the blood drop 121 is short or when postures are inappropriate, problematically, a fixed amount of blood necessary to carry out an accurate analysis cannot be quantitatively sampled.

An object of the present invention is to provide an analyzing device that is brought into contact with a drop of sample liquid to suction the sample liquid by a capillary force and which is capable of reducing a period of time necessary to suction a fixed amount of the sample liquid.

When performing an analysis of blood as a sample liquid, as also illustrated in FIG. 79, by setting the analyzing device 1 to a vertical posture as illustrated in FIG. 105 and bringing the spot application section 13A into contact with a blood drop 121 on a fingertip 120 of a testee, blood as a sample is suctioned up to the holding chamber 19a by capillary forces of the supplying capillary channel 17a and the holding chamber 19a. FIG. 106 is an enlarged view of the holding chamber 19a, the reagent chamber 132a, and the supplying capillary channel 17a formed on the bonding face 3a of the base substrate 3.

However, the speed of suctioned blood is affected by the postures of the supplying capillary channel 17a and the holding chamber 19a. When a period of time in which the spot application section 13A is brought into contact with the blood drop 121 is short or when postures are inappropriate, problematically, a fixed amount of blood necessary to carry out an accurate analysis cannot be quantitatively sampled.

An object of the present invention is to provide an analyzing device that is brought into contact with a drop of sample liquid to suction the sample liquid by a capillary force and which has a structure that enables readily visual confirmation of the completion of suction of a fixed amount of the sample liquid.

Means for Solving the Problems

An analyzing device according to the present invention is an analyzing device having a microchannel structure that is rotationally driven around an internally set axial center and transfers a sample liquid towards an internal measurement spot by a centrifugal force accompanying the rotational drive, and which is used for reading involving accessing a reactant at the measurement spot, the analyzing device including: an inlet protruding circumferentially outward from the axial center and which collects the sample liquid from a leading end of the inlet; a guide section formed so as to extend circumferentially inward from the inlet and in which a capillary force acts; a capillary cavity as a sample measuring section that quantitatively measures, by a capillary force, a fixed amount of the sample liquid collected from the inlet via the guide section; and a receiving cavity that accepts the sample liquid transferred from the capillary cavity, wherein a bent section forming a recess and which changes the direction of a passage is formed at a connected section of the guide section and the capillary cavity. Preferably, a protective cap that holds sample liquid scattered from the guide section is provided outside the inlet. In addition, a cavity opened to air is formed beside a base section of the guide section, the bent section, and the capillary cavity. Furthermore, the bent section is formed on a same circumference as the capillary cavity or formed circumferentially inward of the capillary cavity with respect to the axial center.

An analyzing apparatus according to the present invention includes: a rotation driving unit that rotates the analyzing device around an axial center; and an analysis unit that accesses and analyzes a reactant inside the analyzing device based on a solution transferred by the rotation driving unit, wherein a sample liquid in the capillary cavity can be transferred to the receiving cavity by a rotation of the rotation driving unit.

An analyzing method according to the present invention includes: rotating the analyzing device around the axial center set inside the analyzing device, breaking a sample liquid spot-applied to an inlet of the analyzing device at the bent section, and transferring only the sample liquid held in the capillary cavity to the receiving cavity; mixing at least a portion of the transferred sample liquid with a reagent; and accessing a reactant at the measurement spot at a timing where the measurement spot exists at a reading position.

An analyzing device according to the present invention is an analyzing device having a microchannel structure that is rotationally driven around an internally set axial center and transfers a sample liquid towards an internal measurement spot by a centrifugal force accompanying the rotational drive and which is used for reading involving accessing a reactant at the measurement spot, wherein a sample liquid spot-applied to an inlet protruding circumferentially outward from the axial center is connected to the measurement spot via a guide section formed so as to extend circumferentially inward from the inlet and in which a capillary force acts, and a liquid reservoir that temporarily holds the sample liquid before being suctioned into the guide section is formed at a leading end of the guide section.

An analyzing device according to the present invention is an analyzing device that suctions a sample liquid spot-applied to an inlet by a capillary force of a measurement spot and which is used for reading involving accessing a test object at the measurement spot, wherein a liquid reservoir that temporarily holds the sample liquid before suction is formed at a connected section of the inlet and the measurement spot.

An analyzing device according to the present invention is an analyzing device including a microchannel having: a sample measuring section made up of a capillary channel and which quantitatively measures a fixed amount of a sample liquid to be analyzed; and a receiving section connected to the sample measuring section and which accepts the fixed amount of sample liquid measured by the sample measuring section and causes a reaction between the sample liquid and a reagent, wherein a partition wall that splits a channel in a width direction is formed in a capillary channel at a connected section of the sample measuring section and the receiving section. Preferably, the partition wall is formed high towards the receiving section.

An analyzing device according to the present invention is an analyzing device including a microchannel having: a sample measuring section made up of a capillary channel and which quantitatively measures a fixed amount of a sample liquid to be analyzed; and a receiving section connected to the sample measuring section and which accepts the fixed amount of sample liquid measured by the sample measuring section and causes a reaction between the sample liquid and a reagent, wherein an inclined face is formed so that a capillary channel at a connected section of the sample measuring section and the receiving section widens towards the receiving section. Preferably, regarding heights of the sample measuring section and the receiving section at a connected plane of the sample measuring section and the receiving section, the height of the receiving section is greater than the height of the sample measuring section.

An analyzing device according to the present invention, wherein a cover substrate is superimposed on a base substrate on which a groove to become a channel is formed and a capillary cavity is formed inside, a spot application section is provided whose proximal end is connected to the capillary cavity and whose leading end protrudes from the cover substrate, and the leading end of the spot application section is formed in a hemispherical shape protruding in a direction that separates from a channel forming face of the base substrate. Preferably, a wall face of the capillary cavity has, been subjected to hydrophilic treatment. In addition, a rib is provided that is lower than the spot application section and which surrounds the spot application section with a gap in between.

An analyzing device according to the present invention includes: a first inlet for collecting a sample liquid, a first capillary cavity connected to the first inlet and which is capable of collecting a sample liquid by a capillary force via the first inlet, and a holding chamber in communication with the first capillary cavity and which accepts the sample liquid in the first capillary cavity transferred by a centrifugal force generated by a rotation around an axial center; a second inlet for collecting a sample liquid that differs from the sample liquid collected by the first inlet; and a second capillary cavity in communication with the second inlet and the holding chamber and which is capable of collecting a sample liquid by a capillary force via the second inlet. Preferably, the first capillary cavity and the second capillary cavity are coupled to each other. In addition, a continuous cavity with a gap in which a capillary force does not act and which communicates with air is provided on one lateral face of the first capillary cavity.

An analyzing method according to the present invention is a sample liquid analyzing method used by an analyzing device that includes a first capillary cavity connected to a first inlet for collecting a sample liquid and which is capable of collecting a sample liquid by a capillary force, a holding chamber in communication with the first capillary cavity and which accepts the sample liquid in the first capillary cavity transferred by a centrifugal force generated by a rotation around an axial center, a second inlet for collecting a sample liquid that differs from the sample liquid collected by the first inlet, and a second capillary cavity coupled with the second inlet and the holding chamber and which is capable of collecting a sample liquid by a capillary force via the second inlet, wherein when injecting a sample liquid directly into the analyzing device, the sample liquid is injected from the first inlet and supplied to the holding chamber, when injecting a sample liquid via a sample injection tool, the sample liquid is injected from the second inlet and supplied to the holding chamber via the second capillary cavity, and reading is performed by accessing a sample liquid transferred from the holding chamber to a measurement chamber.

An analyzing device according to the present invention is an analyzing device having one end of a supplying capillary channel opened at a spot application section formed so as to protrude from an analyzing device main body, the supplying capillary channel connected to a microchannel structure formed inside the analyzing device main body, a sample liquid applied to the spot application section suctioned by a capillary force of the supplying capillary channel, and the analyzing device used for reading in which a suctioned solution is accessed, wherein a leading end of the spot application section is formed as an inclined face, and the end of the supplying capillary channel is opened on the inclined face. Preferably, a closure-preventing recess that communicates with the end of the supplying capillary channel is formed on the inclined face. In addition, the analyzing device main body on which the spot application section is protrudingly formed includes a base substrate on which an internal recess to become the microchannel structure is formed and a cover substrate to be bonded to the base substrate and which closes an opened face of the internal recess, wherein a length of a protrusion of the base substrate forming the spot application section is shorter than a length of a protrusion of the cover substrate forming the spot application section, and a width of the cover substrate forming the spot application section is narrower than a width of the base substrate forming the spot application section.

An analyzing device according to the present invention is an analyzing device having one end of a supplying capillary channel opened at a spot application section formed on an analyzing device main body, the supplying capillary channel connected to a microchannel structure formed inside the analyzing device main body, a sample liquid applied to the spot application section suctioned by a capillary force of the supplying capillary channel and a capillary force of a holding chamber formed inside the analyzing device main body, and the analyzing device used for reading in which a suctioned solution is accessed, wherein a filling confirmation region with a gap that is smaller or greater than a gap of the holding chamber in which a capillary force acts is formed on a trailing end of the holding chamber. Preferably, a confirmation window is formed on the analyzing device main body in correspondence to the filling confirmation region. In addition, the analyzing device main body is configured by bonding a cover substrate with a base substrate having formed on a bonding face with the cover substrate an internal recess that makes up the holding chamber and covering respective opening faces of the internal recess of the holding chamber with the cover substrate, and a gap that is smaller than the gap of the holding chamber in which a capillary force acts provided on the trailing end of the holding chamber is formed between a leading end of a protrusion that protrudes towards the cover substrate from a side of the base substrate and the cover substrate. Furthermore, the analyzing device main body is configured by bonding a cover substrate with a base substrate having formed on a bonding face with the cover substrate an internal recess that makes up the holding chamber and covering respective opening faces of the internal recess of the holding chamber with the cover substrate, and a gap that is greater than the gap of the holding chamber in which a capillary force acts provided on the trailing end of the holding chamber is formed between a bottom of a recess that penetrates on a side of the base substrate towards an opposite side to the cover substrate and the cover substrate.

Advantages of the Invention

An analyzing device according to the present invention suctions a sample liquid into a capillary cavity by a capillary force via a guide section formed so as to extend circumferentially inward from an inlet and in which a capillary force acts, receives a sample liquid transferred from the capillary cavity into a receiving cavity, and includes a bent section formed at a connected section of the guide section and the capillary cavity. Therefore, a sample liquid can be directly collected and internally supplied without using an insertion tool, thereby improving the work efficiency of a user. In addition, analyzing apparatuses can be downsized and load can be reduced.

Furthermore, in a case of an analyzing device having a liquid reservoir that temporarily holds a sample liquid before suction into the guide section and which is formed on a leading end of the guide section, the sample liquid held in the liquid reservoir is automatically suctioned to the inside of the analyzing device via the guide section even when a fingertip is detached from an inlet after spot application. Therefore, user operability can be improved, a fixed amount of a sample liquid can be reliably retrieved, and an improvement in analytical precision can be realized.

An analyzing device according to the present invention includes a partition wall that splits a channel in a width direction formed in a capillary channel at a connected section of a sample measuring section and a receiving section. Therefore, liquid flow due to a capillary force can be accurately controlled by the channel shape, and an accurate measurement can be performed at the sample measuring section.

An analyzing device according to the present invention includes an inclined face formed so that a capillary channel at a connected section of a sample measuring section and a receiving section widens towards the receiving section. Therefore, liquid flow due to a capillary force can be accurately controlled by the channel shape, and an accurate measurement can be performed at the sample measuring section.

An analyzing device according to the present invention includes a spot application section provided such that a proximal end thereof is connected to a capillary cavity and a leading end thereof protrudes from a cover substrate, wherein the leading end of the spot application section is formed in a hemispherical shape protruding in a direction separating from a channel forming face. Therefore, a sample liquid can be made to adhere only to the spot application section.

An analyzing device according to the present invention includes a second inlet for collecting a sample liquid that differs from a sample liquid collected by a first inlet, and a second capillary cavity coupled to the second inlet and a holding chamber and which is capable of collecting a sample liquid by a capillary force via the second inlet. Consequently, an analyzing device can be provided that is capable of suctioning a sample injected from a sample injection tool without leakage from the second inlet, quantifying the sample by a rotational movement, and collecting a sample from the sample injection tool while at the same time enabling a method that uses a conventional puncture tool.

An analyzing device according to the present invention includes a leading end of a spot application section formed in an inclined face and having one end of a supplying capillary channel opened on the inclined face. Therefore, since sampling can be conducted with the inclined face on the leading end of the spot application section arranged in a tilted posture that follows a fingertip of a testee, the influence of gravity during suction of a sample liquid by a capillary force can be reduced, suction speed can be increased, and a prescribed amount of a sample liquid can be sampled in a short period of time.

An analyzing device according to the present invention includes a filling confirmation region with a gap that is smaller or greater than a gap of a holding chamber in which a capillary force acts formed on a trailing end of the holding chamber. Therefore, by bringing a spot application section into contact with a drop of sample liquid and visually checking the filling confirmation region formed on the trailing end of the holding chamber, in the event that a sample liquid is suctioned up to the filling confirmation region, when the filling confirmation region is formed with a smaller gap than a gap of the holding chamber in which a capillary force acts, a state where the sample liquid is suctioned by and sandwiched between the small gap can be visually confirmed upon completion of the suction of a fixed amount of the sample liquid. As a result, deficiencies in sample liquid can be alleviated. In addition, when the filling confirmation region is formed with a greater gap than the gap of the holding chamber in which a capillary force acts, a state where the sample liquid is suctioned around and sandwiched between the great gap can be visually confirmed upon completion of the suction of a fixed amount of the sample liquid. As a result, deficiencies in sample liquid can be alleviated.

BRIEF DESCRIPTION OF THE DRAWINGS

FIG. 12 is a cross-sectional view taken after setting an analyzing device on an analyzing apparatus and rotating the same, and a cross-sectional view taken after centrifugal separation;

FIG. 14 is a cross-sectional view taken when quantitatively collecting a solid component of a sample liquid after centrifugal separation, and a cross-sectional view taken when diluting the solid component of the sample liquid after centrifugal separation;

FIG. 17 is a plan view of a portion between an inlet and a capillary cavity according to the first embodiment of the present invention and a plan view of the same section according to a different embodiment;

FIG. 40 is an enlarged cross-sectional view of a connected section of a microchannel according to the eighth embodiment of the present invention;

FIG. 60 is a process diagram covering from a sample liquid injection process to a measurement chamber filling process when a sample liquid is injected from a second inlet of an analyzing device according to the eighth embodiment of the present invention;

FIG. 109 is an explanatory diagram of sample control and measurement by an analyzing device according to Patent Document 3;

FIG. 110 is an exploded perspective view of an electrochemical biosensor according to Patent Document 4; and FIG. 111 is an explanatory diagram of sample liquid distribution by a centrifugal transfer biosensor according to Patent Document 5.

BEST MODE FOR CARRYING OUT THE INVENTION

First Embodiment

FIGS. 1A, 1B to 6 illustrate an analyzing device of a first embodiment.

Figure 1A:
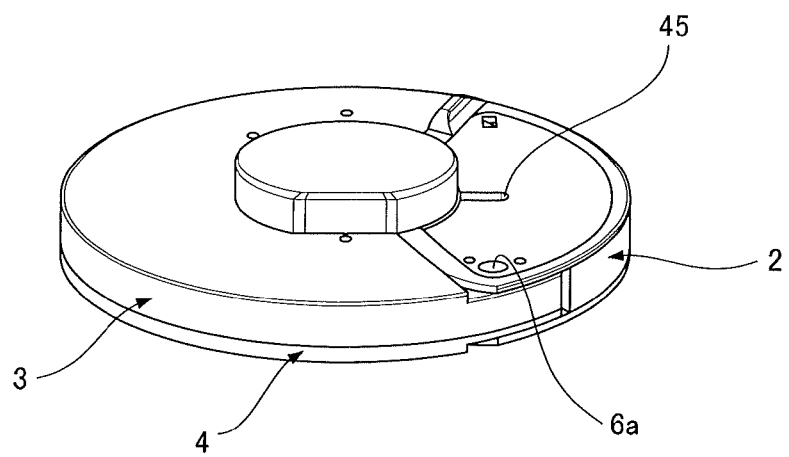
FIG. 1A is an external perspective view of a state where a protective cap of an analyzing device according to a first embodiment of the present invention is closed.
Figure 1B:
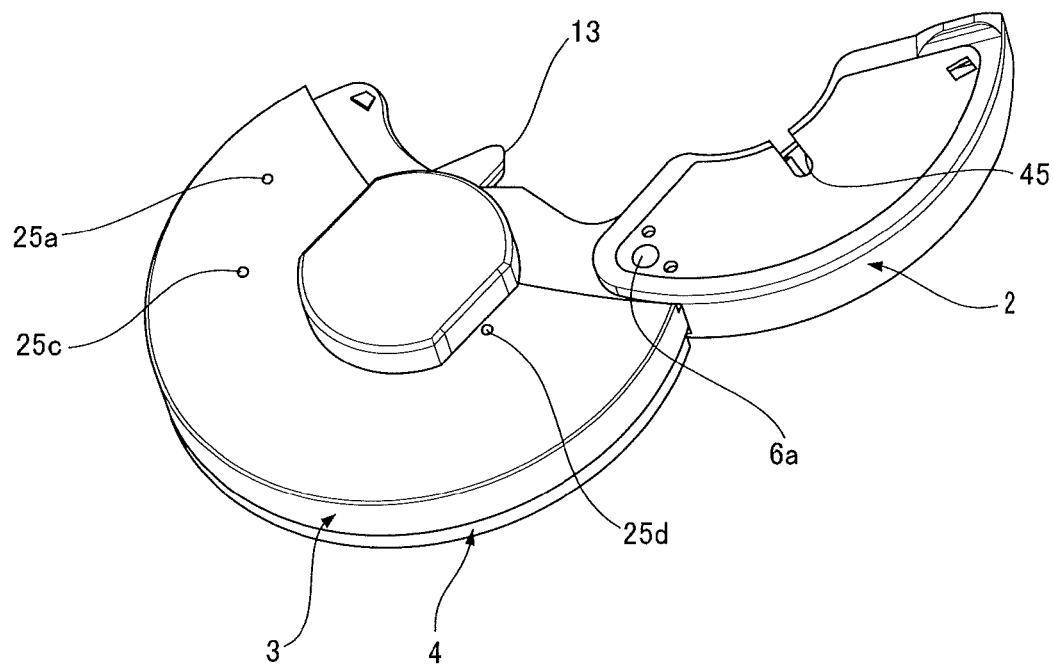
FIG. 1B is an external perspective view of a state where a protective cap according to the first embodiment of the present invention is opened.
Figure 2:
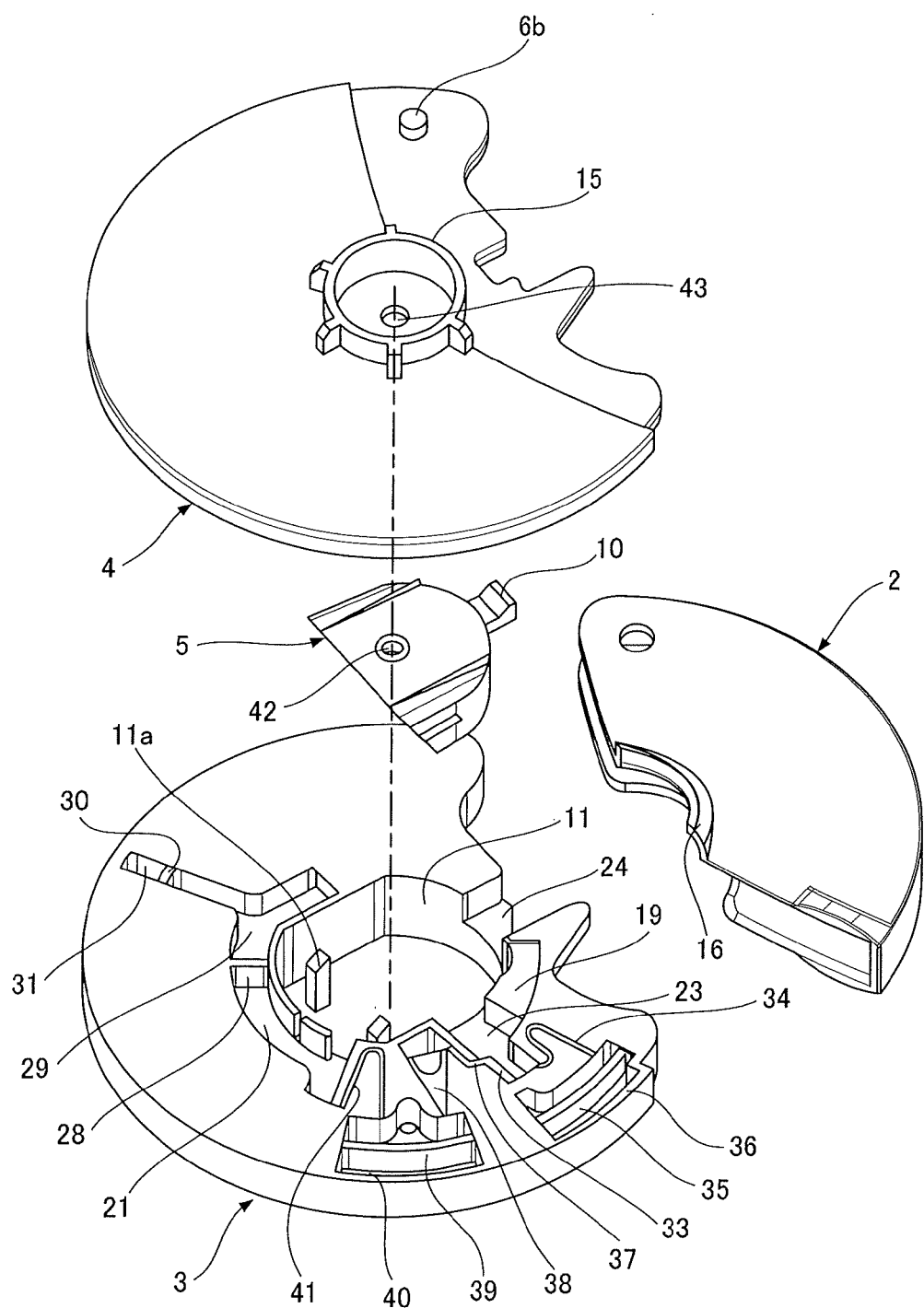
FIG. 2 is an exploded perspective view of an analyzing device according to an embodiment of the present invention.
Figure 3:
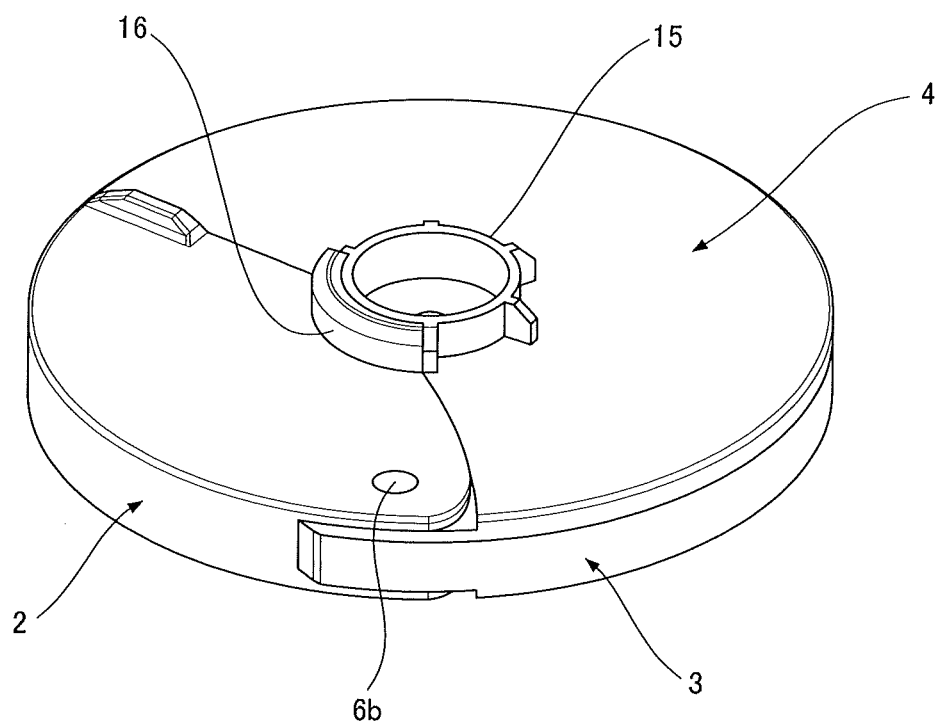
FIG. 3 is a perspective view of an analyzing device in a state where a protective cap is closed as seen from behind.

FIGS. 1A and 1B respectively illustrate a closed state and an opened state of a protective cap 2 of an analyzing device 1. FIG. 2 illustrates an exploded state when a lower side as illustrated in FIG. 1A is faced upwards. FIG. 3 is an assembly diagram of the same.

The analyzing device 1 is made up of four parts including: a base substrate 3 with one face on which is formed a microchannel structure having minute irregularities on a surface thereof; a cover substrate 4 for covering a surface of the base substrate 3; a diluent container 5 holding a diluent; and a protective cap 2 for preventing scattering of a sample liquid.

The base substrate 3 and the cover substrate 4 are bonded in a state where the diluent container 5 and the like are internally set, whereby the protective cap 2 is attached to the base substrate 3 and the cover substrate 4 in the bonded state.

By covering the openings of the several depressions formed on the upper face of the base substrate 3 with the cover substrate 4, a plurality of containment areas to be described later (the same as the measurement spots to be described later) and channels having microchannel structures which interconnect the containment areas are formed. Among the containment areas, those required hold, in advance, reagents necessary for performing various analyses. One side of the protective cap 2 is pivotally supported so as to be capable of engaging shafts 6a and 6b formed on the base substrate 3 and the cover substrate 4 and to be openable and closable. When a sample liquid to be tested is blood, gaps between respective channels with microchannel structures in which capillary force acts are set to 50 μm to 300 μm.

An analysis process using the analyzing device 1 described above can be summarized as spot-applying a sample liquid to the analyzing device 1 in which a diluent has been set in advance, and performing measurement after diluting at least a portion of the sample liquid with the diluent.

Figure 4:
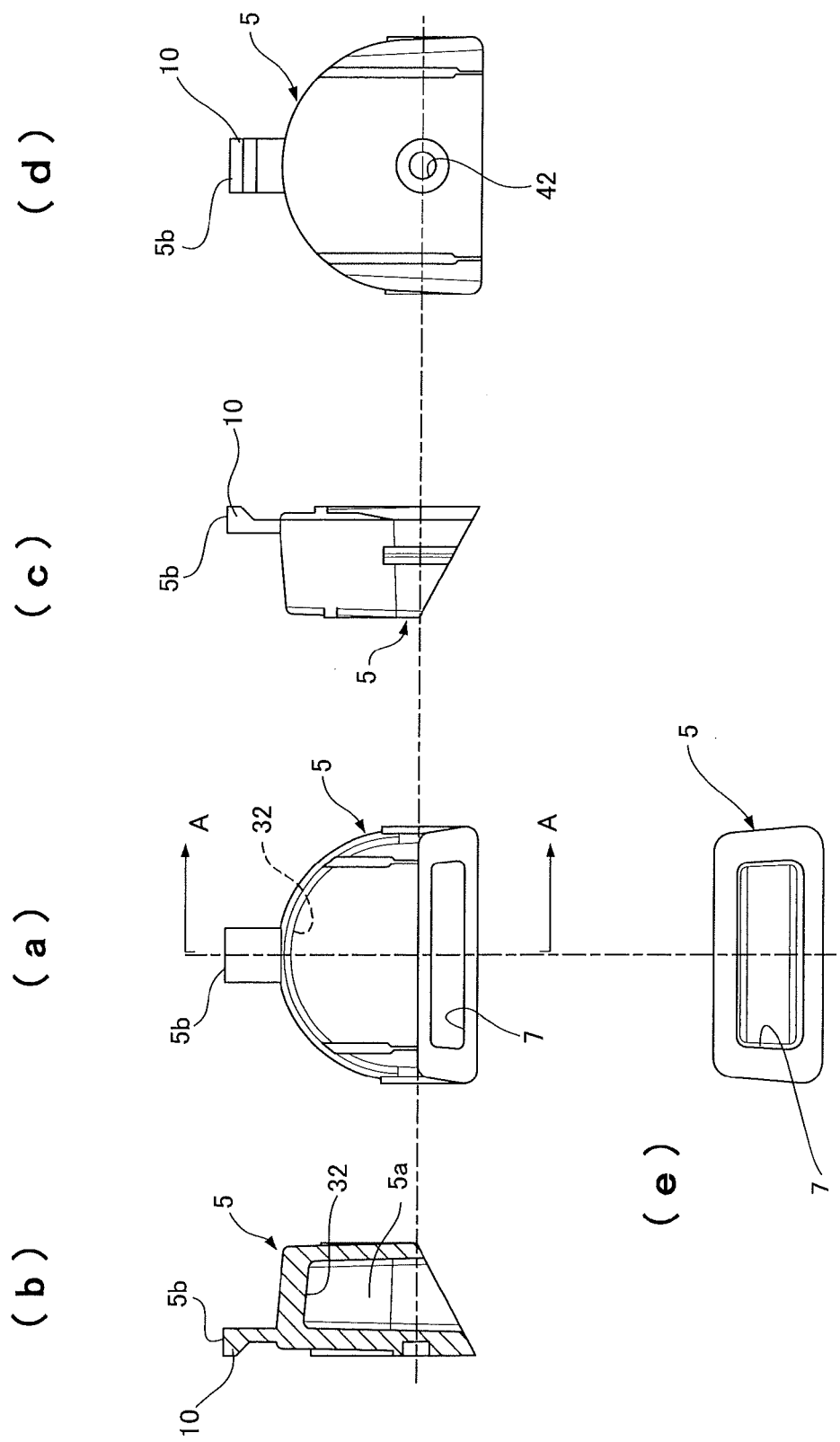
FIG. 4 is an explanatory diagram of a diluent container according to the first embodiment of the present invention.

FIG. 4 illustrates shapes of the diluent container 5.

FIG. 4(a) is a plan view; FIG. 4(b) is a cross-sectional view taken along A-A in FIG. 4(a); FIG. 4(c) is a side view; FIG. 4(d) is a rear view; and FIG. 4(e) is a front view as seen from an opening 7. The opening 7 is sealed by an aluminum seal 9 as a seal member after filling an inside 5a of the diluent container 5 with a diluent 8 as illustrated in FIG. 6(a). A latch 10 is formed on a side of the diluent container 5 opposite to the opening 7. The diluent container 5 is set in and contained by a diluent container containing section 11 formed between the base substrate 3 and the cover substrate 4 so as to be movable to a liquid holding position illustrated in FIG. 6(a) and a liquid discharge position illustrated in FIG. 6(c).

Figure 5:
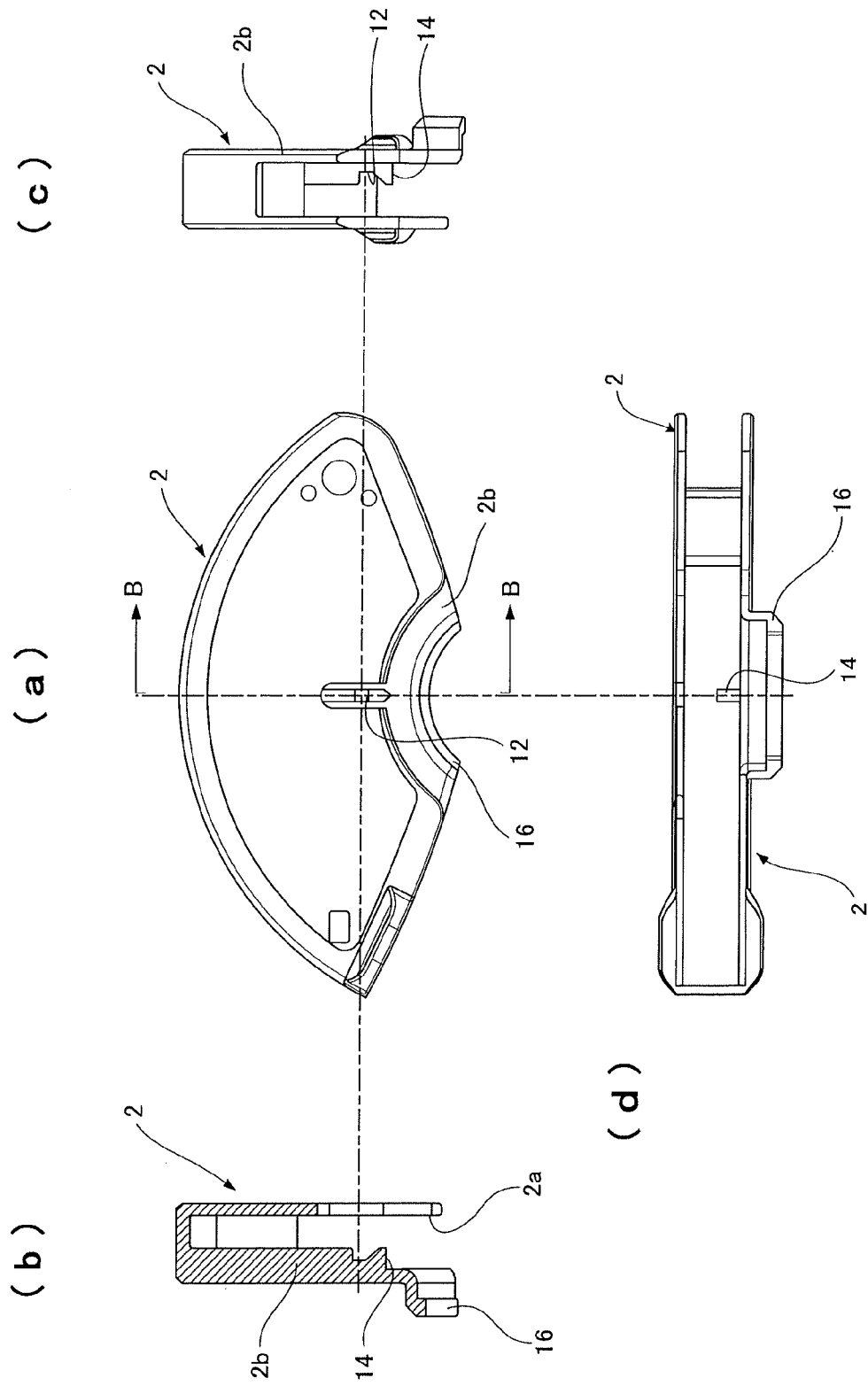
FIG. 5 is an explanatory diagram of a protective cap according to the first embodiment of the present invention.
Figure 6:
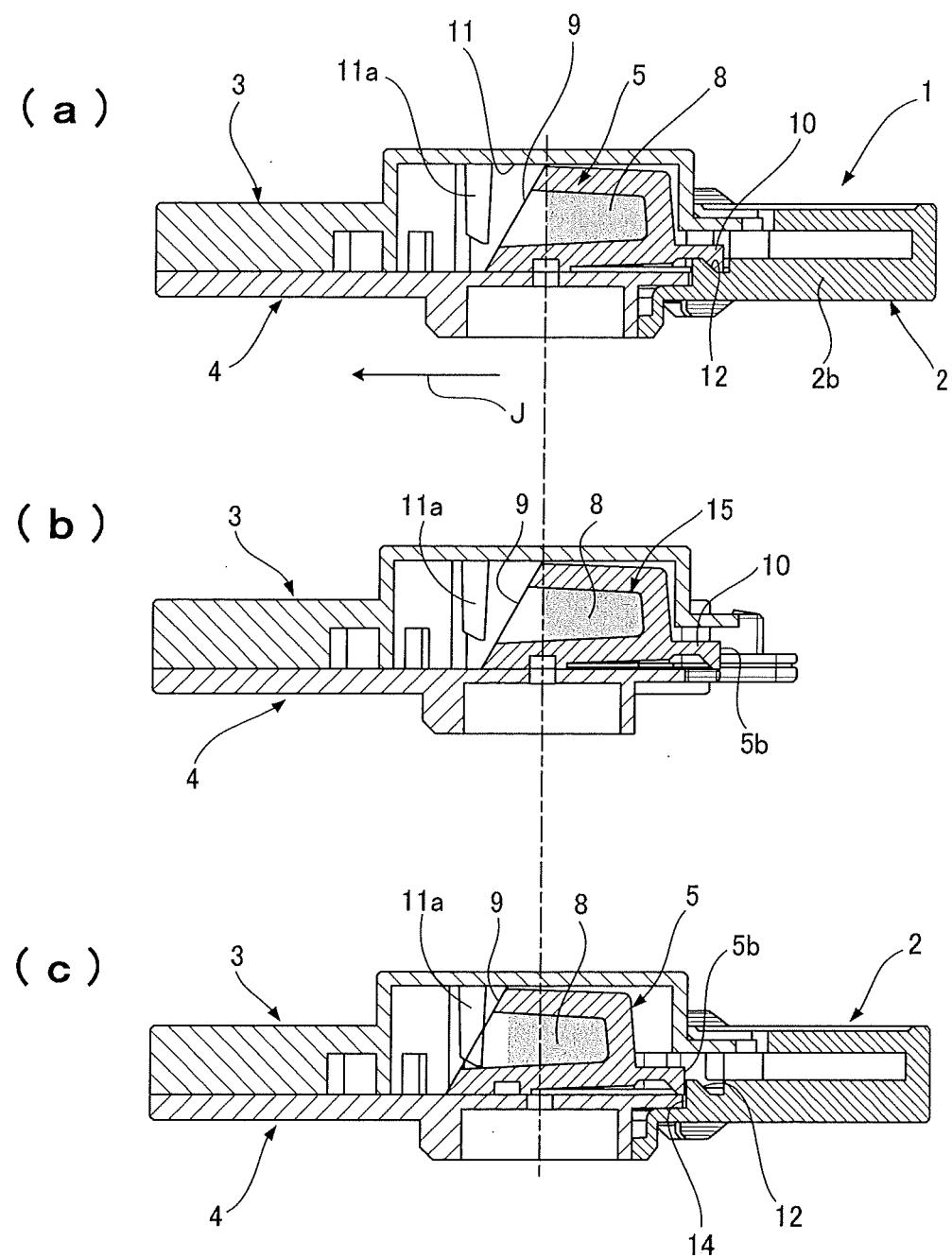
FIG. 6 is a cross-sectional view of an analyzing device according to the first embodiment of the present invention before use, a cross-sectional view of an analyzing device when spot-applying a sample liquid, and a cross-sectional view of an analyzing device when a protective cap is closed after having finished spot-applying the sample liquid.

FIG. 5 illustrates shapes of the protective cap 2.

FIG. 5(a) is a plan view; FIG. 5(b) is a cross-sectional view taken along B-B in FIG. 5(a); FIG. 5(c) is a side view; FIG. 5(d) is a rear view; and FIG. 5(e) is a front view as seen from an opening 2a. As illustrated in FIG. 6(a), a locking groove 12 with which the latch 10 of the diluent container 5 can engage in a closed state illustrated in FIG. 1A is formed on an inner side of the protective cap 2.

FIG. 6(a) illustrates the analyzing device 1 prior to use. In this state, the protective cap 2 is closed and the latch 10 of the diluent container 5 is in engagement with the locking groove 12 of the protective cap 2 so as to lock the diluent container 5 at the liquid holding position and prevent the diluent container 5 from moving in a direction depicted by arrow J. The analyzing device 1 is supplied to a user in this state.

When the protective cap 2 is opened as illustrated in FIG. 1B against the engagement with the latch 10 illustrated in FIG. 6(a) upon spot-application of a sample liquid, a bottom 2b of the protective cap 2 on which the locking groove 12 is formed elastically deforms, causing the engagement between the locking groove 12 of the protective cap 2 and the latch 10 of the diluent container 5 to be released as illustrated in FIG. 6B.

In this case, a sample liquid is spot-applied to an exposed inlet 13 of the analyzing device 1 and the protective cap 2 is closed. At this point, by closing the protective cap 2, a wall face 14 forming the locking groove 12 abuts a face 5b of the latch 10 of the diluent container 5 on a side of the protective cap 2 and pushes the diluent container 5 in the direction of the arrow J (in a direction approaching the liquid discharge position). An opening rib 11a is formed on the diluent container containing section 11 as a protrusion from a side of the base substrate 3. When the diluent container 5 is pushed by the protective cap 2, as illustrated in FIG. 6(c), the aluminum seal 9 applied on the seal face of the inclined opening 7 of the diluent container 5 collides with and is broken by the opening rib 11a.

Figure 7:
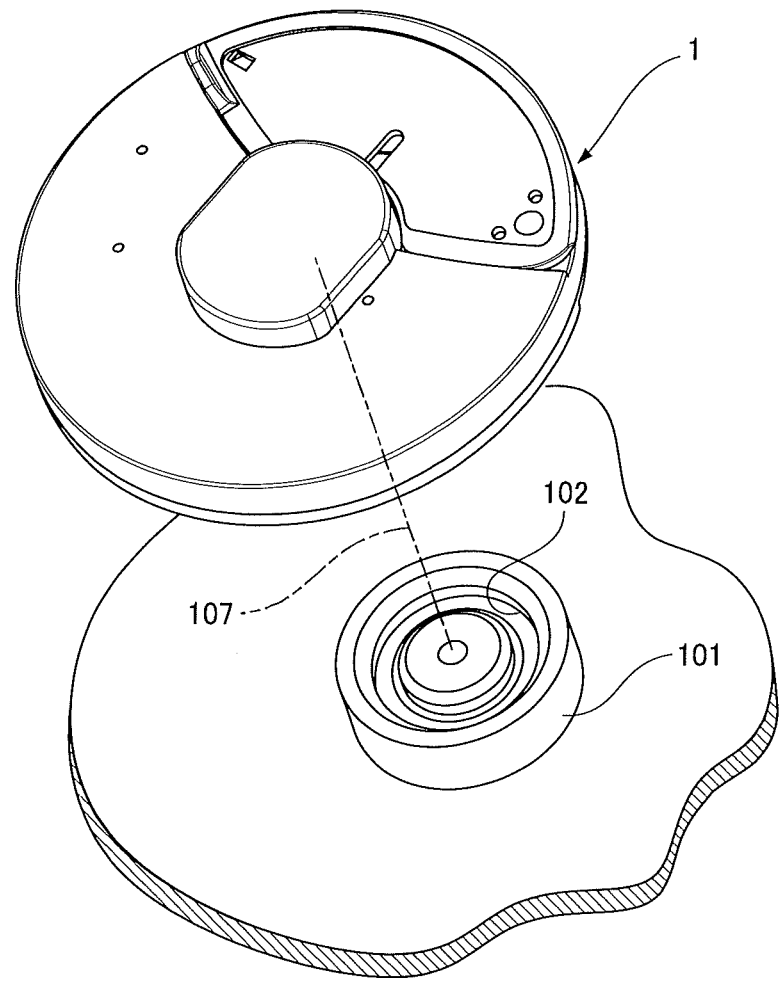
FIG. 7 is a perspective view taken immediately before setting an analyzing device onto an analyzing apparatus.
Figure 8:
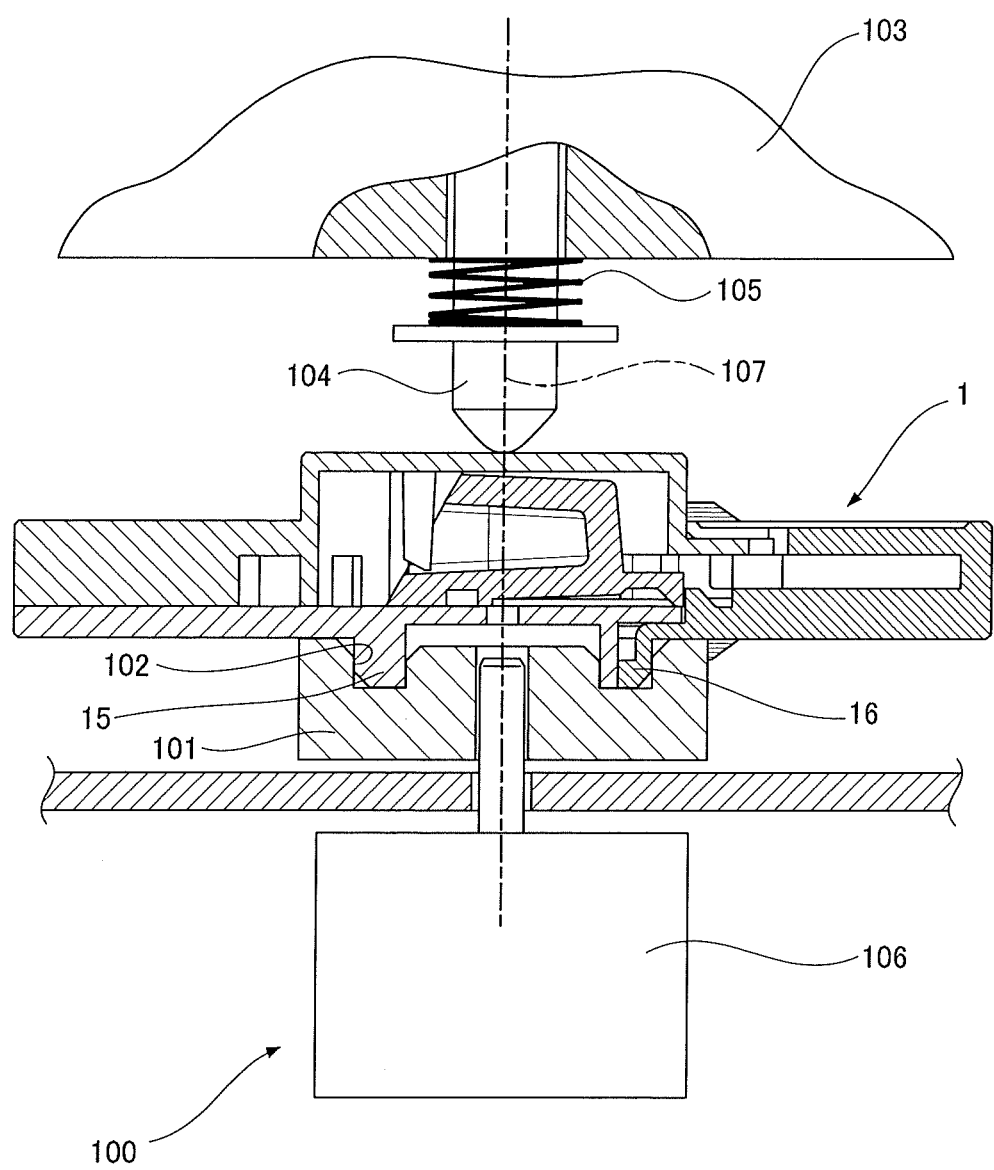
FIG. 8 is a cross-sectional view of a state where an analyzing device has been set on an analyzing apparatus.

A component analysis of a sample liquid can be performed by setting the analyzing device 1 onto a rotor 101 of an analyzing apparatus 100 with the cover substrate 4 facing downwards as illustrated in FIGS. 7 and 8.

A groove 102 is formed on an upper face of the rotor 101. When the analyzing device 1 is set on the rotor 101, a rotation supporting section 15 formed on the cover substrate 4 of the analyzing device 1 and a rotation supporting section 16 formed on the protective cap 2 engages the groove 102 and the analyzing device 1 is contained.

After setting the analyzing device 1 on the rotor 101, when a door 103 of the analyzing apparatus is closed before rotating the rotor 101, a movable piece 104 provided on a side of the door 103 pushes a position of the set analyzing device 1 on the rotation axial center of the rotor 101 towards the rotor 101 using a biasing force of a spring 105, thereby causing the analyzing device 1 to integrally rotate with the rotor 101 that is rotationally driven by a rotation driving unit 106. Reference numeral 107 denotes an axial center during rotation of the rotor 101. The protective cap 2 is attached in order to prevent sample liquid adhering to a vicinity of the inlet 13 from scattering to the outside due to centrifugal force during an analysis.

Resin material with low material cost and superior mass productivity is desirably used for the parts that make up the analyzing device 1. Since the analyzing apparatus 100 analyzes sample liquids using an optical measurement method in which light transmitted through the analyzing device 1 is measured, a synthetic resin with a high optical transparency such as PC, PMMA, AS, MS, and the like is desirably used as the material for the base substrate 3 and the cover substrate 4.

In addition, since it is required that the diluent 8 be sealed inside the diluent container 5 over a long period of time, a crystalline synthetic resin with a low moisture permeability such as PP and PE is desirably used as the material of the diluent container 5. As for the material of the protective cap 2, any material with good moldability shall suffice. Inexpensive resins such as PP and PE are desirable.

The bonding between the base substrate 3 and the cover substrate 4 is desirably performed using a method that is unlikely to affect the reaction activity of reagents held in the containment areas. Desirable methods include ultrasonic welding and laser welding which are less likely to create reactive gases or solvents during bonding.

In addition, a portion for transferring a solution by a capillary force of a minute gap between the base substrate 3 and the cover substrate 4 formed by the bonding of the two substrates 3 and 4 is subjected to a hydrophilic treatment to enhance capillary force. Specifically, a hydrophilic treatment using a hydrophilic polymer or a surfactant is performed. In this case, hydrophilicity refers to a contact angle of less than 90 degrees with respect to water, and more favorably, a contact angle of less than 40 degrees.

Figure 9:
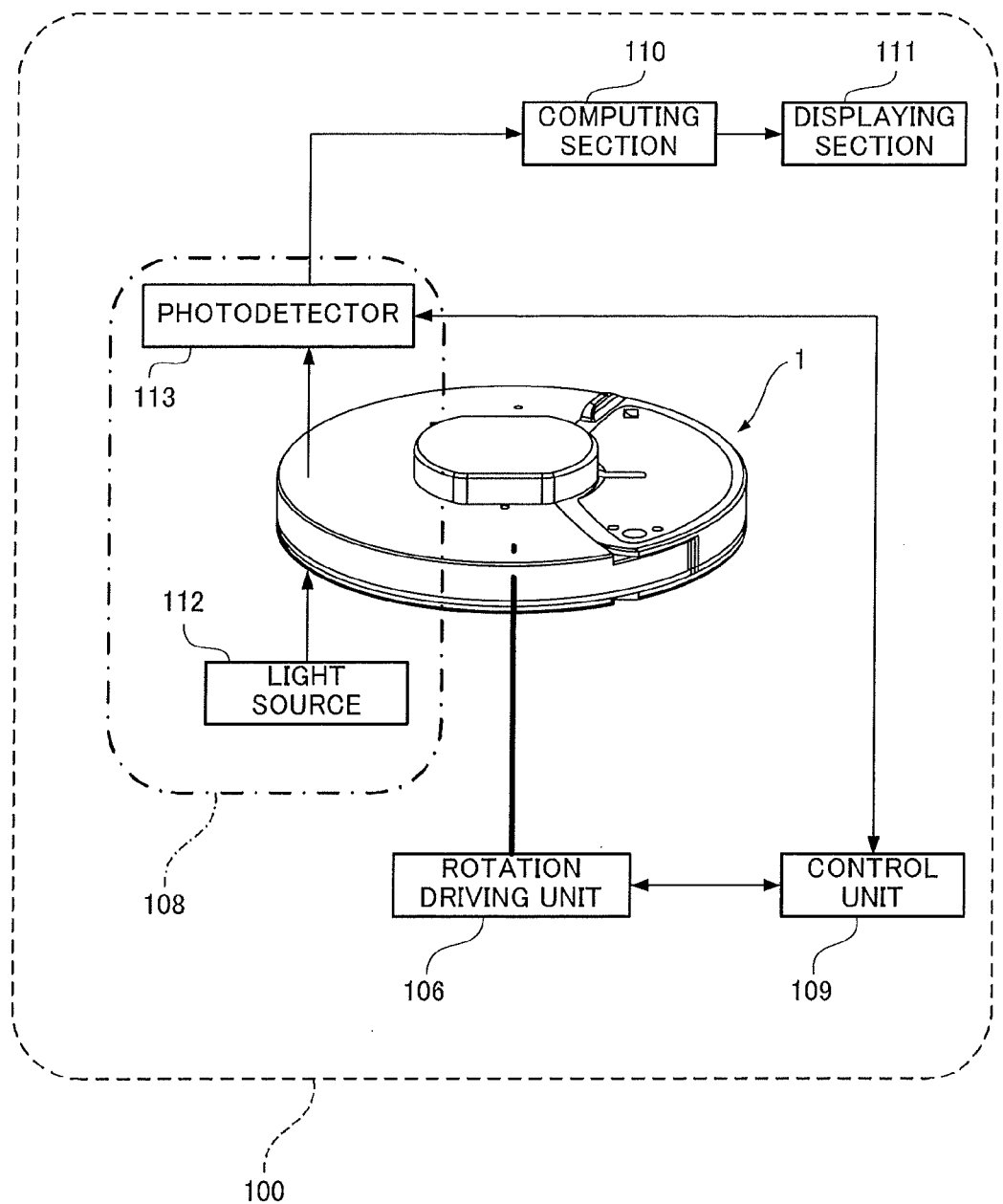
FIG. 9 is a configuration diagram of an analyzing apparatus according to the first embodiment of the present invention.

FIG. 9 illustrates the analyzing apparatus 100.

The analyzing apparatus 100 is made up of: a rotation driving unit 106 for rotating the rotor 101; an optical measurement unit 108 for optically measuring a solution in the analyzing device 1; a control unit 109 that controls the rotational speed and rotational direction of the rotor 101, the measurement timing of the optical measurement unit, and the like; a computing section 110 for processing a signal obtained by the optical measurement unit 108 and computing a measurement result; and a displaying section 111 for displaying a result obtained by the computing section 110.

In addition to rotating the analyzing device 1 around the rotation axial center 107 via the rotor 101 in any direction at a predetermined rotational speed, the rotation driving unit 106 is arranged so as to be capable of causing the analyzing device 1 to perform a left-right reciprocating movement centered around the rotation axial center 107 at a predetermined stop position and at predetermined amplitude range and frequency so as to swing the analyzing device 1.

The optical measurement unit 108 includes: a light source 112 for irradiating light to a measurement section of the analyzing device 1; and a photodetector 113 that detects a light intensity of transmitted light having passed through the analyzing device 1 among the light irradiated from the light source 112.

The analyzing apparatus 100 is arranged such that, by rotationally driving the analyzing device 1 by the rotor 101, a sample liquid or a solution taken inside from the inlet 13 is transferred inside the analyzing device 1 by a centrifugal force that is generated by rotating the analyzing device 1 around the rotation axial center 107 positioned circumferentially inward from the inlet 13 and by a capillary force of a capillary channel provided inside the analyzing device 1. A microchannel structure of the analyzing device 1, together with analysis processes, will now be described in detail.

Figure 10A:
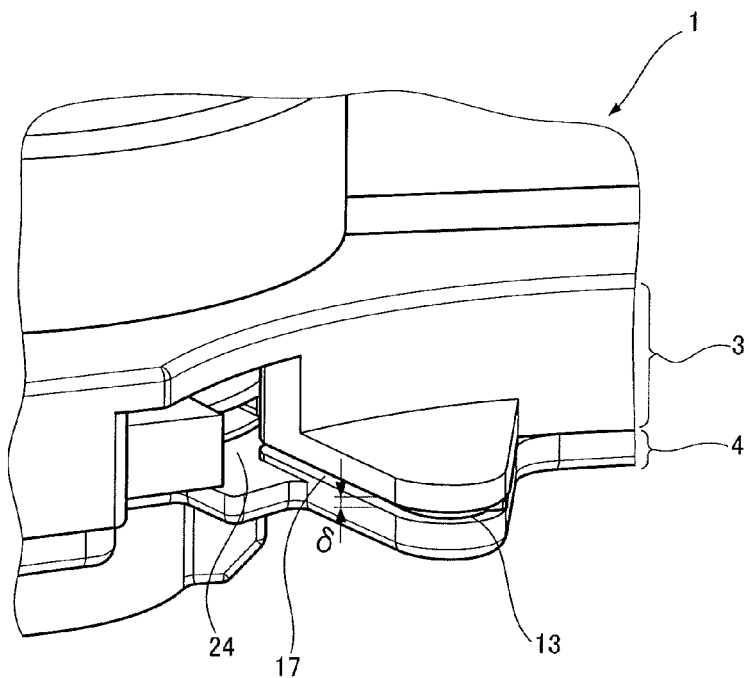
FIG. 10A is an enlarged perspective view of substantial parts of an analyzing device according to the first embodiment of the present invention.
Figure 10B:
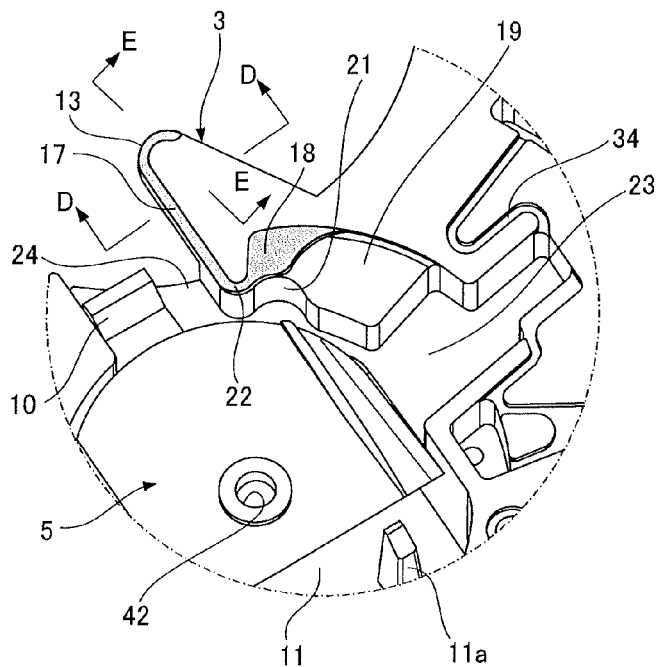
FIG. 10B is an enlarged perspective view of a base substrate of an analyzing device according to the first embodiment of the present invention.
Figure 10C:
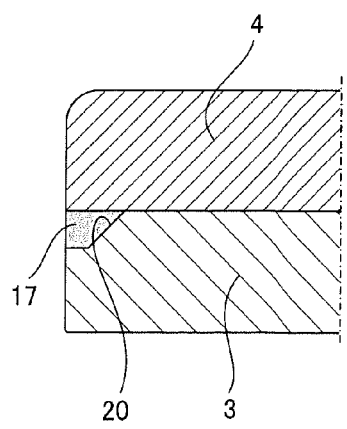
FIG. 10C is an enlarged cross-sectional view of substantial parts of an analyzing device according to the first embodiment of the present invention.

FIGS. 10A, 10B, and 10C illustrate a vicinity of the inlet 13 of the analyzing device 1.

FIG. 10A is an enlarged view of the inlet 13 as seen from the outside of the analyzing device 1, and FIG. 10B is an enlarged view of the microchannel structure as seen through the cover substrate 4 from a side of the rotor 101. The inlet 13 is shaped so as to protrude circumferentially outward from the rotation axial center 107 set inside the analyzing device 1 and is connected to a capillary cavity 19 capable of holding a required amount by a capillary force via a guide section 17 having a minute gap 8 and formed between the base substrate 3 and the cover substrate 4 so as to extend circumferentially inward and in which a capillary force acts. Therefore, by opening the protective cap 2 and directly applying a sample liquid 18 to the inlet 13, a sample liquid adhering to a vicinity of the inlet 13 is retrieved into the analyzing device 1 by the capillary force of the guide section 17.

Figure 18:
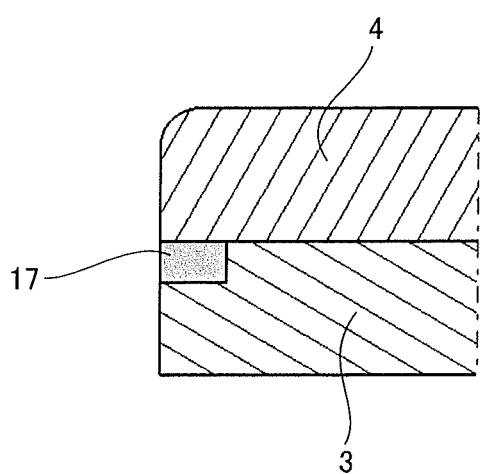
FIG. 18 is cross-sectional view of a comparison example according to the first embodiment of the present invention.

Instead of being a rectangular shape whose back end-side is vertical as illustrated in FIG. 18, a cross-sectional shape (a D-D cross section illustrated in FIG. 10B) perpendicular to a flow direction of the guide section 17 is formed by an inclined face 20 that gradually narrows towards a back end thereof in the direction of the cover substrate 4 as illustrated in FIG. 10C. A bent section 22 that forms a recess 21 on the base substrate 3 and alters the direction of a passage is formed at a connected portion between the guide section 17 and the capillary cavity 19.

A separation cavity 23 as a receiving cavity with a gap at which capillary force does not act is formed via and beyond the capillary cavity 19 as seen from the guide section 17. A cavity 24 whose one end is connected to the separation cavity 23 and the other end opened to the air is formed to a side of the capillary cavity 19 and parts of the bent section 22 and the guide section 17. Due to the action of the cavity 24, as illustrated in FIG. 10B, a sample liquid collected from the inlet 13 is filled, preferentially travelling along side walls of the guide section 17 and the capillary cavity 19 on a side where the cavity 24 is not formed. Consequently, the air inside the capillary cavity 19 is discharged towards the cavity 24 and the sample liquid 18 can be filled without involving air bubbles.

Figure 11:
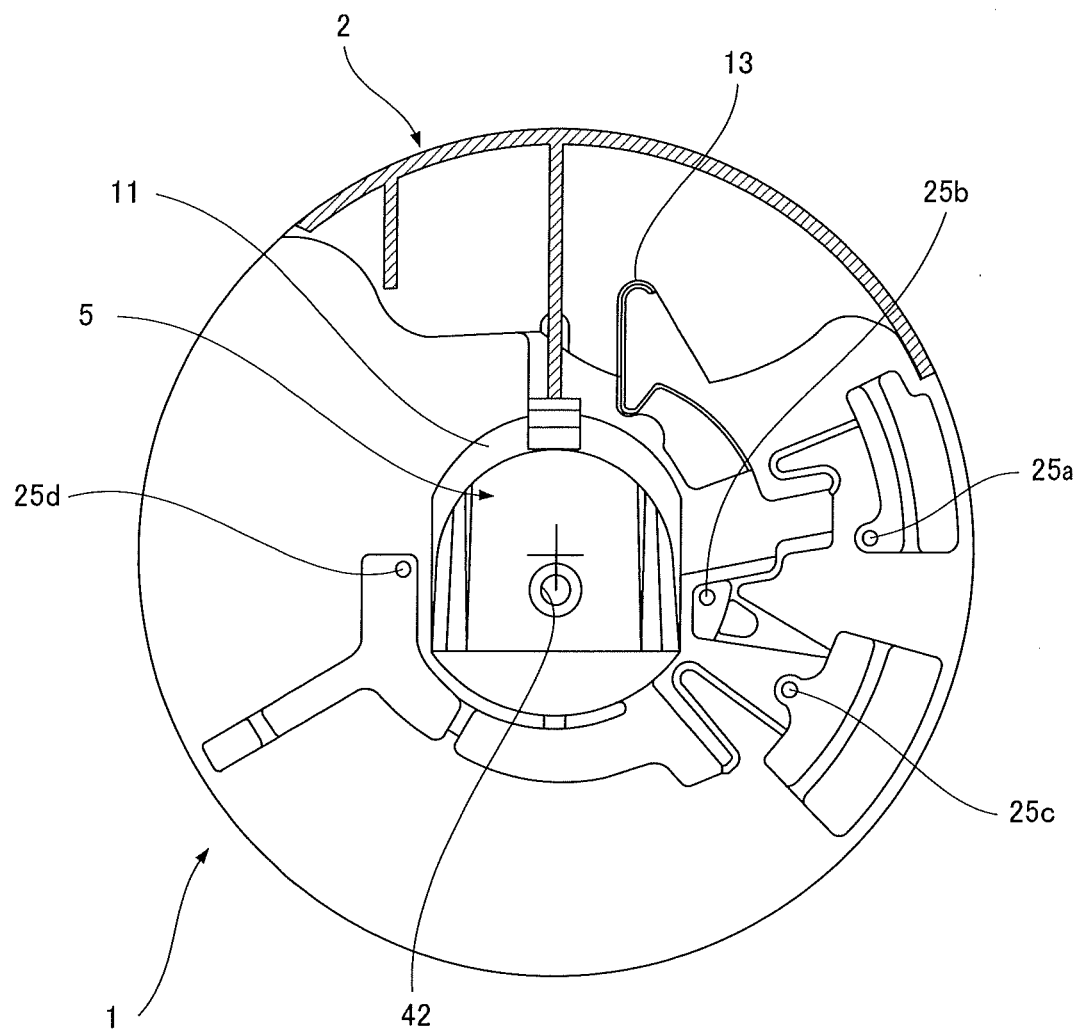
FIG. 11 is a cross-sectional view taken after setting an analyzing device on an analyzing apparatus and before starting rotation.

FIG. 11 illustrates a state of the analyzing device 1 set on the rotor 101 after spot application and before rotation. At this point, as described with reference to FIG. 6(c), the aluminum seal 9 of the diluent container 5 has already collided with the opening rib 11a and has been broken. Reference characters 25a, 25b, 25c, and 25d denote air ducts formed on the base substrate 3.

Process 1

The analyzing device 1 is set on the rotor 101 in a state where, as illustrated in FIG. 12A, a sample liquid is held in the capillary cavity 19 and the aluminum seal 9 of the diluent container 5 has been broken.

Process 2

Figure 15A:
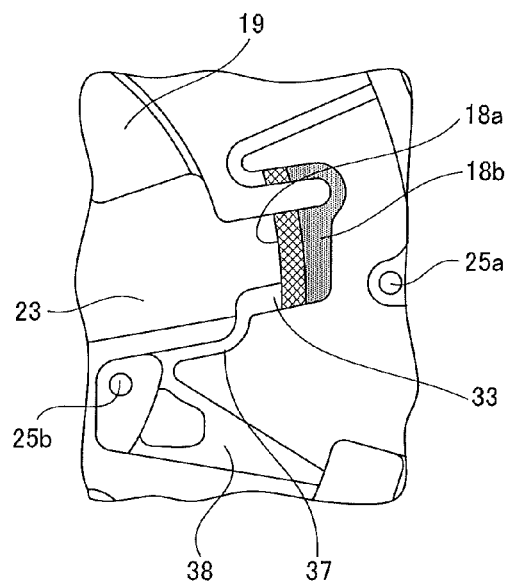
FIG. 15A is an enlarged view of substantial parts.

When the rotor 101 is rotationally driven clockwise (direction depicted by C2) after closing the door 103, the held sample liquid is broken at the position of the bent section 22. A sample liquid inside the guide section 17 is discharged into the protective cap 2. The sample liquid 18 inside the capillary cavity 19 flows into the separation cavity 23 and is centrifugally separated in the separation cavity 23 into a blood plasma component 18a and a blood cell component 18b as illustrated in FIGS. 12(b) and 15A. The diluent 8 having flowed out from the diluent container 5 flows into a holding cavity 27 via discharge channels 26a and 26b. When the diluent 8 having flowed into the holding cavity 27 exceeds a predetermined amount, a surplus of the diluent 8 flows into an overflow cavity 29 via an overflow channel 28 and further flows into a reference measurement chamber 31 via a rib 30 for preventing reflux.

Figure 13:
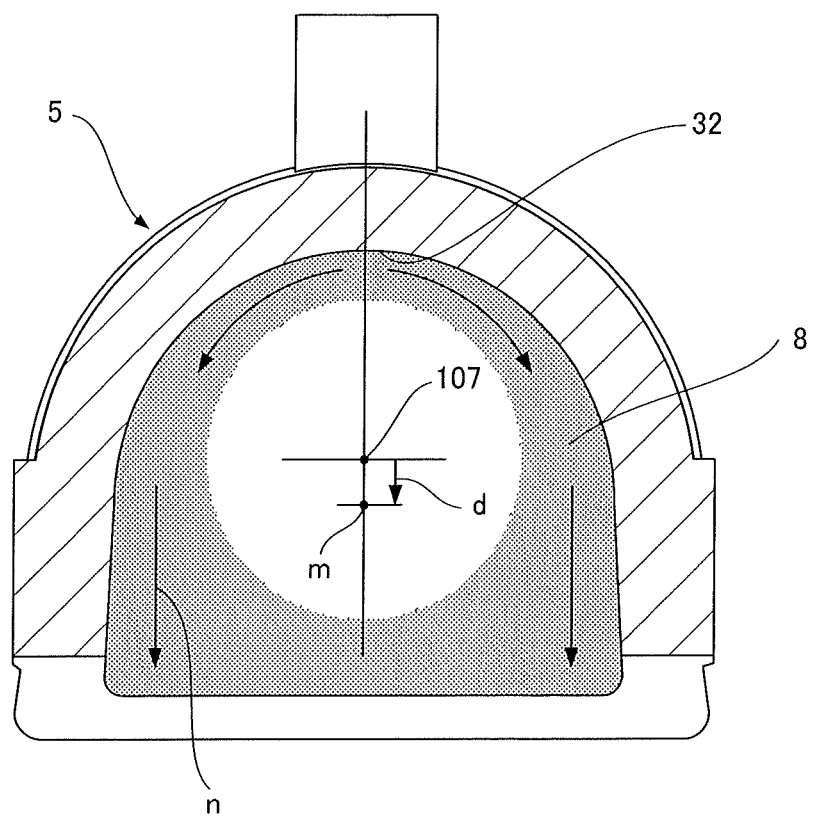
FIG. 13 is a cross-sectional view illustrating an axial center of rotation of an analyzing device and a position of a diluent container at a timing where a diluent is discharged from the diluent container.

With respect to the diluent container 5, the shape of a bottom on the opposite side to the opening 7 sealed by the aluminum seal 9 is formed by an arc face 32 as illustrated in FIGS. 4(a) and 4(b). At the same time, at the liquid discharge position of the diluent container 5 illustrated in FIG. 12(b), the arc face 32 is formed offset by a distance d so that a center m of the arc face 32 becomes closer to a side of the discharge channel 26b than the axial center 107 as illustrated in FIG. 13. Consequently, the diluent 8 having flowed towards the arc face 32 is changed so as to flow along the arc face 32 and towards the opening 7 from the outside (direction depicted by arrow n), and is efficiently discharged from the opening 7 of the diluent container 5 to the diluent container containing section 11.

Process 3

Figure 15B:
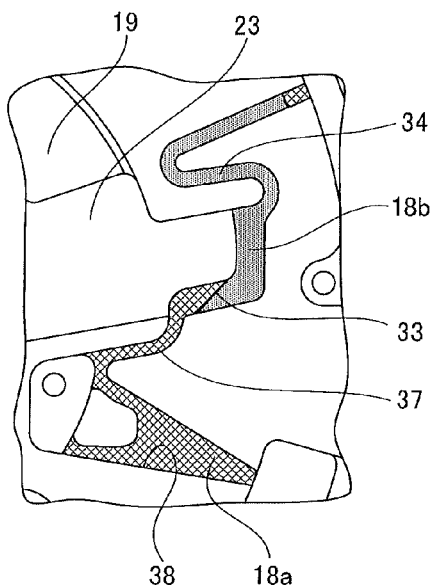
FIG. 15B is an enlarged view of a substantial parts.
Figure 15C:
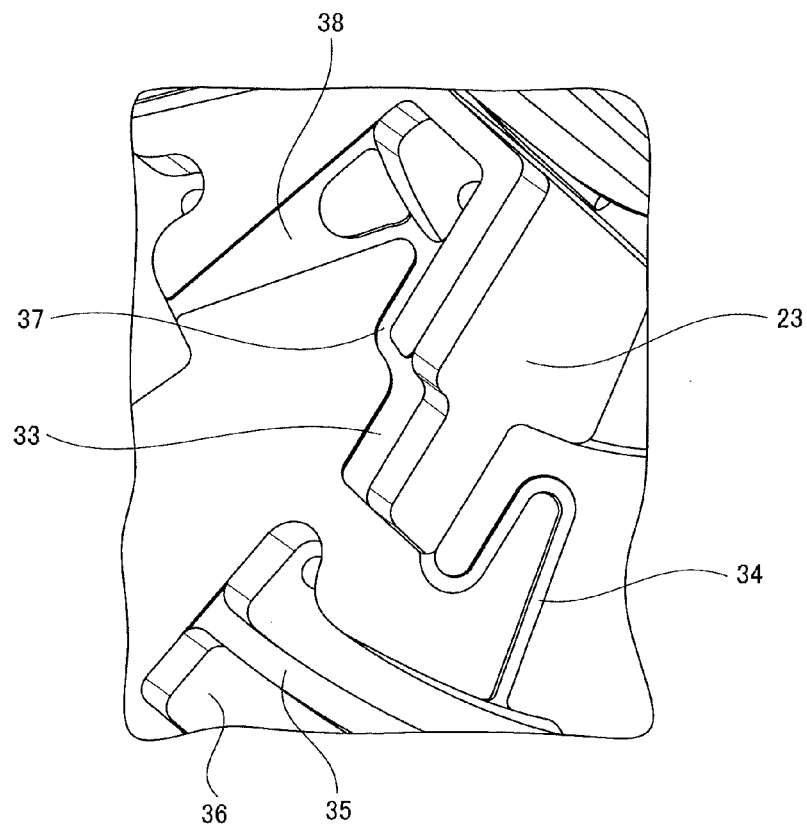
FIG. 15C is a perspective view of substantial parts.

Next, when the rotation of the rotor 101 is stopped, the blood plasma component 18a is siphoned by a capillary cavity 33 formed on a wall face of the separation cavity 23 and then flows into a measurement channel 38 via a capillary channel 37 that communicates with the capillary cavity 33 as illustrated in FIGS. 14(a) and 15B, and a fixed quantity is retained. FIG. 15C is a perspective view illustrating the capillary cavity 33 and a vicinity of the same.

Process 4

When the rotor 101 is rotationally driven counter-clockwise (direction depicted by C1), as illustrated in FIG. 14(b), the blood plasma component 18a held in the measurement channel 38 flows into a measurement chamber 40 via a reflux-preventing rib 39. In addition, the diluent 8 in the holding cavity 27 flows into the measurement chamber 40 via a siphon-shaped connecting channel 41 and the reflux-preventing rib 39. Furthermore, a sample liquid in the separation cavity 23 flows into an overflow cavity 36 via a siphon-shaped connecting channel 34 and a reflux-preventing rib 35. Subsequently, as necessary, the rotor 101 is reciprocatively rotationally moved counter-clockwise (direction depicted by C1) and clockwise (direction depicted by C2) in a swinging motion to agitate a measurement object solution made up of a reagent, the diluent 8, and the blood plasma component 18a held in the measurement chamber.

Process 5

The rotor 101 is rotated counter-clockwise (direction depicted by C1) or clockwise (direction depicted by C2). A reference value is determined when the computing section 110 reads a detected value of the photodetector 113 at a timing where a measurement spot of the reference measurement chamber 31 passes between the light source 112 and the photodetector 113. Furthermore, the computing section 110 reads a detected value of the photodetector 113 at a timing where a measurement spot of the measurement chamber 40 passes between the light source 112 and the photodetector 113 to calculate a specific component based on the reference value.

As seen, since a user can open the diluent container 5 and transfer a diluted liquid into the analyzing device 1 by an opening/closing operation of the protective cap 2 when collecting a sample liquid, an analyzing apparatus can be simplified, cost can be reduced, and user operability can be improved.

Furthermore, since the diluent container 5 sealed by the aluminum seal 9 as a seal member is used and the diluent container 5 is opened by breaking the aluminum seal 9 with the opening rib 11a as a protrusion, a diluent does not evaporate and decrease even during long-term preservation, thereby enabling improvement in analytical precision to be realized.

Moreover, in a shipping state of the analyzing device 1 illustrated in FIG. 6(a), the latch 10 of the diluent container 5 engages the locking groove 12 of the closed protective cap 2 and the diluent container 5 is locked at the liquid holding position and prevented from moving in the direction of arrow J. Although the diluent container 5 is arranged so as to be movable in the diluent container containing section 11 by an opening/closing operation of the protective cap 2, the position of the diluent container 5 at the diluent container containing section 11 is locked at the liquid holding position until the user opens the protective cap 2 to use the diluent container 5. As a result, an accidental opening of the diluent container 5 and spillage of the diluent during transport by the user prior to use can be prevented.

Figure 16:
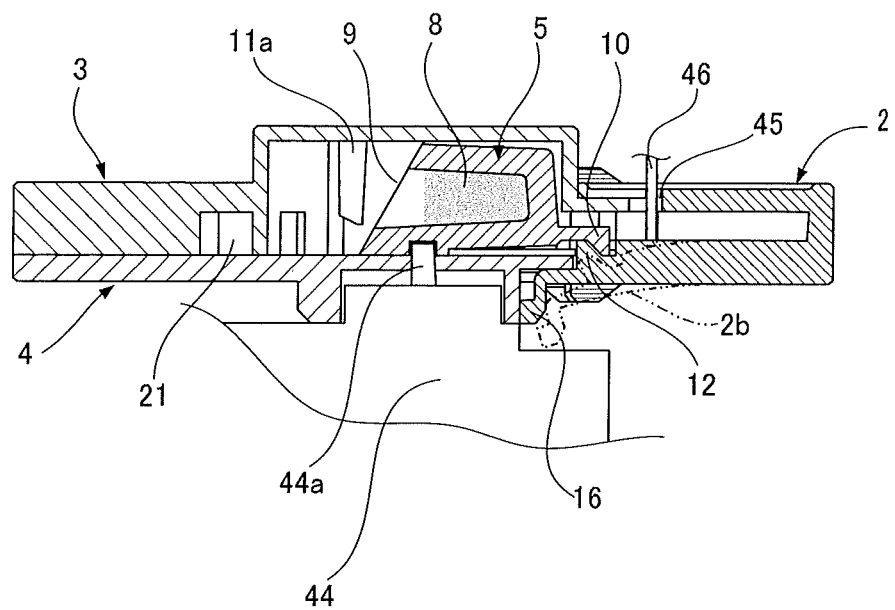
FIG. 16 is a cross-sectional view of a process for setting to a shipping state.

FIG. 16 illustrates a manufacturing process in which the analyzing device 1 is set to the shipping state illustrated in FIG. 6(a). First, before closing the protective cap 2, a groove 42 (refer to FIGS. 2 and 4(d)) provided on a lower face of the diluent container 5 and a hole 43 provided on the cover substrate 4 are aligned. At this liquid holding position, a protrusion 44a of a locking jig 44 provided separate from the base substrate 3 or the cover substrate 4 is brought into engagement with the groove 42 of the diluent container 5 through the hole 43, thereby setting the diluent container 5 in a state where the diluent container 5 is locked at the liquid holding position. Subsequently, a pressing jig 46 is inserted through a notch 45 (refer to FIG. 1B) formed on an upper face of the protective cap 2 so as to press the bottom face of the protective cap 2 to cause elastic deformation. In this elastically deformed state, the analyzing device 1 can be set to the state illustrated in FIG. 6(a) by closing the protective cap 2 and then releasing the pressing jig 46.

Shapes from the inlet 13 to a vicinity of the capillary cavity 19 will be described in detail.

As illustrated in FIGS. 10B and 17(a), the bent section 22 and the recess 21 are formed at the connected section of the guide section 17 and the capillary cavity 19 so as to change a passage direction. Accordingly, in "Process 2" described above, when rotationally driving the rotor 101 clockwise (direction depicted by C2), a sample liquid held in the capillary cavity 19 is broken at the position of the bent section 22 and a fixed amount of the sample liquid can be transferred to the separation cavity 23. In other words, breaking the sample liquid held in the capillary cavity 19 at the position of the bent section 22 means that an amount of the sample liquid to be discharged into the protective cap 2 can be limited to just a minute amount in the guide section 17. Therefore, a situation where the sample liquid held in the capillary cavity 19 is accidentally discharged inside the protective cap 2 can be avoided, which is effective in maintaining safety. In this case, a distance L1 from the rotation axial center 107 (a center of the groove 42 provided on a lower face of the diluent container 5) to the bent section 22 and a distance L2 from the rotation axial center 107 to the capillary cavity 19 are set such that L1=L2.

Furthermore, for the purpose of improving safety, as illustrated in FIG. 17(b), the bent section 22 is desirably formed at a circumferentially inward position with respect to the capillary cavity 19 (L1<L2).

Moreover, as illustrated in FIG. 10C, a cross-sectional shape of the guide section 17 is formed as an inclined face 20 that gradually narrows towards the cover substrate 4 the further towards a rearmost end of the inclined face 20. Therefore, even with a minute amount of a sample liquid, as illustrated in FIG. 18, a greater capillary force acts in comparison to a case where the cross-sectional shape of the guide section 17 is formed as a cross-sectional rectangular that remains constant towards the rearmost end of the cross-sectional rectangular. As a result, a sample liquid can be reliably retrieved towards the capillary cavity 19 and an amount of a sample liquid that is lost in the guide section 17 can be reduced.

In addition, since the analyzing apparatus 100 rotationally drives the analyzing device 1 around the rotation axial center 107 (the center of the groove 42 provided on a lower face of the diluent container 5) set inside the analyzing device 1, a turning radius can be reduced in comparison to a conventional analyzing apparatus that rotationally drives the analyzing device 1 around an axial center set to the outside of the analyzing device 1, thereby enabling downsizing to be achieved.

In each embodiment presented above, a case where the groove 42 is provided on a lower face of the diluent container 5 has been described as an example. Alternatively, the groove 42 may be provided on an upper face of the diluent container 5, and the hole 43 may be provided on the base substrate 3 so as to correspond to the groove 42, whereby the protrusion 44a of the locking jig 44 is to be brought into engagement with the groove 42.

In the embodiment described above, the locking groove 12 of the protective cap 2 directly engages the latch 10 of the diluent container 5 to lock the diluent container 5 at the liquid holding position. Alternatively, the diluent container 5 may be locked at the liquid holding position by having the locking groove 12 of the protective cap 2 and the latch 10 of the diluent container 5 indirectly engage each other.

In each embodiment presented above, a case has been described as an example in which a component centrifugally separated from a sample liquid by rotating the analyzing device 1 around the rotation axial center 107 and the diluent 8 discharged from the diluent container 5 are transferred to the measurement chamber 40 to be diluted, whereby analysis is performed by accessing a solution component separated from a sample liquid or a reactant of a solution component separated from a sample liquid and a reagent. However, when a solution component need not be separated from a sample liquid, the separation process is no longer required. In this case, the analyzing device 1 is rotated around the rotation axial center 107 to transfer all of a fixed amount of a sample liquid among a spot-applied sample liquid and the diluent 8 discharged from the diluent container 5 to the measurement chamber 40 to be diluted, whereby analysis is performed by accessing a solution component diluted by the diluent or a reactant of a solution component diluted by the diluent and a reagent. Alternatively, the analyzing device 1 may be rotated around the rotation axial center 107 to transfer a solid component separated from a sample liquid and a diluent discharged from the diluent container 5 to the measurement chamber to be diluted, whereby analysis may be performed by accessing the solid component separated from the sample liquid or a reactant of the solid component separated from the sample liquid and a reagent.

In the embodiment described above, an analyzing device main body having, formed inside, a microchannel structure with minute surface irregularities is structured with two layers, namely, the base substrate 3 and the cover substrate 4. Alternatively, the analyzing device main body may be structured by pasting together three or more substrates. Conceivable specific examples include a three-layer structure that is a microchannel structure formed by setting a substrate notched according to a microchannel structure at center, pasting separate substrates on an upper face and a lower face of the central substrate, and closing the notches.

Second Embodiment

FIGS. 21A, 21B to 23 illustrate a vicinity of an inlet 13 of an analyzing device 1 according to a second embodiment of the present invention. Other parts are the same as the first embodiment.

Figure 19:
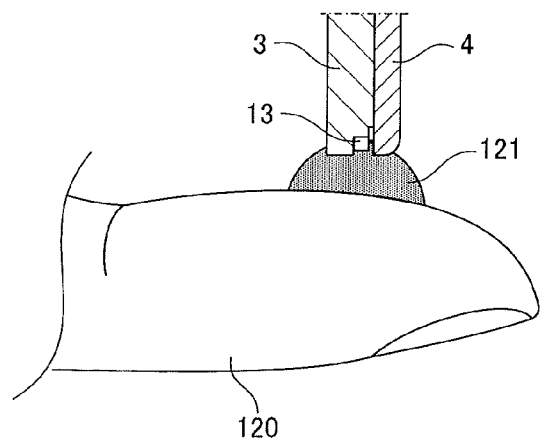
FIG. 19 is an explanatory diagram of an in-use state of an analyzing device according to the first embodiment of the present invention.
Figure 20:
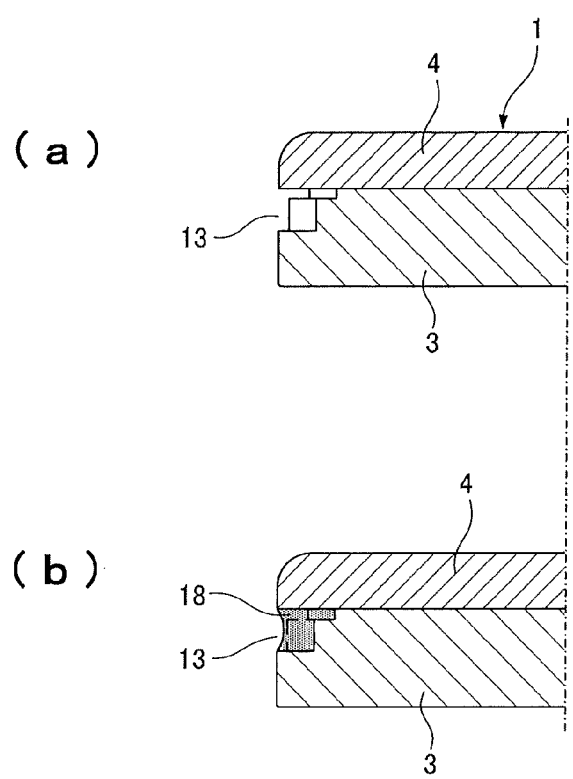
FIG. 20 is a cross-sectional view taken along E-E in FIG. 10B.

With the structure of the analyzing device 1 according to the first embodiment, as illustrated in FIG. 19, by setting the analyzing device 1 to a vertical posture and bringing the inlet 13 in contact with the blood drop 121 on the fingertip 120 of a testee, blood as a sample is suctioned up to the capillary cavity 19 by the capillary forces of the guide section 17 and the capillary cavity 19. However, it has become apparent that when suctioning a sample liquid with the analyzing device 1 set in a vertical posture, gravity acting on the sample liquid impairs suction power and significantly increases suction time. In addition, while the inlet 13 must be kept in contact with the fingertip 120 during suction, it has also become apparent that holding the analyzing device 1 in the same posture so as to maintain contact with the fingertip 120 of the testee for several tens of seconds or more is not user-friendly. FIG. 20(a) is a cross-sectional view of a vicinity of the inlet 13 and the guide section 17 indicated by an E-E cross section in FIG. 10B, and FIG. 20(b) illustrates a state where the sample liquid (blood) 18 is adhered to the inlet 13.

Figure 21A:
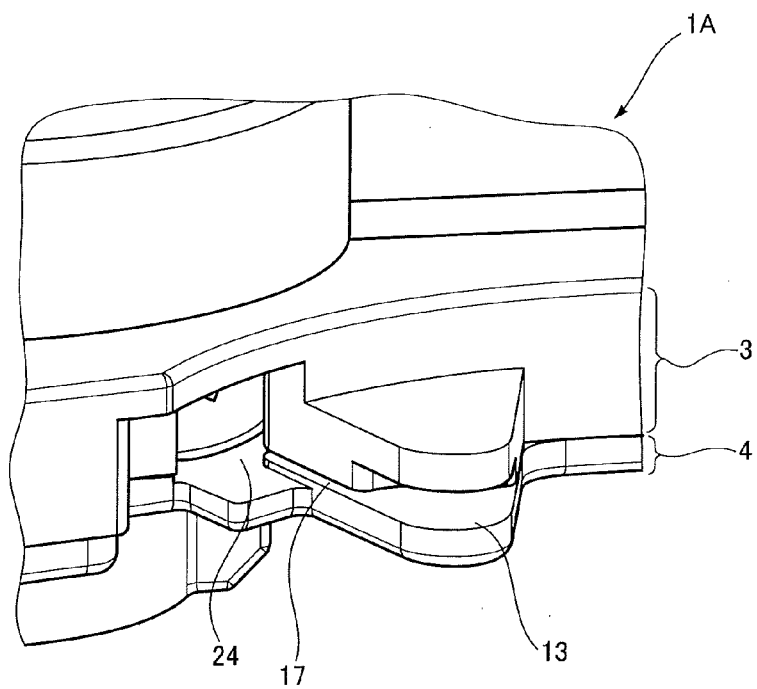
FIG. 21A is an enlarged perspective view of substantial parts of an analyzing device according to a second embodiment of the present invention.
Figure 21B:
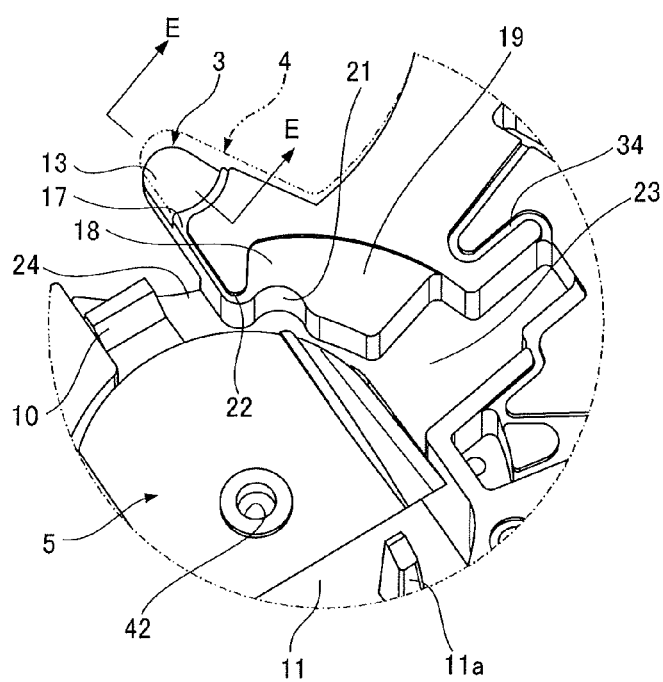
FIG. 21B is an enlarged perspective view of a base substrate according to the second embodiment of the present invention.
Figure 22:
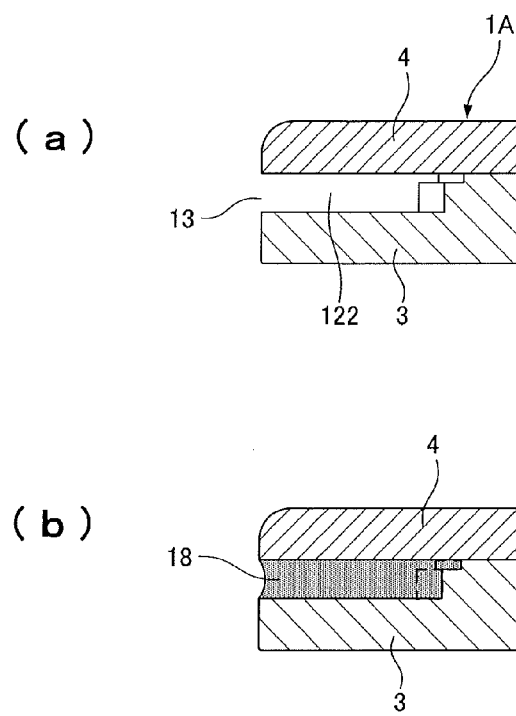
FIG. 22 is a cross-sectional view taken along E-E in FIG. 21B before and after spot application.

In consideration thereof, in the present second embodiment, a part of an inner face of a base substrate 3 forming a portion of an inlet 13 of the base substrate 3 and a cover substrate 4 as illustrated in FIG. 21A is thinly molded towards a guide section 17 over a longer distance than the case of FIG. 10A as illustrated in FIGS. 21B and 22(a) so as to form a liquid reservoir 122 on a leading end of the guide section 17.

Figure 23:
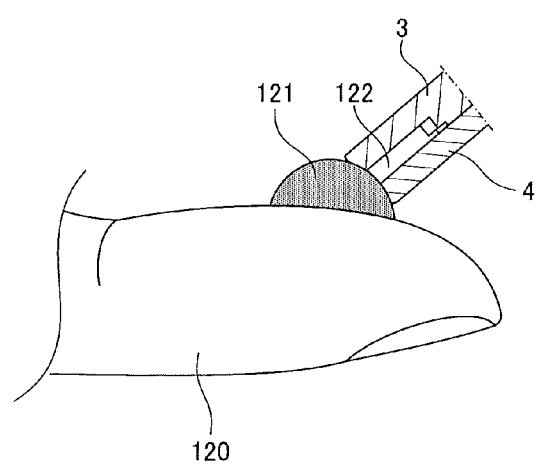
FIG. 23 is an explanatory diagram of an in-use state of an analyzing device according to the second embodiment of the present invention.

In the case of the structure of the analyzing device 1 in which a liquid reservoir 122 is formed, by setting the analyzing device 1 to a vertical posture or by inclining the posture of the analyzing device 1 as illustrated in FIG. 23 and bringing the inlet 13 into contact with a blood drop 121 on a fingertip 120 of a testee, a gap of the liquid reservoir 122 is instantaneously filled by a surface tension of blood 18. While a capacity of the liquid reservoir 122 is desirably set to at least a fixed amount of blood necessary for carrying out analysis, when a large amount of blood is required, the capacity may be set to about half of the required amount of blood.

Due to such a configuration, even when the analyzing device 1 is detached from the fingertip after the inlet 13 is brought into contact with the blood drop 121, as illustrated in FIG. 22(b), blood as a sample pooled in the liquid reservoir 122 is suctioned up to a capillary cavity 19 by the capillary forces of the guide section 17 and the capillary cavity 19. In addition, after detaching the analyzing device 1 from the fingertip, by maintaining the analyzing device 1 at a posture such as a horizontal posture in which gravity is less likely to affect suction of a sample liquid, blood suction time can be reduced. Furthermore, since a fixed amount of blood can be sampled even when a period of time in which the analyzing device 1 is brought into contact with the fingertip 120 of the testee is shorter than what is conventional, accurate analysis can be realized.

Third Embodiment

FIGS. 24A, 24B to 26 illustrate a vicinity of an inlet 13 of an analyzing device 1B according to a third embodiment of the present invention. Other parts are the same as the first embodiment.

Figure 24A:
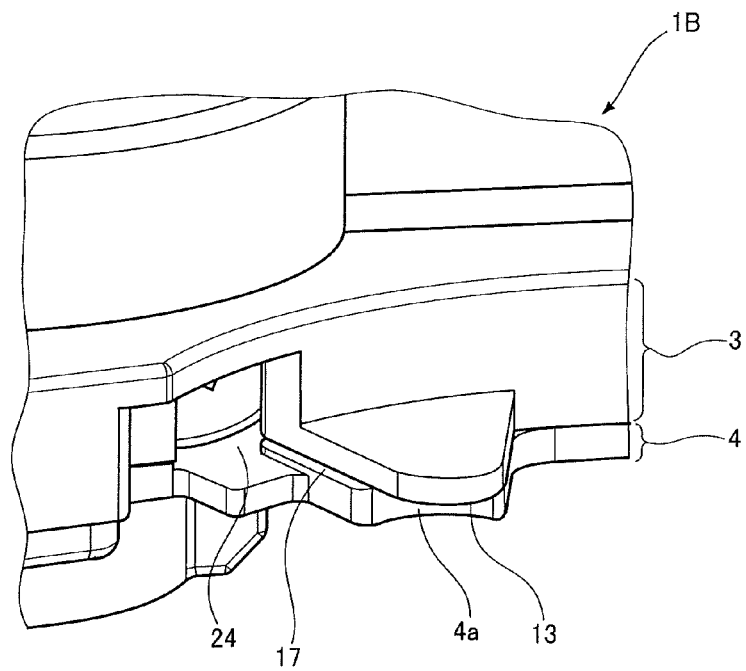
FIG. 24A is an enlarged perspective view of substantial parts of an analyzing device according to a third embodiment of the present invention.
Figure 24B:
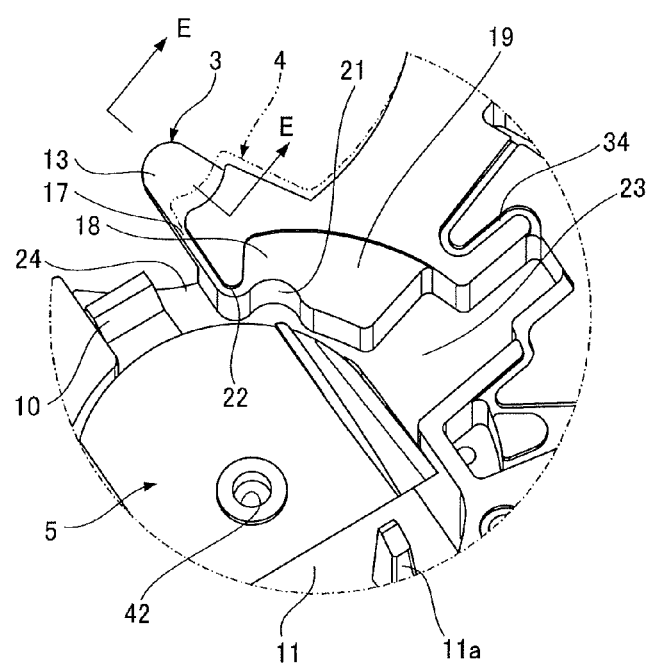
FIG. 24B is an enlarged perspective view of a base substrate according to the third embodiment of the present invention.
Figure 25:
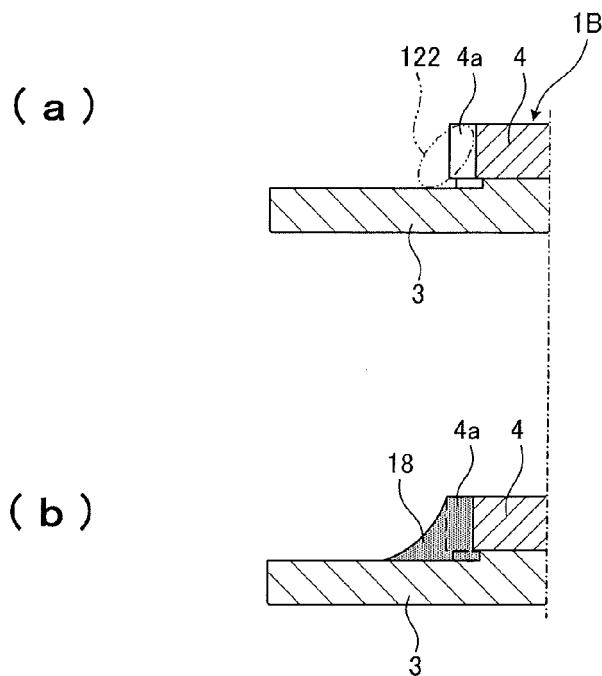
FIG. 25 is a cross-sectional view taken along E-E in FIG. 24B before and after spot application.

With the analyzing device 1 according to the second embodiment described above, a portion of the inner face of the base substrate 3 is thinly molded so as to form the liquid reservoir 122. However, with the analyzing device 1B according to the present third embodiment, by reducing a length of a cover substrate 4 forming a portion of an inlet 13 of a base substrate 3 and the cover substrate 4 as illustrated in FIG. 24A in comparison with the base substrate 3 as illustrated in FIGS. 24B and 25(a) and forming a leading end 4a of the cover substrate 4 in an arc-like shape, a liquid reservoir 122 is formed on a leading end of a guide section 17.

Figure 26:
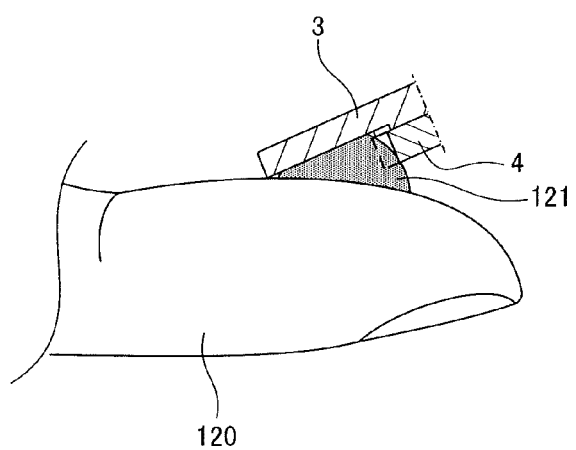
FIG. 26 is an explanatory diagram of an in-use state of an analyzing device according to the third embodiment of the present invention.

In the case of the structure of the analyzing device 1B in which a liquid reservoir 122 is formed, by inclining the posture of the analyzing device 1 as illustrated in FIG. 26 and bringing the inlet 13 into contact with a blood drop 121 on a fingertip 120 of a testee, a fixed amount of blood necessary for carrying out analysis adheres to the liquid reservoir 122 by the surface tension of blood 18 as illustrated in FIG. 25(b).

Due to such a configuration, even when the analyzing device 1 is detached from the fingertip after the inlet 13 is brought into contact with the blood drop 121, blood as a sample adhered to the liquid reservoir 122 is suctioned up to a capillary cavity 19 by the capillary forces of the guide section 17 and the capillary cavity 19. In addition, after detaching the analyzing device 1 from the fingertip, by maintaining the analyzing device 1 at a posture such as a horizontal posture in which gravity is less likely to affect suction of a sample liquid, blood suction time can be reduced. Furthermore, since a fixed amount of blood can be sampled even when a period of time in which the analyzing device 1 is brought into contact with the fingertip 120 of the testee is shorter than what is conventional, accurate analysis can be realized.

Fourth Embodiment

FIGS. 27A, 27B to 29 illustrate a vicinity of an inlet 13 of an analyzing device 1C according to a fourth embodiment of the present invention. Other parts are the same as the first embodiment.

Figure 27A:
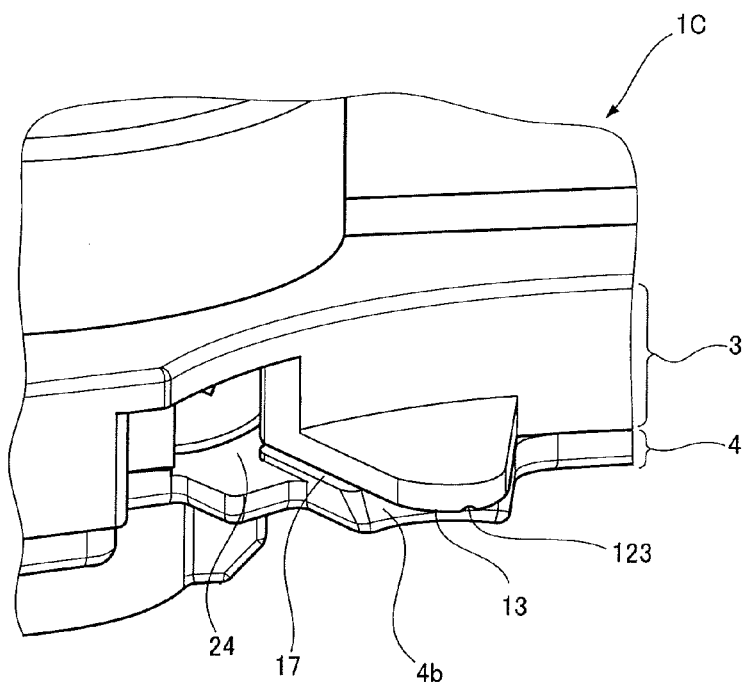
FIG. 27A is an enlarged perspective view of substantial parts of an analyzing device according to a fourth embodiment of the present invention.
Figure 27B:
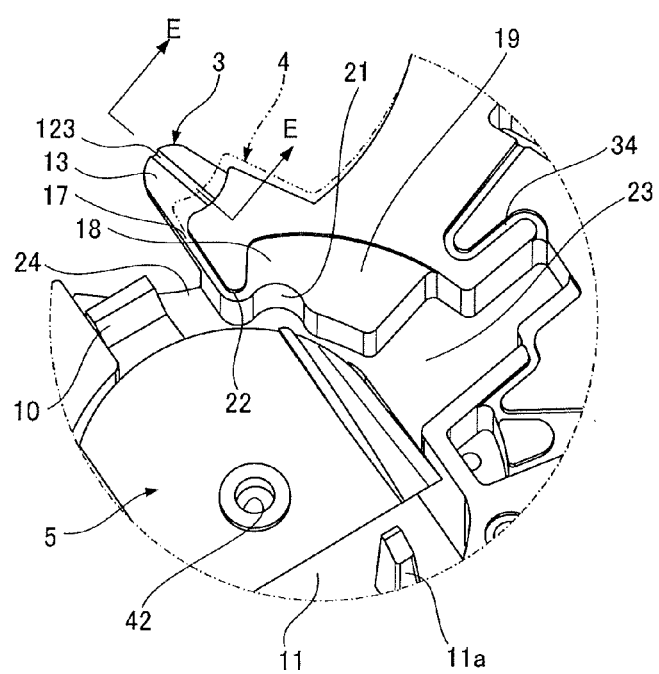
FIG. 27B is an enlarged perspective view of a base substrate according to the fourth embodiment of the present invention.
Figure 28:
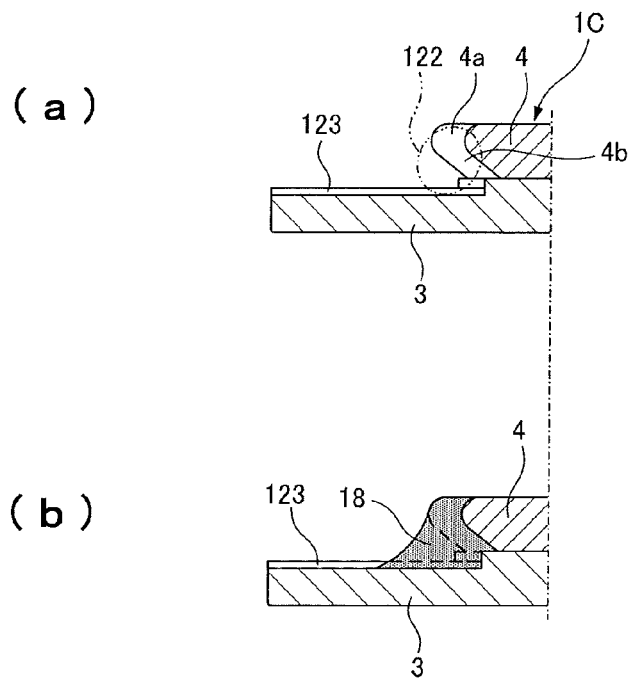
FIG. 28 is a cross-sectional view taken along E-E in FIG. 27B before and after spot application.

With the analyzing device 1B according to the third embodiment described above, the liquid reservoir 122 formed in an arc-like shape on the leading end 4a of the cover substrate 4 is formed as an arc-like shape perpendicular to the base substrate 3. However, with the analyzing device 1C according to the present fourth embodiment, as illustrated in FIGS. 27A and 28(a), a liquid reservoir 122 is formed between an inlet 13 by forming a leading end 4a of a cover substrate 4 so as to have an arc-like planar shape and by forming a cross-sectional shape of the leading end 4a as an inclined face 4b whose side of the base substrate 3 is receded to a side of the guide section 17. In addition, a groove 123 reaching the liquid reservoir 122 from a leading end of the inlet 13 is formed on an inner face of the base substrate 3 of the inlet 13.

Figure 29:
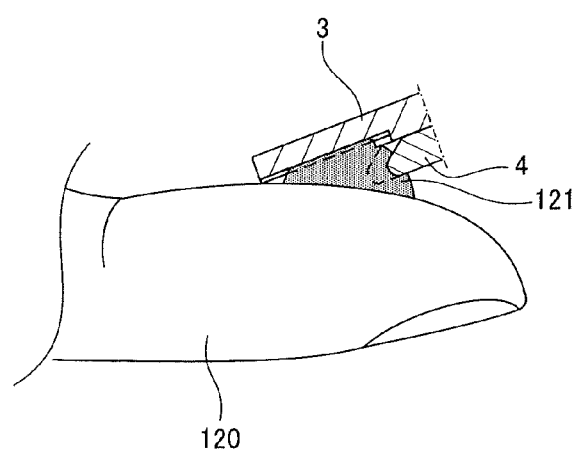
FIG. 29 is an explanatory diagram of an in-use state of an analyzing device according to the fourth embodiment of the present invention.

In the case of the structure of the analyzing device 1C in which a liquid reservoir 122 is formed, by inclining the posture of the analyzing device 1 as illustrated in FIG. 29 and bringing the inlet 13 into contact with a blood drop 121 on a fingertip 120 of a testee, a fixed amount of blood necessary for carrying out analysis adheres to the liquid reservoir 122 by the surface tension of blood 18 as illustrated in FIG. 28(b). Furthermore, since air at a rearmost end of the liquid reservoir 122 is smoothly discharged via the groove 123, the fixed amount of blood can be adhered to the liquid reservoir 122 in a prompt manner.

Due to such a configuration, even when the analyzing device 1 is detached from the fingertip after the inlet 13 is brought into contact with the blood drop 121, blood as a sample adhered to the liquid reservoir 122 is suctioned up to a capillary cavity 19 by the capillary forces of the guide section 17 and the capillary cavity 19. In addition, after detaching the analyzing device 1 from the fingertip, by maintaining the analyzing device 1 at a posture such as a horizontal posture in which gravity is less likely to affect suction of a sample liquid, blood suction time can be reduced. Furthermore, by forming the groove 123, even when blood is not spherically formed on the fingertip (a state where blood wets and spreads across the fingertip), blood can be guided to the guide section 17 via the groove 123. While only one groove 123 has been formed in the present embodiment, a plurality of grooves may be formed. Moreover, the cross-sectional shape of the groove 123 may be formed so as to have an arc-like shape, a triangular shape, or a quadrangular shape.

Fifth Embodiment

For the respective embodiments described above, the case of an analyzing device that transfers a sample liquid suctioned via a guide section 17 and a capillary cavity 19 to a subsequent-stage measurement chamber 40 and which is to be used for reading involving accessing a test object in the measurement chamber 40 as a measurement spot has been described as an example. However, even in a case of an analyzing device that directly suctions a sample liquid from an inlet 13 to a measurement chamber having a capillary force and which is to be used for reading involving accessing a test object in the measurement chamber, by providing the liquid reservoir 122 described in the second to fourth embodiments, blood adhering to the liquid reservoir 122 can be suctioned by a capillary force of a measurement chamber even when the inlet 13 is only brought into contact with a blood drop for a short period of time. Consequently, the fixed amount of blood can be sampled and accurate analysis can be realized.

In addition, a filter member can be provided on a part of or all of the liquid reservoir 122 according to the respective embodiments described above, whereby a component to be suctioned from the liquid reservoir 122 into the guide section 17 having a capillary force or into a measurement chamber having a capillary force can be selected by the filter member. Specifically, when the sample liquid is blood, by preventing or reducing the passage of a blood cell component by the filter member, a component to come into contact with a reagent inside the measurement chamber can be selected, thereby enabling a precise reaction between the reagent and a blood plasma component and a reduction in variances in the reaction. Consequently, an improvement in analytical precision can be expected.

Sixth Embodiment

The gap between the base substrate 3 and the cover substrate 4 at the portion of the capillary cavity 19 illustrated in FIG. 10B is constant in a blood-transferring direction. In addition, the gap between the base substrate 3 and the cover substrate 4 at the boundary between the capillary cavity 19 and the separation cavity 23 is constant in a direction crossing the blood-transferring direction. Consequently, it is difficult to accurately stop a flow of a liquid by a capillary force in the capillary cavity 19. However, configuring the portion described above as in a sixth embodiment illustrated in FIGS. 30 and 31, a flow of a liquid by a capillary force can be stopped accurately.

Figure 30:
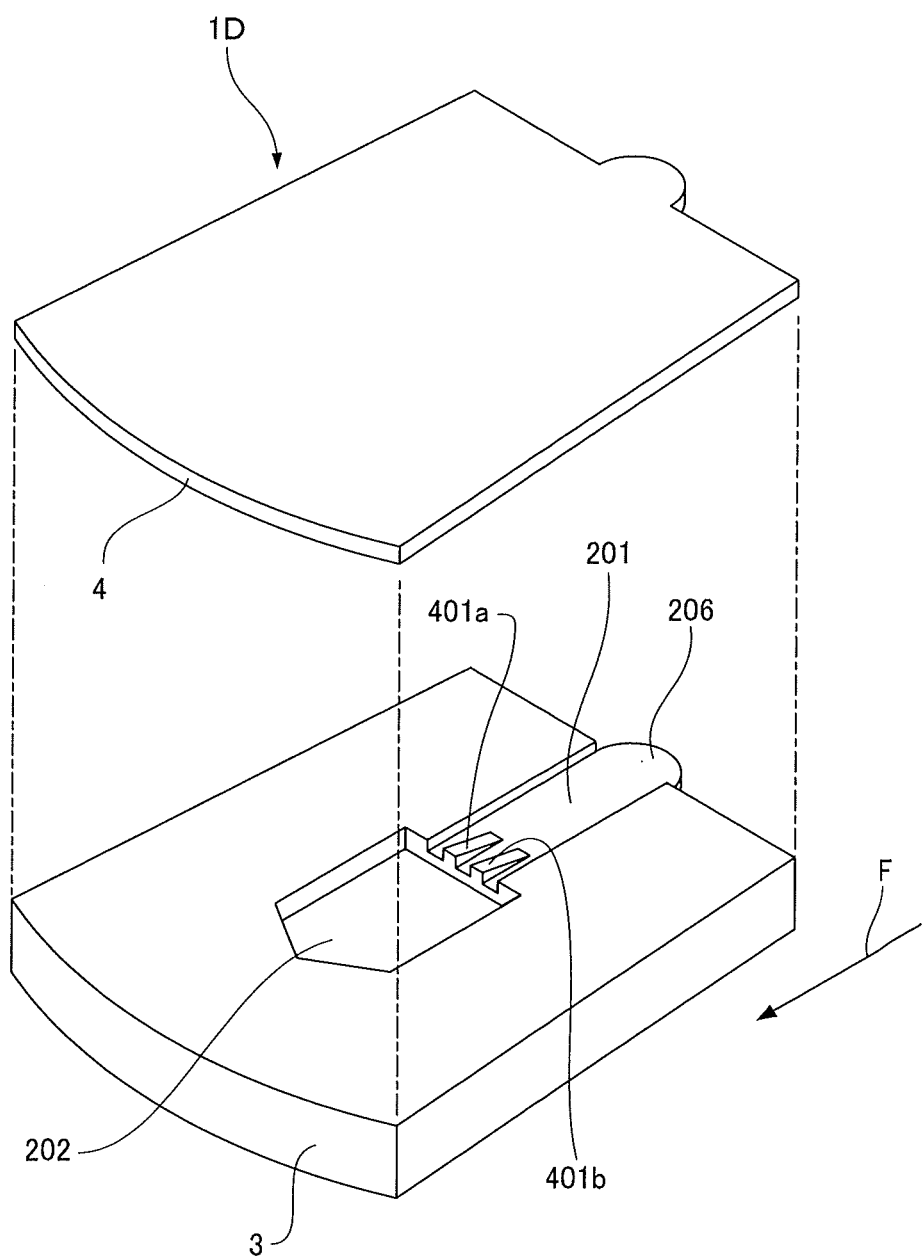
FIG. 30 is an exploded perspective view of an analyzing device according to the present invention.

FIG. 30 is an exploded enlarged view of an analyzing device 1D according to the present invention. FIGS. 31(a), 31(b), and 31(c) are, respectively, a plan view and a cross-sectional view of the analyzing device 1D according to the present invention, and a front view of the analyzing device 1D according to the present invention as seen from an inlet 206a.

The analyzing device 1D is made up of a base substrate 3 having a thickness of 0.1 mm to 7 mm and on which a recess is formed, and a cover substrate 4 having a thickness of 1 mm to 7 mm to be bonded to the base substrate 3. For example, both the base substrate 3 and the cover substrate 4 are made from a transparent base material.

A microchannel 203 is formed between the base substrate 3 and the cover substrate 4 bonded together with an adhesive. The microchannel 203 includes: a sample measuring section 201 made up of a capillary channel and which quantitatively measures a fixed amount of a sample liquid to be analyzed; and a receiving section 202 connected to the sample measuring section 201 and which accepts the fixed amount of the sample liquid measured by the sample measuring section 201 and causes a reaction with a reagent. Specifically, a reagent is contained in the receiving section 202 so that a reaction immediately occurs once the sample liquid is transferred to the receiving section 202. The reagent may either be a solid reagent or a reagent applied to a wall face. For example, glucose oxidase or glucose dehydrogenase for glucose measurement, cholesterol esterase or cholesterol hydrogenase for cholesterol measurement, and the like may be used as the reagent.

The inlet 206a is formed on a sample collecting section 206 on one end of the sample measuring section 201. Another end of the sample measuring section 201 is connected to the receiving section 202. The sample collecting section 206 is formed so as to have an arc-like shape with a width Wc as its diameter.

Although an external shape of the analyzing device 1D differs from the external shapes of the analyzing devices 1, 1A, 1B, and 1C according to the respective embodiments described above, in the present embodiment, the shape of a boundary between the sample measuring section 201 and the receiving section 202 has been creatively designed in order to prevent more than a required amount of a sample liquid from entering the receiving section 202 from the sample measuring section 201. The sample collecting section 206 corresponds to the inlet 13 according to the respective embodiments described above. The sample measuring section 201 corresponds to the capillary cavity 19, and the receiving section 202 to the separation cavity 23.

The sample measuring section 201 is made up of: a capillary channel primary segment 207a with a gap that is uniform in a direction towards the receiving section 202 from the sample collecting section 206 (direction depicted by arrow F); and a connected section 207b between the receiving section 202 and a trailing end position P1 of the primary segment 207a.

More specifically, in a capillary channel whose gap dimension is the same as the primary segment 207a at the connected section 207b of the sample measuring section 201, partition walls 401a and 401b that split the channel in a width direction are formed at an interval in the width direction of the channel.

The partition walls 401a and 401b are formed in a slope that rises towards the receiving section 202. The heights of the partition walls 401a and 401b at a connected plane of the sample measuring section 201 and the receiving section 202 are equal to the gap of the capillary channel of the sample measuring section 201.

Figure 31:
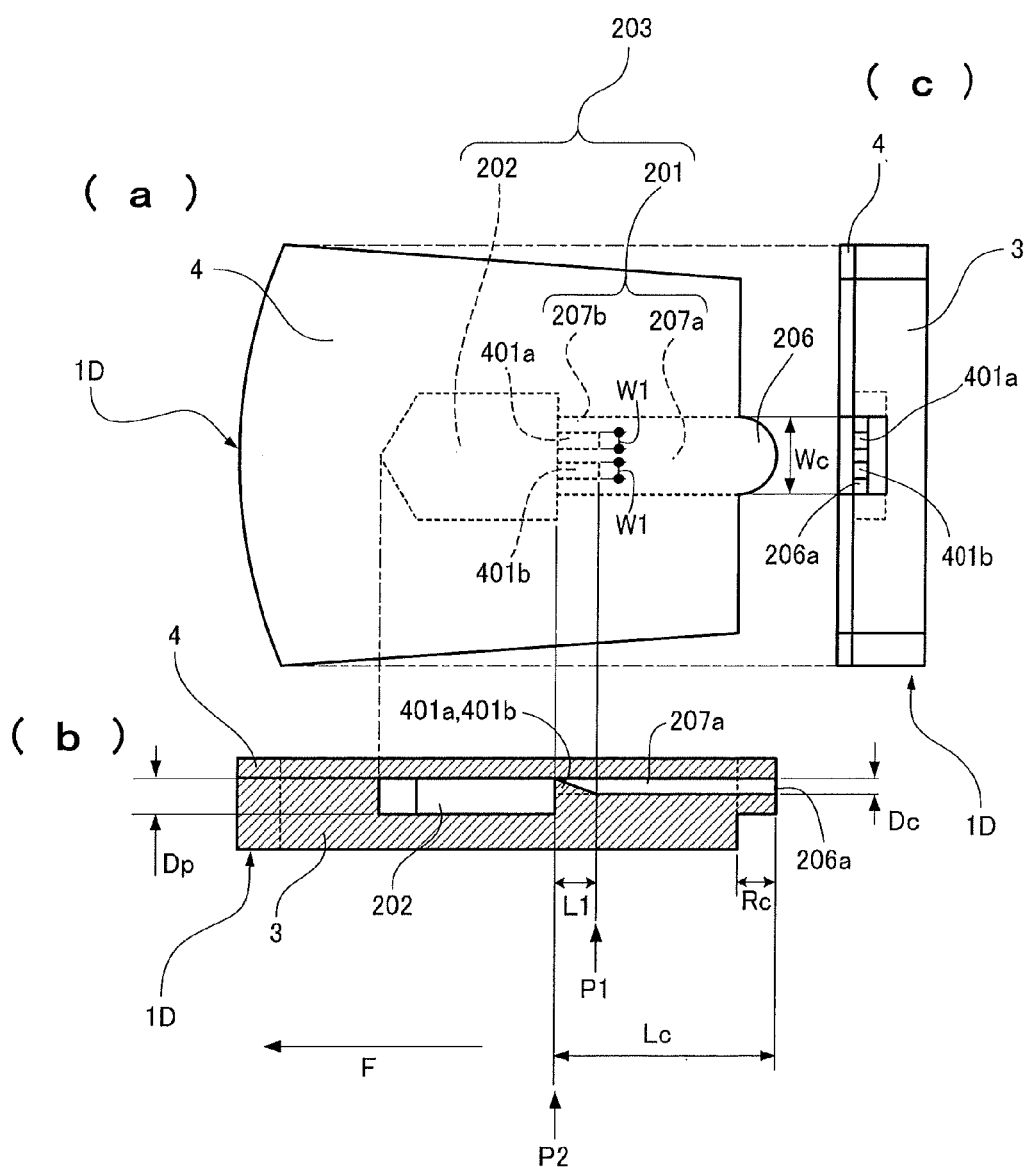
FIG. 31 is a plan view, a cross-sectional view, and a front view of the fourth embodiment of the present invention.

In FIG. 31, a length of the sample measuring section 201 is denoted as Lc, the gap of the capillary channel of the sample measuring section 201 as Dc, a width of the inlet 206a as Wc, a length of the sample collecting section 206 as Rc, and a length of the connected section 207b as L. A gap of the receiving section 202 is uniform in the direction depicted by arrow F and is denoted as Dp. W1 denotes a width and L1 denotes a length of the partition walls 401a and 401b.

A part of or all of wall faces of the base substrate 3 and the cover substrate 4 have been subjected to hydrophilic treatment in order to reduce viscous resistance within the microchannel 203 and promote fluid movement. Specifically, any of a bottom (the side of the base substrate 3) or a ceiling (the side of the cover substrate 4) of the sample measuring section 201 and the receiving section 202 is formed by a continuous plane subjected to hydrophilic treatment. The partition walls 401a and 401b have also been subjected to hydrophilic treatment.

In this case, hydrophilicity refers to a contact angle of less than 90 degrees with respect to water, and more favorably, a contact angle of less than 40 degrees. Specifically, methods of such hydrophilic treatment include a surface treatment method using plasma, corona, ozone, or an active gas such as fluorine, and surface treatment with a surfactant.

Alternatively, a hydrophilic material such as glass may be used for at least one of the base substrate 3 and the cover substrate 4, or a hydrophilizing agent such as a surfactant, a hydrophilic polymer, and a hydrophilic powder such as a silica gel may be added when molding at least one of the base substrate 3 and the cover substrate 4 so as to impart a material surface with hydrophilicity.

Figure 32:
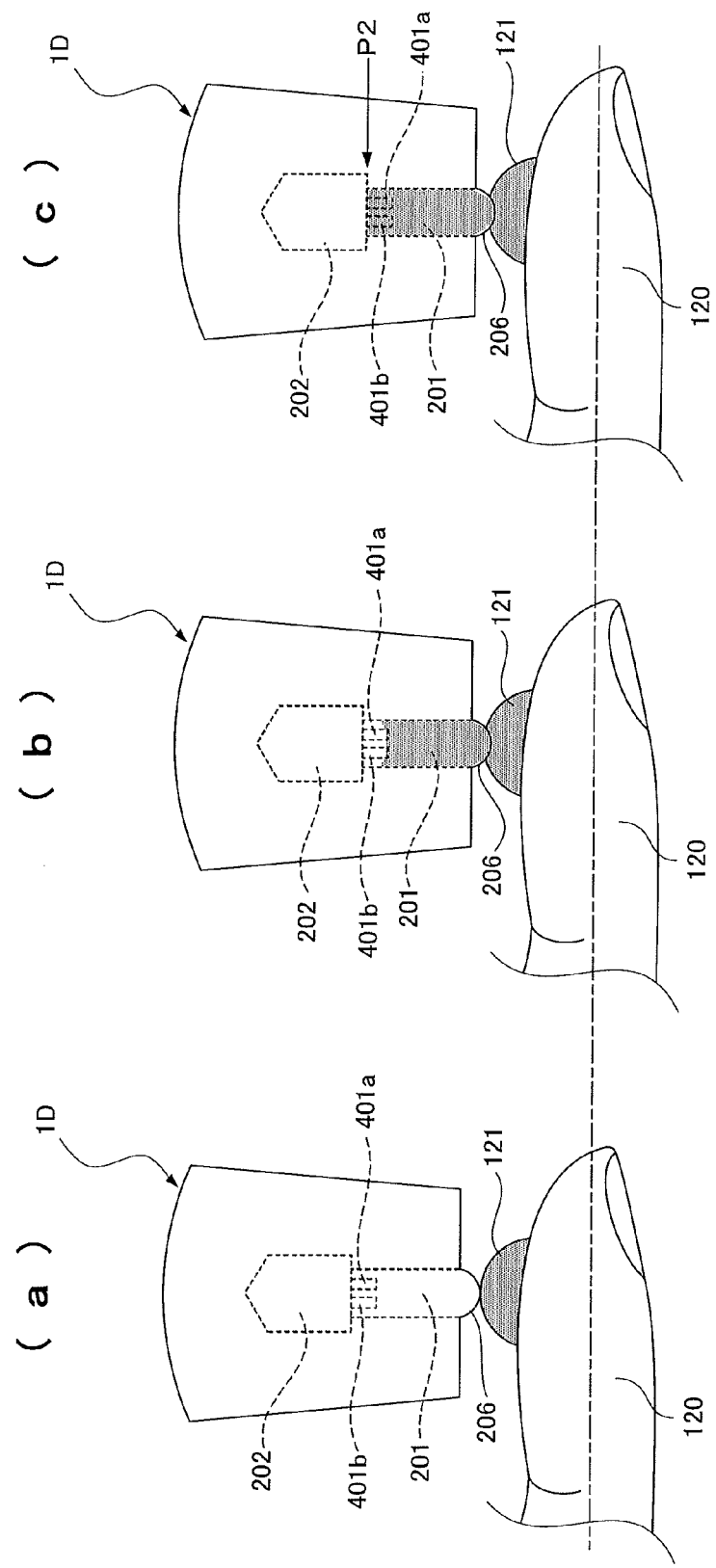
FIG. 32 is an explanatory diagram of a sample liquid collection process according to the fourth embodiment of the present invention.

A process in which a sample liquid is collected in the analyzing device 1D created as described above and a fixed amount is measured is illustrated in FIGS. 32(a) to 32(c).

In FIG. 32(a), first, a fingertip 120 of a testee is pierced by a needle using a blood-collecting puncture device or the like to create a blood drop. A sample collecting section 206 on a leading end of the sample measuring section 201 is brought into contact with the blood drop. Generally, a capillary force acts when a part of or all of wall faces are hydrophilic and a distance between wall faces facing each other is equal to or less than 1 mm. Furthermore, when the distance is equal to or less than 0.3 mm, the capillary force becomes dominant with respect to surface energy acting on a sample liquid and on the wall faces, and suction of blood in the blood drop 121 into a capillary channel of the sample measuring section 201 commences without having to apply an external force.

Next, as illustrated in FIG. 32(b), blood is suctioned by a capillary force and, as illustrated in FIG. 32(c), blood fills up to a coupled section P2 of the sample measuring section 201 and the receiving section 202. At this point, the suctioned blood fills a gap of the sample measuring section 201 split by the partition walls 401a and 401b and stops at the coupled section of the sample measuring section 201 and the receiving section 202.

This occurs because a part of a wall face that has been continuous in a flowing direction of the sample liquid is severed by a face of the coupled section of the sample measuring section 201 and the receiving section 202, resulting in a decrease in a wet interfacial tension due to the sample liquid flowing in a direction of the receiving section 202 and breaking the capillary force that had been previously dominant.

Moreover, by providing two partition walls 401a and 401b formed from a face where the sample measuring section 201 and the receiving section 202 are coupled towards the inside of the sample measuring section 201, an interface of the sample liquid filling the sample measuring section 201 becomes continuous at the coupled section of the sample measuring section 201 and the receiving section 202. In addition, by reducing a rate of contact with wall faces subjected to hydrophilic treatment, a surface tension of the sample liquid can be arranged so as to exceed a wet interfacial tension from the sample measuring section 201 towards the receiving section 202. As a result, an overflow amount of the sample liquid into the receiving section 202 can be suppressed.

An effect of the present sixth embodiment will now be described based on specific dimensions.

When causing a reaction between a sample liquid and a reagent disposed in the receiving section 202 to measure absorbance, 10 µL of the sample liquid must be collected at the sample measuring section 201. In addition, for the purpose of improving analytical precision, it is required that quantitative variance at the sample measuring section 201 be kept to within ±5% or, in other words, 9.5 to 10.5 µL of the sample liquid must be collected. In consideration thereof, the shape of the sample measuring section 201 is set such that: length Lc=5.0 mm; width Wc=5.0 mm; and thickness Dc=0.3 mm. In addition, the partition walls 401a and 401b are given a sloped shape whose width W1=0.6 mm and length L1=1 mm and are designed to split a portion between the coupled section of the sample measuring section 201 and the receiving section 202 and a position 1 mm towards the inside of the sample measuring section 201 into three equal parts.

Figure 33:
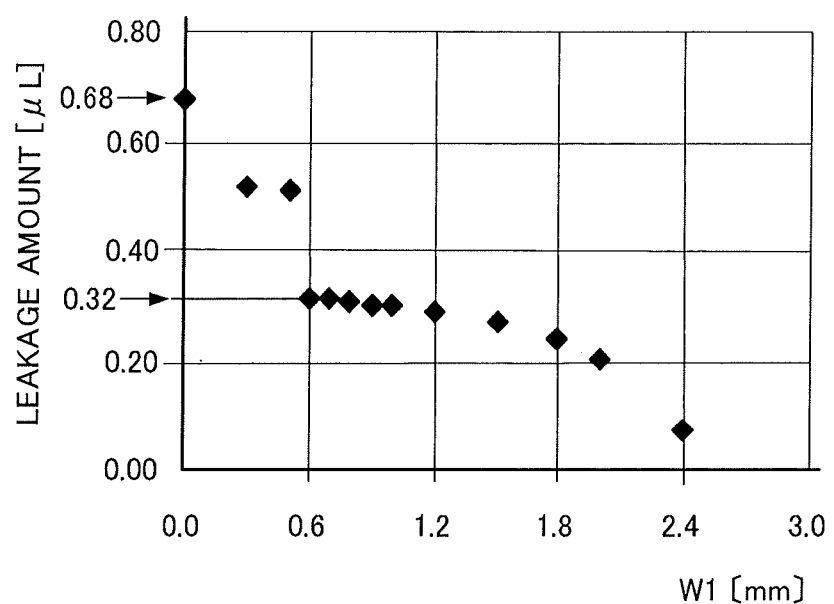
FIG. 33 is a relationship diagram between a sample liquid that overflows into a receiving section and a shape of an inclined face according to the fourth embodiment of the present invention.

A relationship in this case between the width W1 of the partition walls 401a and 401b of the coupled section of the sample measuring section 201 and the receiving section 202 and an overflow amount of a sample liquid that overflows into the receiving section 202 is illustrated in FIG. 33.

It is shown that when the width W1 of the partition walls 401a and 401b is set such that W1=0.6 mm, the overflow amount is 0.32 µL. It is also shown that the overflow amount to the receiving section 202 can be suppressed by increasing the width W1 of the partition walls 401a and 401b. In a case where the partition walls 401a and 401b do not exist (W1=0), the overflow amount of the sample liquid to the receiving section 202 is 0.68 µL.

These results indicate that by disposing the partition walls 401a and 401b at the coupled section of the sample measuring section 201 and the receiving section 202, control reliability of a sample liquid at the coupled section of the sample measuring section 201 and the receiving section 202 can be improved and the sample liquid can be accurately measured. Collection of blood measured by the sample measuring section 201 is completed in this state to enable a sample liquid to be analyzed with high accuracy.

In the embodiment described above, while two partition walls 401a and 401b have been formed in a capillary channel of the connected section 207b of the sample measuring section 201 and the receiving section 202, even when the number of partition walls splitting the channel in a width direction is one or three or more, a reduction in the overflow amount of a sample liquid to the receiving section 202 has been confirmed in comparison to a case where no partition walls are provided (W1=0).

Seventh Embodiment

Figure 34:
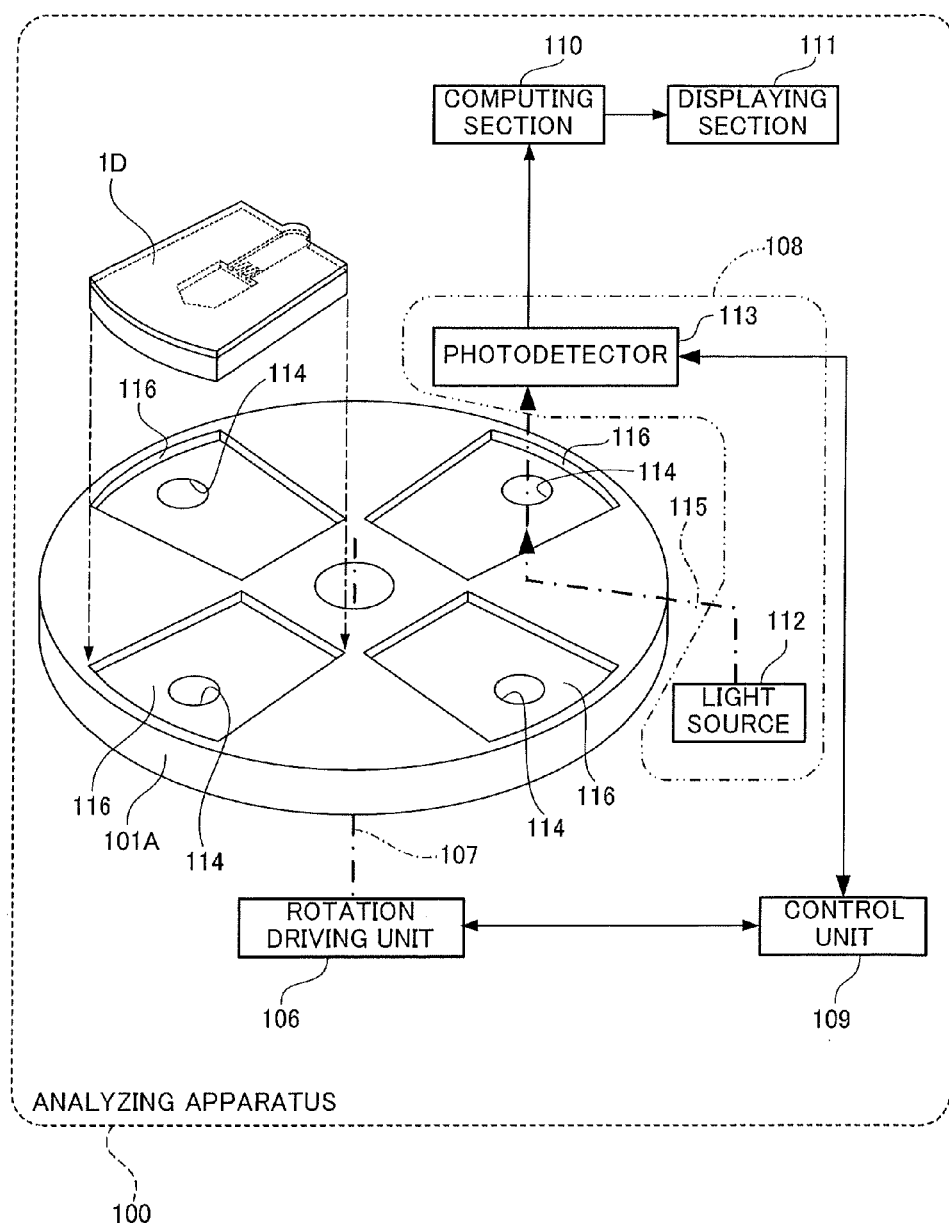
FIG. 34 is a configuration diagram of an analyzing apparatus according to the present invention.
Figure 35:
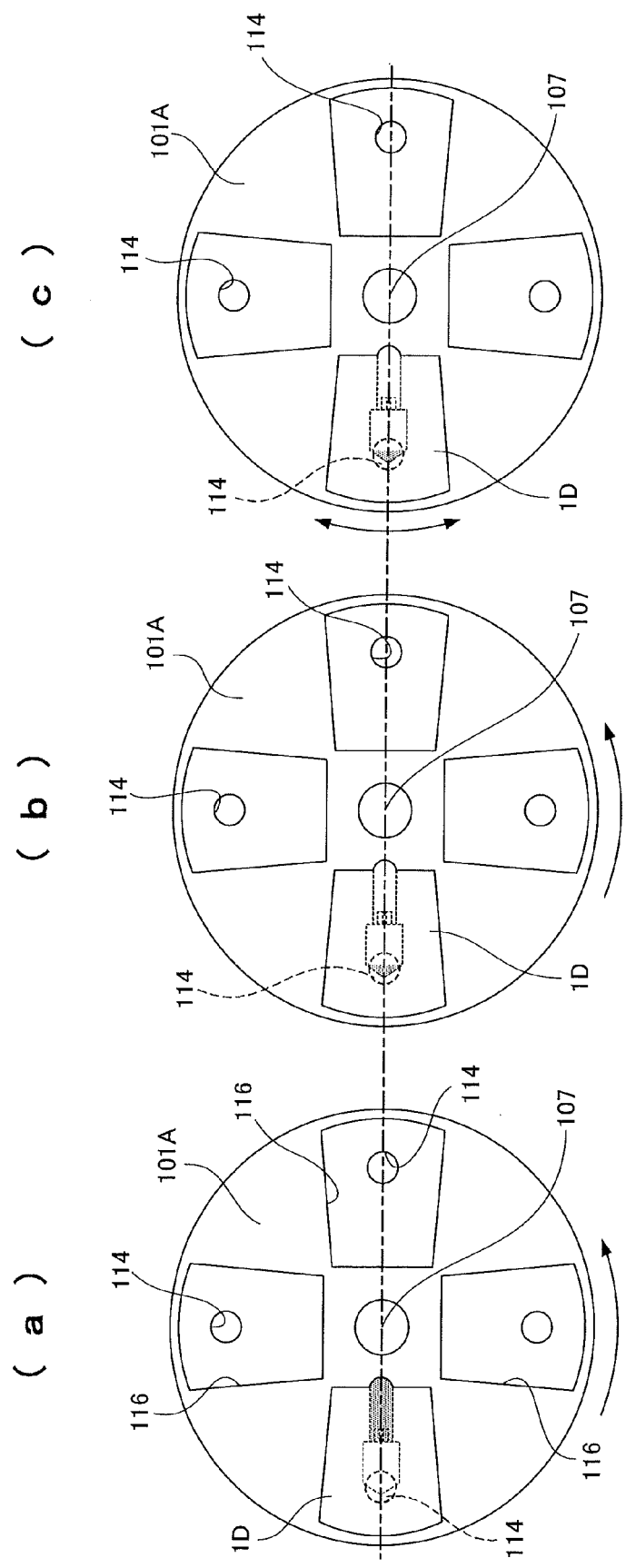
FIG. 35 is an explanatory diagram of a sample liquid transfer process according to the fourth embodiment of the present invention.
Figure 36:
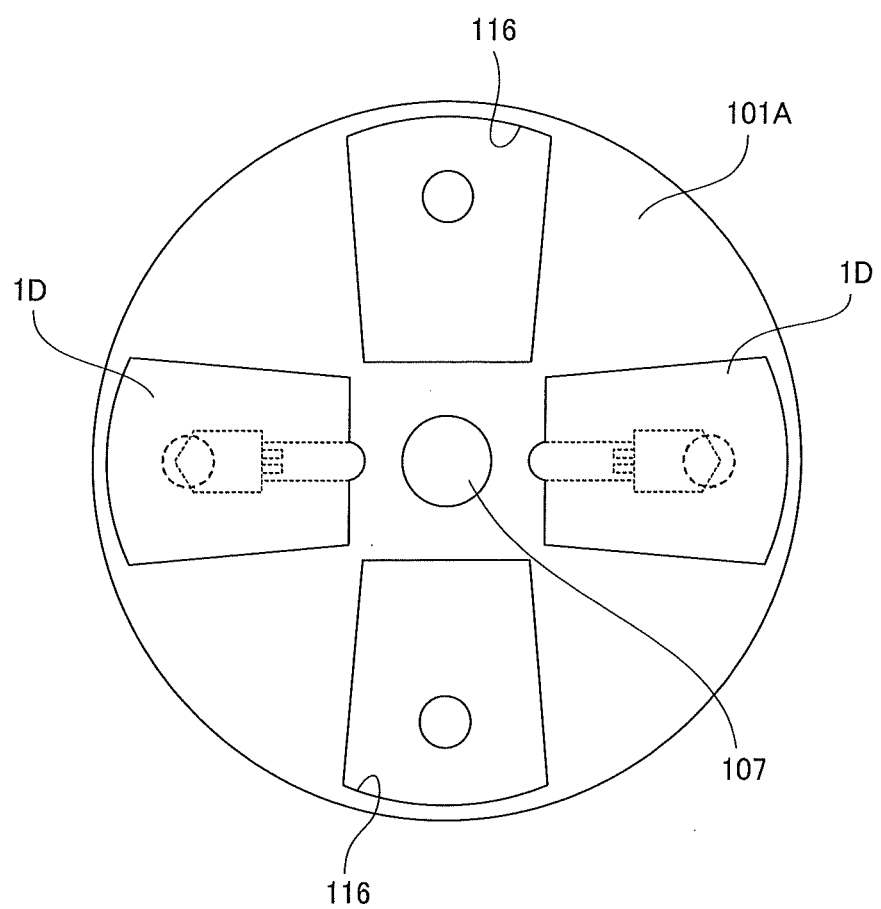
FIG. 36 is a plan view illustrating a case where two analyzing devices are set on a rotor.

FIGS. 34 to 36 illustrate an analyzing apparatus 100 according to the present invention which uses the analyzing device 1D according to the sixth embodiment.

The analyzing apparatus is configured as illustrated in FIG. 34.

A recess 116 on which is set the analyzing device 1D having collected a sample liquid is formed on a disk-like rotor 101A to be rotationally driven around a rotation axial center 107 by a rotation driving unit 106 that is a motor or the like. A penetrating hole 114 is provided in the recess 116 in correspondence to a position of a receiving section 202 of the set analyzing device 1D.

An optical measurement unit 108 that accesses the receiving section 202 of the analyzing device 1D set on the rotor 101A is made up of a light source 112 and a photodetector 113 disposed with the rotor 101A in-between so as to be able to receive light that passes through the hole 114 of the rotor 101A.

A control unit 109 controls a rotational speed and a rotational direction of the rotor 101A, a measurement timing of the optical measurement unit 108, and the like. More specifically, in addition to controlling the rotation driving unit 106 so as to rotate the analyzing device 1D around the rotation axial center 107 via the rotor 101A in any direction at a predetermined rotational speed, the control unit 109 is arranged so as to be capable of causing the analyzing device 1D to perform a left-right reciprocating movement centered around the rotation axial center 107 at a predetermined stop position and at a predetermined amplitude range and a predetermined frequency so as to swing the analyzing device 1D.

A detection light 115 outputted from the light source 112 is transmitted through the hole 114 of the rotor 101A and through a reactant in the receiving section 202 of the set analyzing device 1D, and is received by the photodetector 113 and inputted to a computing section 110. The computing section 110 analyzes characteristics of the sample liquid from an absorption measurement result and displays the characteristics on a displaying section 111.

A centrifugal transfer process and a reagent reaction process of the sample liquid measured by a sample measuring section 201 will be described with reference to FIG. 35.

After setting and fixing the analyzing device 1D whose sample measuring section 201 has been filled with a sample liquid onto the recess 116 of the rotor 101A, by rotating the rotor 101A in a direction depicted by an arrow as illustrated in FIG. 35(a), a centrifugal force is generated on the sample liquid filling the sample measuring section 201 of the analyzing device 1D. As a result, a sample liquid that has previously been stationary at the connected section 207b begins to move towards the receiving section 202. Furthermore, by maintaining a constant number of revolutions, as illustrated in FIG. 35(b), an entirety of a sample liquid measured by the sample measuring section 201 moves to the receiving section 202.

The rotor 101A is swingingly moved so as to accelerate a reaction with a reagent. The swinging operation is performed by repetitively changing rotational directions of the rotor 101A. Specifically, by swingingly moving clockwise and counter-clockwise respectively over ±1 degrees in a state where the microchannel 203 of the analyzing device 1D is oriented in a nine o'clock direction as illustrated in FIG. 35(c), the sample liquid and the reagent moved to the receiving section 202 are agitated and a reaction liquid can be eventually created inside the receiving section 202. As for an angle and a frequency of the swinging movement in this case, ±1 degrees or greater and 22 Hz or greater respectively suffice. By performing a swinging movement satisfying these conditions, a reliable reaction with a reagent can be carried out in a short period of time. In other words, by swingingly moving the analyzing device 1D at a frequency of around 22 Hz and over a minute angle, a sample liquid and a reagent can be reliably mixed.

The analyzing apparatus 100 processes a result of an absorbance measurement by the optical measurement unit 108 with the computing section 110 and displays an analysis result of characteristics of the sample liquid on the displaying section 111.

As shown, since the control unit 109 instructs the rotation driving unit 106 to swingingly move the analyzing device 1D via the rotor 101A, the sample liquid can be analyzed with extremely high accuracy.

FIG. 36 illustrates an analyzing apparatus in operation with two analyzing devices 1D set on the rotor 101A.

Eighth Embodiment

The gap between the base substrate 3 and the cover substrate 4 at the portion of the capillary cavity 19 illustrated in FIG. 10B is constant in a blood-transferring direction. In addition, the gap between the base substrate 3 and the cover substrate 4 at the boundary between the capillary cavity 19 and the separation cavity 23 is constant in a direction perpendicular to the blood-transferring direction. Consequently, it is difficult to accurately stop a flow of a liquid by a capillary force in the capillary cavity 19. However, configuring the portion described above as in an eighth embodiment illustrated in FIGS. 37 and 38, a flow of a liquid by a capillary force can be stopped accurately.

Figure 37:
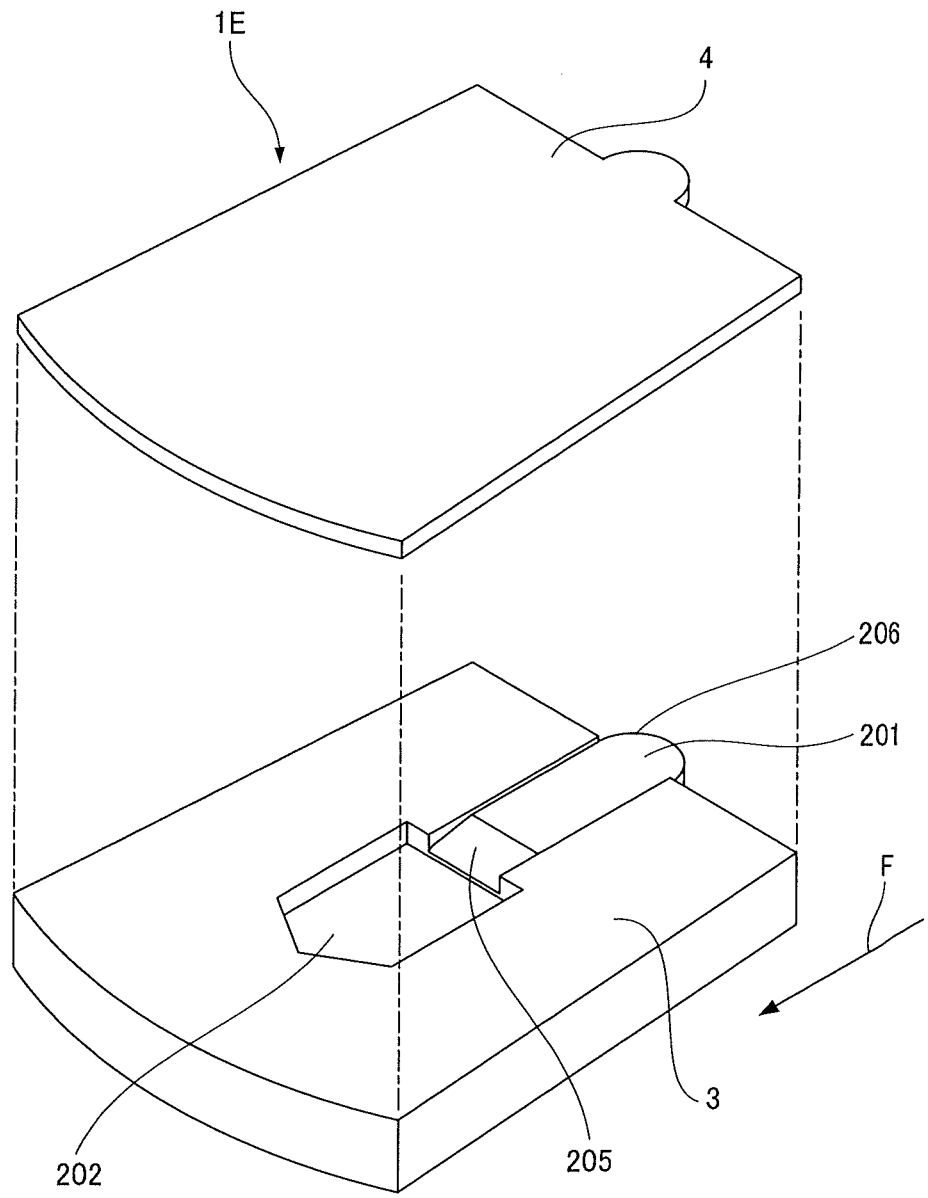
FIG. 37 is an exploded perspective view of an analyzing device according to an eighth embodiment of the present invention.

FIG. 37 is an exploded enlarged view of an analyzing device 1E according to the present invention. FIGS. 38(a), 38(b), and 38(c) are, respectively, a plan view and a cross-sectional view of the analyzing device 1E according to the present invention, and a front view of the analyzing device 1E according to the present invention as seen from an inlet 206a.

The analyzing device 1E is made up of a base substrate 3 having a thickness of 1 mm to 7 mm and on which a recess is formed and a cover substrate 4 having a thickness of 1 mm to 7 mm to be bonded to the base substrate 3. For example, both the base substrate 3 and the cover substrate 4 are made from a transparent base material.

A microchannel 203 is formed between the base substrate 3 and the cover substrate 4 bonded together with an adhesive. The microchannel 203 includes: a sample measuring section 201 made up of a capillary channel and which quantitatively measures a fixed amount of a sample liquid to be analyzed; and a receiving section 202 connected to the sample measuring section 201 and which accepts the fixed amount of the sample liquid measured by the sample measuring section 201 and causes a reaction with a reagent. Specifically, a reagent is contained in the receiving section 202 so that a reaction immediately occurs once the sample liquid is transferred to the receiving section 202. The reagent may either be a solid reagent or a reagent applied to a wall face. For example, glucose oxidase or glucose dehydrogenase for glucose measurement, cholesterol esterase or cholesterol hydrogenase for cholesterol measurement, and the like may be used as the reagent.

The inlet 206a is formed on a sample collecting section 206 on one end of the sample measuring section 201. Another end of the sample measuring section 201 is connected to the receiving section 202. The sample collecting section 206 is formed so as to have an arc-like shape with a width Wc as its diameter.

The sample measuring section 201 is made up of: a capillary channel primary segment 207a with a gap that is uniform in a direction towards the receiving section 202 from the sample collecting section 206 (direction depicted by arrow F); and a connected section 207b between the receiving section 202 and a trailing end position P1 of the primary segment 207a. More specifically, the connected section 207b of the sample measuring section 201 is molded as an inclined face 205 whose bottom face is an elliptical arc of a recess of the base substrate 3. A capillary channel is widely configured towards the receiving section 202.

Figure 38:
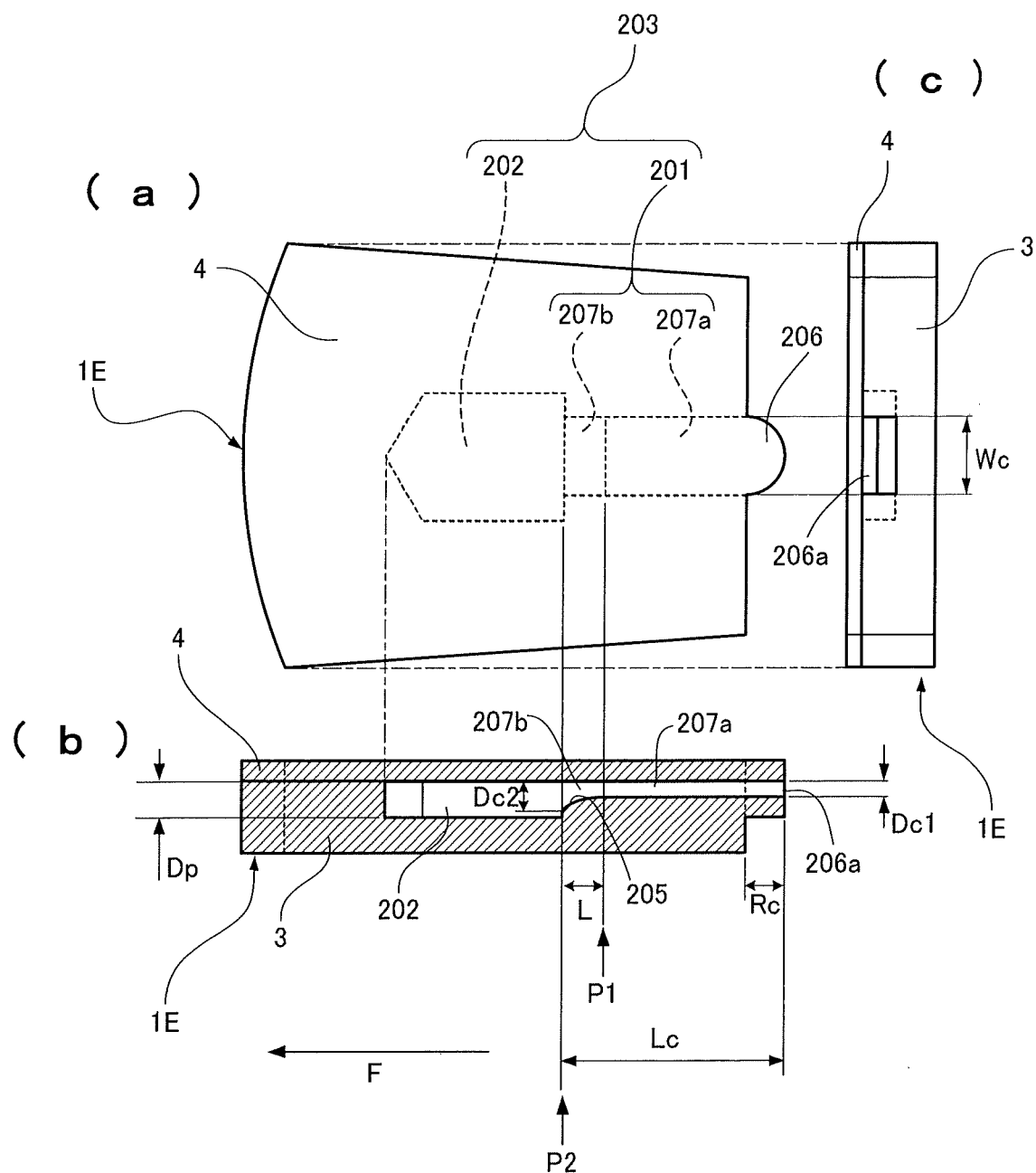
FIG. 38 is a plan view, a cross-sectional view, and a front view of the eighth embodiment of the present invention.

In FIG. 38, a length of the sample measuring section 201 is denoted as Lc, the gap of the sample measuring section 201 on a side of the inlet 206a as Dc1, a width of the inlet 206a as Wc, a length of the sample collecting section 206 as Rc, a gap of a connected plane (a trailing end position of the inclined face 205) P2 of the sample measuring section 201 and the receiving section 202 as Dc2, and a length of the connected section 207b as L. A gap of the receiving section 202 is uniform in the direction depicted by an arrow F and is denoted as Dp. In addition, a height (=Dc2) of the sample measuring section 201 from the cover substrate 4 and a height (=Dp) of the receiving section 202 from the cover substrate 4 at the connected plane P2 of the sample measuring section 201 and the receiving section 202 are molded such that "Dc2<Dp".

A part of or all of wall faces of the base substrate 3 and the cover substrate 4 have been subjected to hydrophilic treatment in order to reduce viscous resistance within the microchannel 203 and promote fluid movement. Specifically, any of a bottom (the side of the base substrate 3) or a ceiling (the side of the cover substrate 4) of the sample measuring section 201 and the receiving section 202 is formed by a continuous plane subjected to hydrophilic treatment.

In this case, hydrophilicity refers to a contact angle of less than 90 degrees with respect to water, and more favorably, a contact angle of less than 40 degrees. Specifically, methods of such hydrophilic treatment include a surface treatment method using plasma, corona, ozone, or an active gas such as fluorine, and surface treatment with a surfactant. Alternatively, a hydrophilic material such as glass may be used for at least one of the base substrate 3 and the cover substrate 4, or a hydrophilizing agent such as a surfactant, a hydrophilic polymer, and a hydrophilic powder such as a silica gel may be added when molding at least one of the base substrate 3 and the cover substrate 4 so as to impart a material surface with hydrophilicity.

Figure 39:
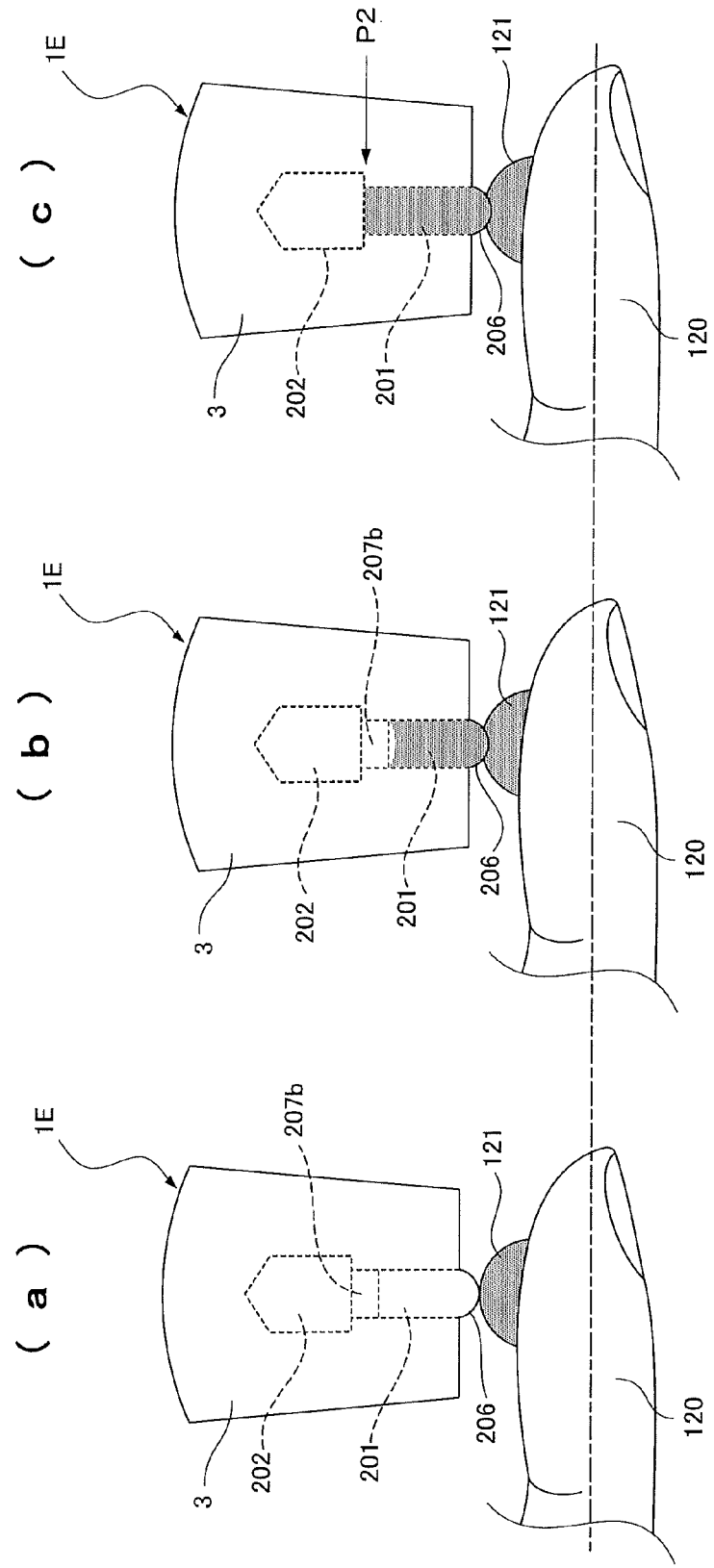
FIG. 39 is an explanatory diagram of a sample liquid collection process according to the eighth embodiment of the present invention.

A process in which a sample liquid is collected in the analyzing device 1E created as described above and a fixed amount is measured is illustrated in FIGS. 39(a) to 39(c).

In FIG. 39(a), first, a fingertip 120 is pierced by a needle using a blood-collecting puncture device or the like to create a blood drop. A sample collecting section 206 on a leading end of the sample measuring section 201 is brought into contact with the blood drop. Generally, capillary force acts when a part of or all of wall faces are hydrophilic and a distance between wall faces facing each other is equal to or less than 1 mm. Furthermore, when the distance is equal to or less than 0.3 mm, the capillary force becomes dominant with respect to surface energy acting on a sample liquid and the wall faces, and suction of blood to become a sample liquid into a capillary channel of the sample measuring section 201 commences without having to apply an external force.

Next, as illustrated in FIG. 39(b), the sample liquid is suctioned by a capillary force acting in the sample measuring section 201 and fills the sample measuring section 201 up to a leading end position P1 of the inclined face 205 and becomes stationary.

This occurs because a part of a wall face of the sample measuring section 201 which has been continuous in a flowing direction of the sample liquid is severed by the inclined face 205, resulting in a decrease in a wet interfacial tension component due to the sample liquid flowing in a direction of the receiving section 202 and breaking the capillary force that had been previously dominant. Furthermore, as illustrated in FIG. 39(c), when the sample liquid is suctioned by the connected section 207b and a cross-sectional area of the sample liquid at the connected plane (the terminal end position of the inclined face 205) P2 of the sample measuring section 201 and the receiving section 202 becomes maximum, a force that returns the sample liquid into the sample measuring section 201 is generated by a surface tension acting on an interface of the sample liquid. As a result, an overflow amount of the sample liquid into the receiving section 202 can be suppressed.

Moreover, in the present embodiment, a face of the microchannel 203 which opposes the inclined face 205 is either made of a hydrophilic material or has been subjected to hydrophilic treatment for imparting hydrophilicity.

An effect of the present eighth embodiment will now be described based on specific dimensions.

At the receiving section 202 of the analyzing device 1E, when causing a reaction between the sample liquid and a reagent disposed in the receiving section 202 to measure absorbance, 10 μL of the sample liquid must be collected at the sample measuring section 201. In addition, for the purpose of improving analytical precision, it is required that quantitative variance at the sample measuring section 201 be kept to within ±5% or, in other words, 9.5 to 10.5 μL of the sample liquid must be collected. In this case, the shape of the sample measuring section 201 is set such that: Lc=9.8 mm; Wc=4.0 mm; and Dc=0.3 mm. Furthermore, in regards to the inclined face 205 of the connected section 207b, as illustrated in FIG. 40(b), an incline is formed so as to become a part of an elliptical arc in which L=1.0 and minor axis: Dc2−Dc1=0.3 mm.

Figure 41:
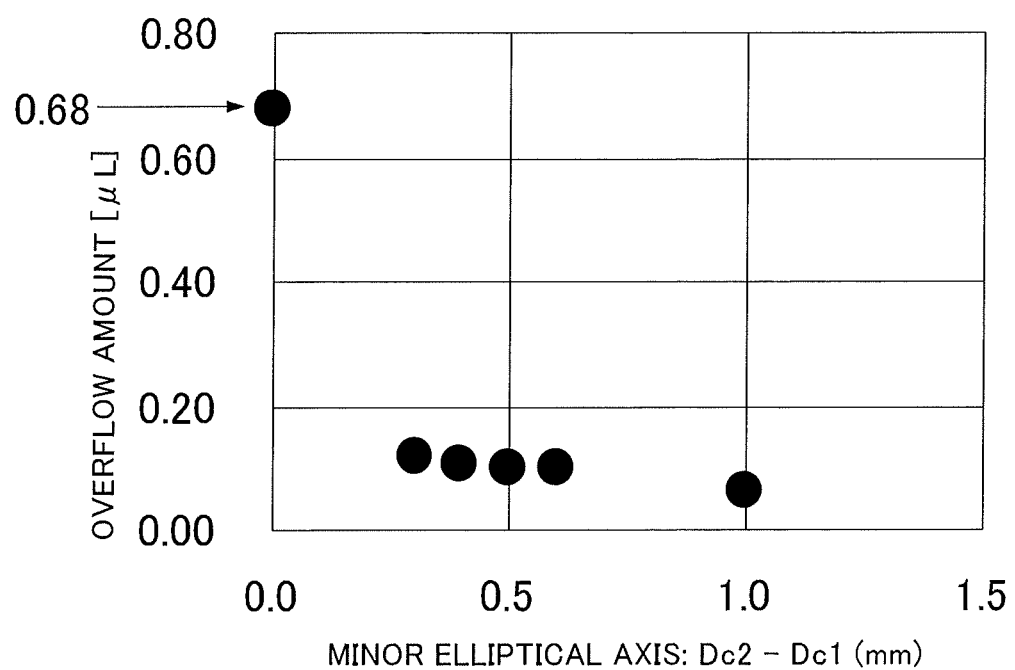
FIG. 41 is a relationship diagram between a sample liquid that overflows into a receiving section and a shape of an inclined face according to the eighth embodiment of the present invention.

As a result, the amount of sample fluid overflowing to the receiving section 202 is 0.12 μL, sufficiently satisfying the ±5% quantitative variance for a sample liquid. A relationship between the elliptic arc shape of the inclined face 205 disposed in the sample measuring section 201 and an overflow amount of the sample liquid that overflows into the receiving section 202 is illustrated in FIG. 41.

A major axis L of the elliptical arc is set such that L1=1.0 mm while the length of the minor axis Dc2−Dc1 is varied. For example, it is shown that while the overflow amount of the sample liquid into the receiving section 202 is 0.68 μL in a case where the inclined face 205 has not been provided, by disposing the inclined face 205, the overflow amount of the sample liquid into the receiving section 202 is reduced to 0.2 μL or less. It is also shown that the overflow amount into the receiving section 202 can be suppressed by increasing the minor axis: Dc2−Dc1 of the elliptical arc.

From the results described above, by disposing the inclined face 205 at the connected section 207b of the sample measuring section 201 and the receiving section 202, measurement of a sample liquid can be accurately performed solely by the shape of the sample measuring section 201. Collection of a sample liquid measured by the sample measuring section 201 is completed in this state to enable the sample liquid to be analyzed with high accuracy.

The shape of the inclined face 205 may be a part of an arc with a radius of L as illustrated in FIG. 40(a) or a part of an elliptical arc with a major axis of L and a minor axis of Dc2−Dc1 as illustrated in FIG. 40(b). However, the shape of the inclined face 205 need not be limited to an elliptical arc or an arc as long as the inclined face 205 of the connected section 207b and a bottom face of the primary segment 207a are continuously formed, and may be a straight inclined face.

Ninth Embodiment

Figure 42:
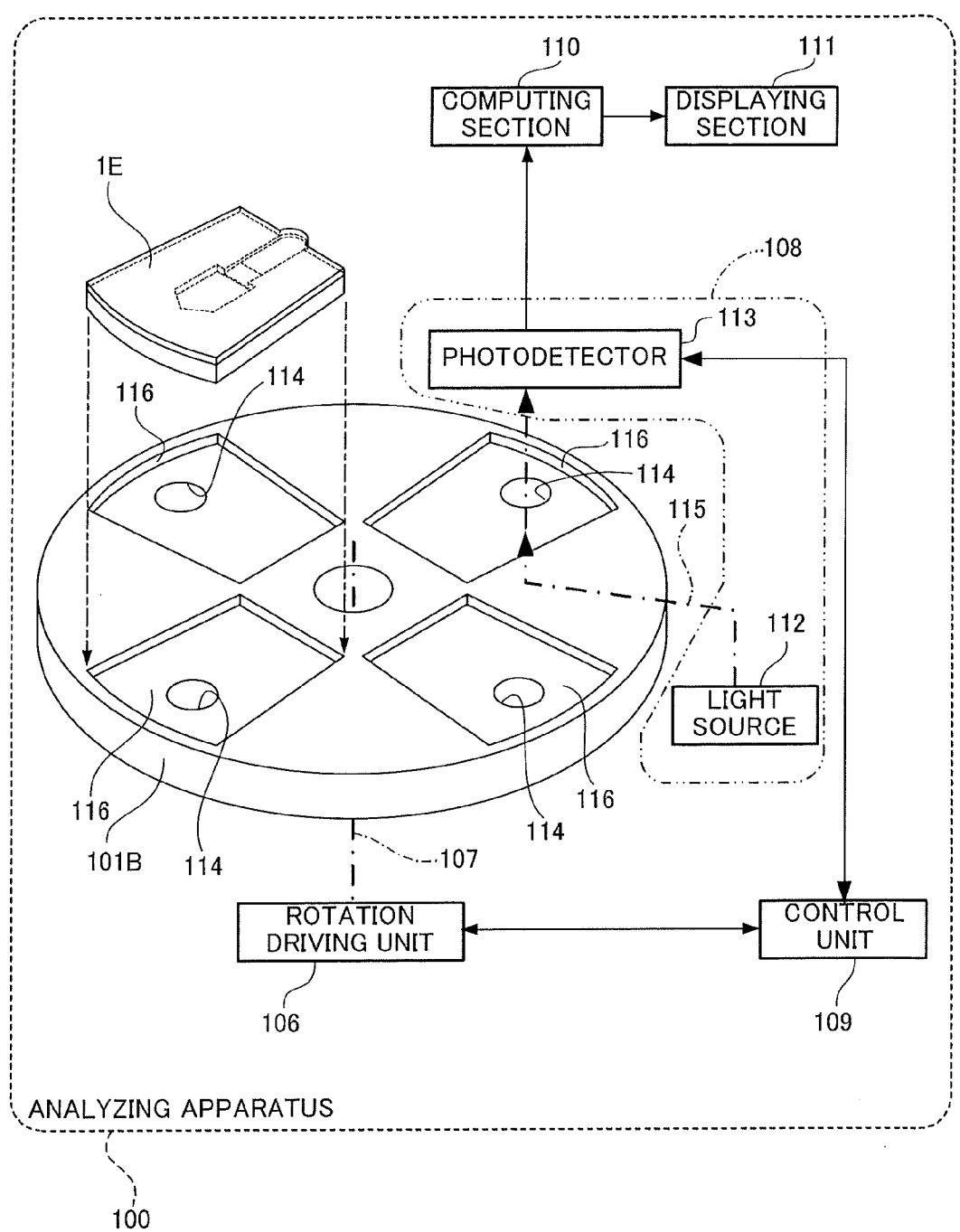
FIG. 42 is a configuration diagram of an analyzing apparatus according to a ninth embodiment of the present invention.
Figure 43:
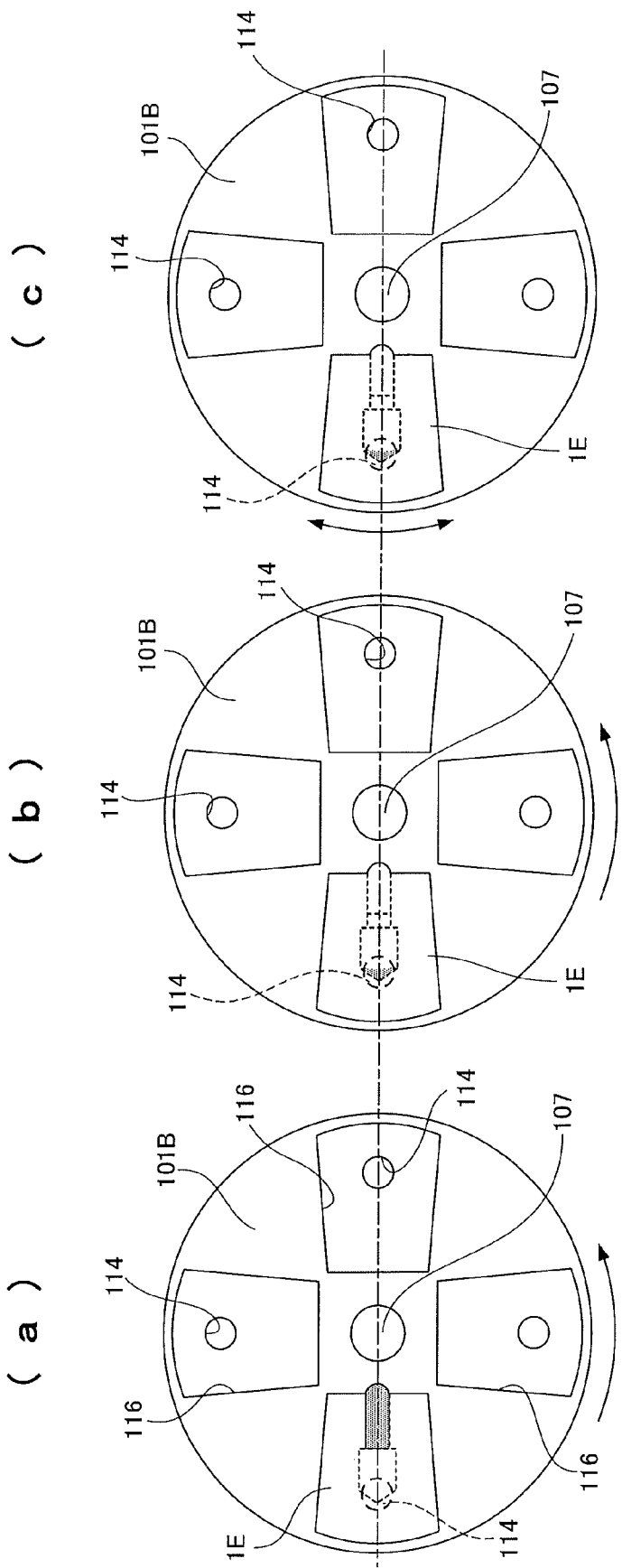
FIG. 43 is an explanatory diagram of a sample liquid transfer process according to the ninth embodiment of the present invention.
Figure 44:
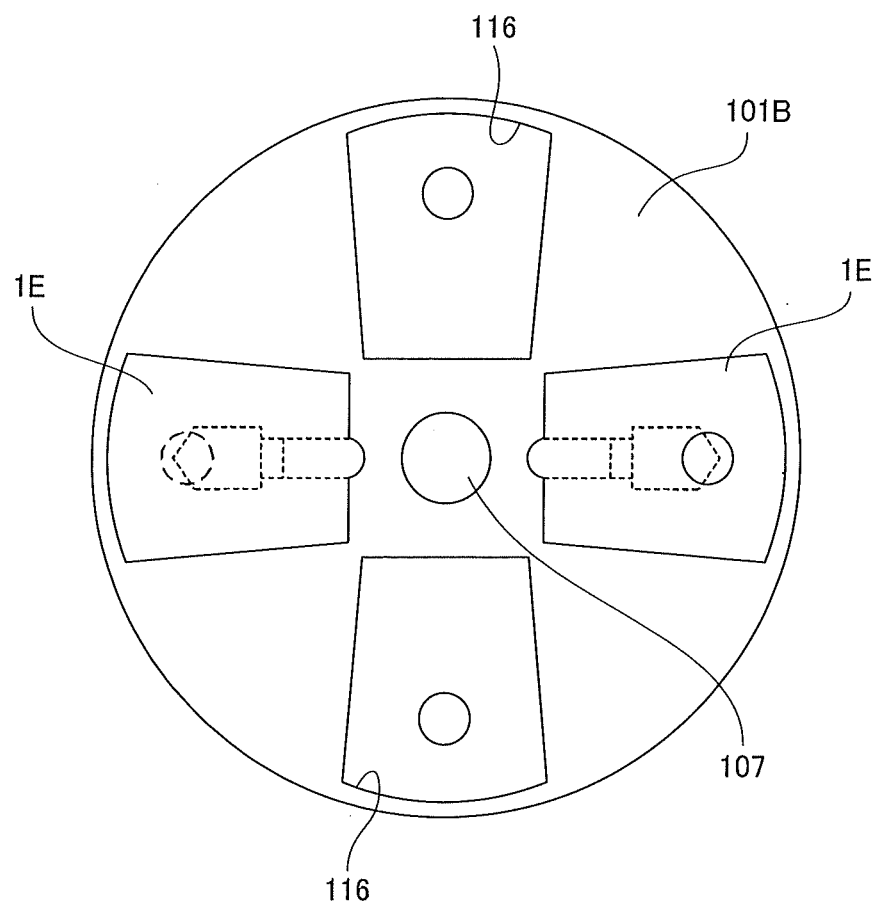
FIG. 44 is a plan view illustrating a case where two analyzing devices are set on a rotor.

FIGS. 42 to 44 illustrate an analyzing apparatus 100 according to the present invention which uses the analyzing device 1E according to the eighth embodiment.

The analyzing apparatus is configured as illustrated in FIG. 42.

A recess 116 on which is set the analyzing device 1E having collected a sample liquid is formed on a disk-like rotor 101B to be rotationally driven around a rotation axial center 107 by a rotation driving unit 106 that is a motor or the like. A penetrating hole 114 is provided in the recess 116 in correspondence to a position of a receiving section 202 of the set analyzing device 1E.

An optical measurement unit 108 that accesses the receiving section 202 of the analyzing device 1E set on the rotor 101B is made up of a light source 112 and a photodetector 113 disposed with the rotor 101B in-between so as to be able to receive light that passes through the hole 114 of the rotor 101B.

A control unit 109 controls a rotational speed and a rotational direction of the rotor 101B, a measurement timing of the optical measurement unit 108, and the like. More specifically, in addition to controlling the rotation driving unit 106 so as to rotate the analyzing device 1E around the rotation axial center 107 via the rotor 101B in any direction at a predetermined rotational speed, the control unit 109 is arranged so as to be capable of causing the analyzing device 1E to perform a left-right reciprocating movement centered around the rotation axial center 107 at a predetermined stop position and at a predetermined amplitude range and a predetermined frequency so as to swing the analyzing device 1E.

A detection light 115 outputted from the light source 112 is transmitted through the hole 114 of the rotor 101B and through a reactant in the receiving section 202 of the set analyzing device 1E, and is received by the photodetector 113 and inputted to a computing section 110. The computing section 110 analyzes characteristics of the sample liquid from an absorption measurement result and displays the characteristics on a displaying section 111.

A centrifugal transfer process and a reagent reaction process of the sample liquid measured by a sample measuring section 201 will be described with reference to FIG. 43.

After setting and fixing the analyzing device 1E whose sample measuring section 201 has been filled with a sample liquid onto the recess 116 of the rotor 101B, by rotating the rotor 101B in a direction depicted by an arrow as illustrated in FIG. 43(a), a centrifugal force is generated on the sample liquid filling the sample measuring section 201 of the analyzing device 1E. As a result, a sample liquid that has previously been stationary at the connected section 207b begins to move towards the receiving section 202. Furthermore, by maintaining a constant number of revolutions, as illustrated in FIG. 43(b), an entirety of a sample liquid measured by the sample measuring section 201 moves to the receiving section 202.

The rotor 101B is swingingly moved so as to accelerate a reaction with a reagent. The swinging operation is performed by repetitively changing rotational directions of the rotor 101B. Specifically, by swingingly moving clockwise and counter-clockwise respectively over ±1 degrees in a state where the microchannel 203 of the analyzing device 1E is oriented in a nine o'clock direction as illustrated in FIG.

43(c), the sample liquid and the reagent moved to the receiving section 202 are agitated and a reaction liquid can be eventually created inside the receiving section 202. As for an angle and a frequency of the swinging movement, ±1 degrees or greater and 22 Hz or greater respectively suffice. By performing a swinging movement satisfying these conditions, a reliable reaction with a reagent can be carried out in a short period of time. In other words, by swingingly moving the analyzing device 1E at a frequency of around 22 Hz and over a minute angle, a sample liquid and a reagent can be reliably mixed.

The analyzing apparatus 100 processes a result of an absorbance measurement by the optical measurement unit 108 with the computing section 110 and displays an analysis result of characteristics of the sample liquid on the displaying section 111.

As shown, since the control unit 109 instructs the rotation driving unit 106 to swingingly move the analyzing device 1E via the rotor 101B, the sample liquid can be analyzed with extremely high accuracy.

FIG. 44 illustrates an analyzing apparatus in operation with two analyzing devices 1E set on the rotor 101B.

While the base substrate 3 and the cover substrate 4 have been formed with a substrate thickness of 1 mm to 7 mm in the sixth and eighth embodiments described above, no limitations need be imposed as long as the substrate thickness enables the microchannel 203 to be formed. The shapes of the base substrate 3 and the cover substrate 4 also need not be limited and a shape suitable for applications and purposes such as a sector-like shape, a disk-like shape, a plate-like shape, and other complicated shapes of a molded material or the like may be adopted.

In addition, while plastic has been used as the material of the base substrate 3 and the cover substrate 4 in the sixth and eighth embodiments described above from the perspectives of moldability, high productivity, and low cost, no limitations need be imposed as long as a bondable material such as glass, a silicon wafer, metal, and ceramic is used.

In the sixth and eighth embodiments described above, while the cover substrate 4 and the base substrate 3 are bonded using an adhesive, bonding may be achieved by such bonding methods as fusion joining, anodic bonding, and laser bonding according to the materials used.

Tenth Embodiment

A rectangular shape of a leading end of a spot application section according to the respective embodiments described above disadvantageously causes a sample liquid to adhere to external wall faces of an analyzing device other than the spot application section during spot application. However, with an analyzing device 1F according to the present tenth embodiment, a proximal end of a spot application section 13A is connected to a capillary cavity 131 and a leading end thereof protrudes from a cover substrate 4, and a shape of the leading end of the spot application section 13A is formed as a hemisphere that protrudes in a direction away from a channel forming face of a base substrate 3.

Figure 45:
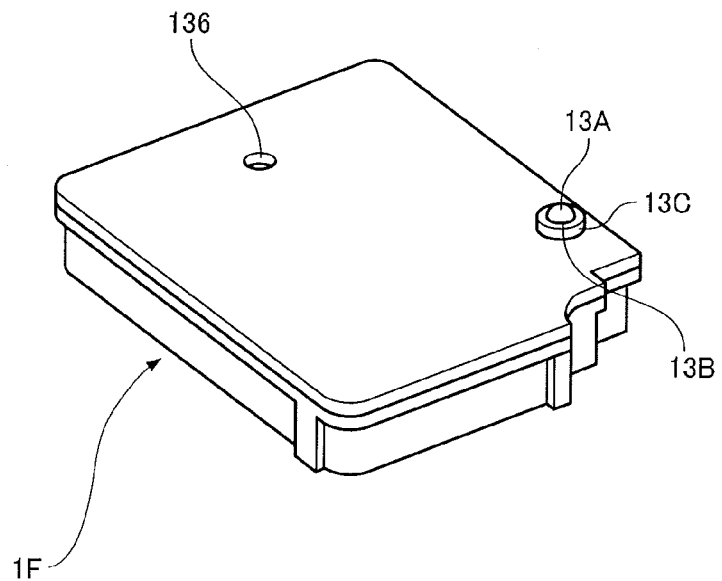
FIG. 45 is a perspective view of an analyzing device according to the eighth embodiment of the present invention.
Figure 46:
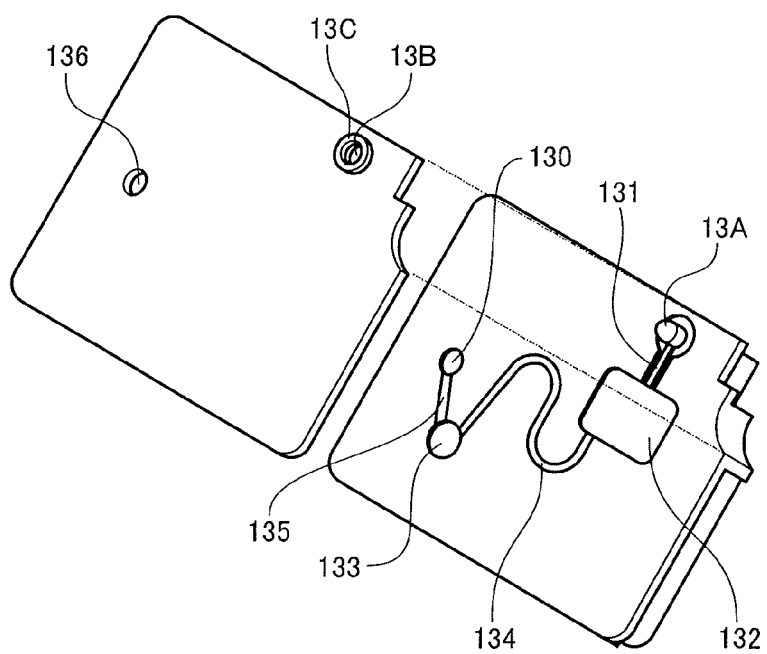
FIG. 46 is an exploded perspective view of an analyzing device according to the eighth embodiment of the present invention.
Figure 47:
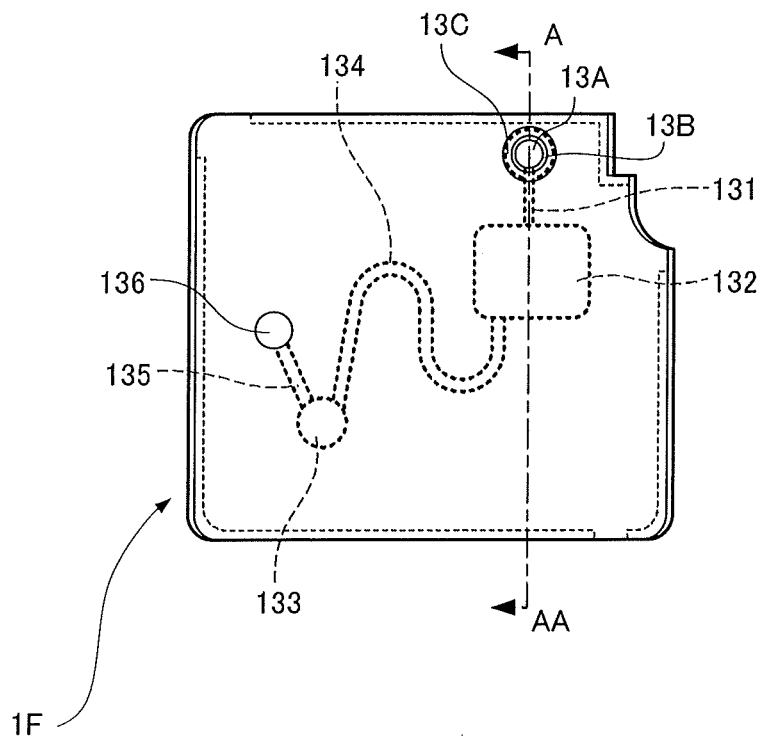
FIG. 47 is a front view of an analyzing device according to the eighth embodiment of the present invention.

As illustrated in FIGS. 45 and 46, the analyzing device 1F is configured by a bonding of the cover substrate 4 and the base substrate 3. A microchannel structure having minute irregularities is formed on a face of the base substrate 3 opposing the cover substrate 4 and is arranged so that various functions such as sample liquid transfer and retention of a predetermined liquid amount are carried out.

The cover substrate 4 includes an inlet 13B, a rib 13C, and an air open hole 136. The base substrate 3 includes the spot application section 13A, the capillary cavity 131, a holding chamber 132, a channel 8, a measurement chamber 133, a channel 9, and an outlet port 130.

In the analyzing device 1F, a predetermined amount of a sample liquid such as blood injected into the inlet 13B is temporarily held in the holding chamber 132 via the capillary cavity 131. The holding chamber 132 holds an analytical reagent (not shown). The sample liquid and the analytical reagent are mixed, and the mixed liquid is transferred to the measurement chamber 133 via a capillary cavity 8. The measurement chamber 133 communicates with a capillary cavity 9 having the air open hole 136. Predetermined items of the mixture of the sample liquid and the analytical reagent transferred to the measurement chamber 133 are measured and analyzed by an optical method.

Figure 48:
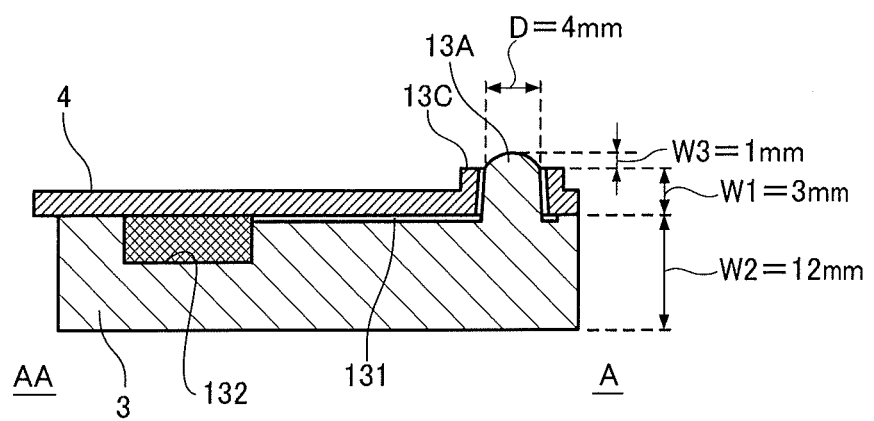
FIG. 48 is a cross-sectional view taken along A-AA in FIG. 47.

As for the shape of the spot application section 13A according to the present embodiment, a proximal end is connected to the capillary cavity 131 and a leading end protrudes from a cover substrate 4. A shape of the leading end of the spot application section 13A is formed as a hemisphere that protrudes in a direction away from a channel forming face of a base substrate 3. Specifically, as illustrated in FIGS. 46 and 48, the shape of the spot application section 13A is a columnar shape provided perpendicular to a channel forming face of the base substrate 3 and the leading end thereof is hemispherical. A gap is formed between the spot application section 13A and the rib 13C. In the case of the spot application section 13A, the gap between the rib 13C is the inlet 13B.

At this point, by superimposing the cover substrate 4 on the base substrate 3, a shape is formed in which the leading end of the spot application section 13A protrudes from the inlet 13B of the cover substrate 4 so as to enable spot application of a sample liquid to be performed easily.

In addition, a diameter D of the inlet 13B and the spot application section 13A is set equal to or slightly greater than a droplet of the sample liquid that is a measurement object, thereby enabling the sample liquid to flow in from any portion of the inlet 13B when spot-applying the sample liquid. Due to such a setup, a configuration capable of causing the adhered sample liquid to entirely flow into the capillary cavity is realized.

In this case, as for a droplet diameter of a sample liquid, when the sample liquid is blood, an amount of blood appearing on a fingertip pierced by a puncture device is approximately 10 µL. Since a diameter of blood in this amount is around 4 mm, a diameter D of the inlet 13B and the spot application section 13A is favorably arranged so as to be around 4 mm which is equal to a blood droplet diameter or to be around 5 mm which is slightly greater.

Furthermore, providing the rib 13C on the cover substrate 4 so as to surround the spot application section 13A has an effect of preventing a finger or the like from coming into contact with locations other than the spot application section 13A and preventing blood from adhering to such locations during spot application. A height of the rib 13C is set lower than the spot application section 13A. This is because if the height of the rib 13C is greater than the spot application section 13A, a sample liquid cannot be suctioned when a fingertip is pressed against the inlet 13B to completely cover the inlet 13B. The rib 13C is integrally resin-molded with the cover substrate 4. A surface of the rib 13C molded from a synthetic resin material is able to repel blood due to a water-shedding quality of the synthetic resin material itself.

When mixing of the reagent and the sample liquid reaches a predetermined level, a sample liquid in the holding chamber 132 is carried to an inlet port of the measurement chamber 133 by a capillary force through a channel 8, and is then transferred into the measurement chamber 133 utilizing a centrifugal force generated by rotating the analyzing device 1F at a predetermined number of revolutions. A predetermined item of the transferred sample liquid is optically measured at the measurement chamber 133.

A measurement of the sample liquid involves irradiating light on the measurement chamber 133 and optically analyzing a reactive state of the liquid sample to be tested and an analytical reagent. Since absorbance varies according to a ratio of a reaction between a sample liquid and an analytical reagent, a predetermined item can be measured and a reactive state can be analyzed by measuring an absorbance of light to be irradiated. In the present embodiment, a sample liquid is held in the holding chamber 132 by a capillary force via the capillary cavity 131 that leads to the inlet 13B.

Wall faces of channels 134 and 135 have been subjected to hydrophilic treatment. Methods of such hydrophilic treatment include a surface treatment method using plasma, corona, ozone, or an active gas such as fluorine, and surface treatment with a surfactant or a hydrophilic polymer. In this case, hydrophilicity refers to a contact angle with water that is less than 90 degrees.

An effect according to the present embodiment will be described.

A specific example of dimensions of the analyzing device 1F will be described.

In this case, as illustrated in FIG. 48, a diameter D of the inlet 13B and the spot application section 13A is set such that D=4 mm, the leading end of the spot application section 13A is formed in a hemispherical shape, and a protrusion height W3 of the spot application section 13A from the rib 13C is formed such that W3=1 mm. A thickness of portions of the cover substrate other than the rib 13C is set to 2 mm, while a thickness W1 of the cover substrate 4 at the portion of the rib 13C is set such that W1=3 mm. A thickness W2 of the base substrate 3 that gives the analyzing device 1F an integral structure is set such that W2=12 mm, and the analyzing device 1F is to be arranged as an approximately 65 mm square.

A size of the analyzing device 1F can be varied as appropriate to achieve a suitable size as a sample liquid collecting section. In addition, a thickness of the capillary cavity 131 forming a channel of the sample liquid or, in other words, a channel depth is set to 0.1 mm. On the other hand, a depth of the holding chamber 132 coupled to the capillary cavity 131 and formed on the base substrate 3 of the analyzing device 1F is formed deeper than the thickness of the capillary cavity 131 (i.e., eventual channel depth) so as to be 0.3 mm to 0.5 mm. Due to such a configuration, a sample liquid injected into the capillary cavity 131 does not proceed to the holding chamber 132 by a capillary force alone and is transferred utilizing a centrifugal force obtained by rotating the analyzing device 1F. It is obvious that a similar effect can be obtained by cross-sectional shapes of the capillary cavity 131 other than a rectangular shape such as a circular shape and an elliptic shape as long as the shape enables capillary force to act.

While depths of the capillary cavity 131 and the channels 134 and 135 according to the present invention are formed so as to be equal to or greater than 0.02 mm and less than 0.3 mm, such dimensions are not restrictive as long as a sample liquid flows by a capillary force. Generally, since a liquid such as blood is to be measured and analyzed, depths are desirably set so as to equal to or greater than 0.02 mm and less than 0.3 mm. In addition, while the depths of the holding chamber 132 and the measurement chamber 133 are formed so as to range from 0.3 mm to 0.5 mm, the depths can be adjusted according to a sample solution volume and conditions for measuring absorbance (optical path length, measured wavelength, reaction concentration of sample solution, reagent type, and the like). Subsequently, a sample liquid transferred to the measurement chamber 133 is optically measured.

Figure 49A:
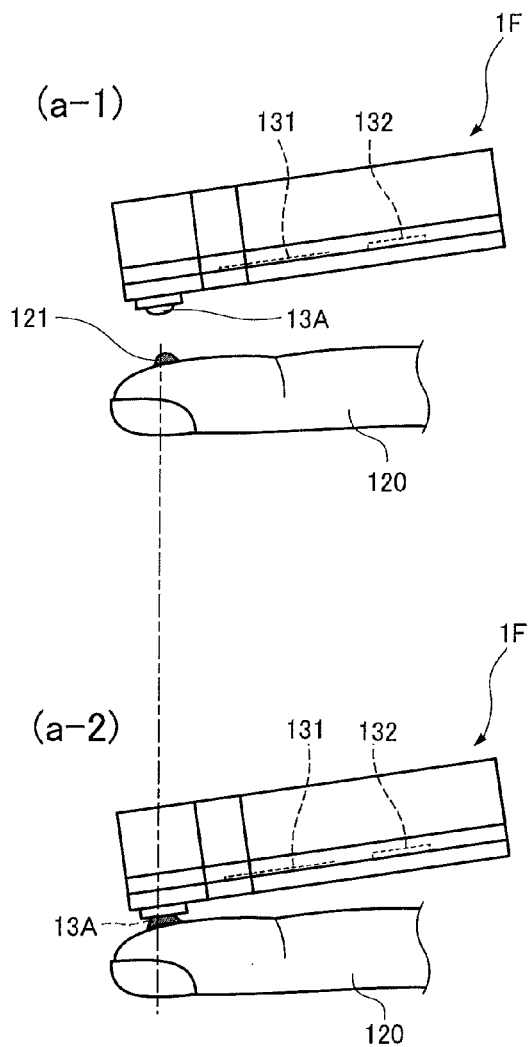
FIG. 49A is an explanatory diagram of a situation during spot application according to the eighth embodiment of the present invention.

FIG. 49A illustrates a situation during spot application.

Figure 49B:
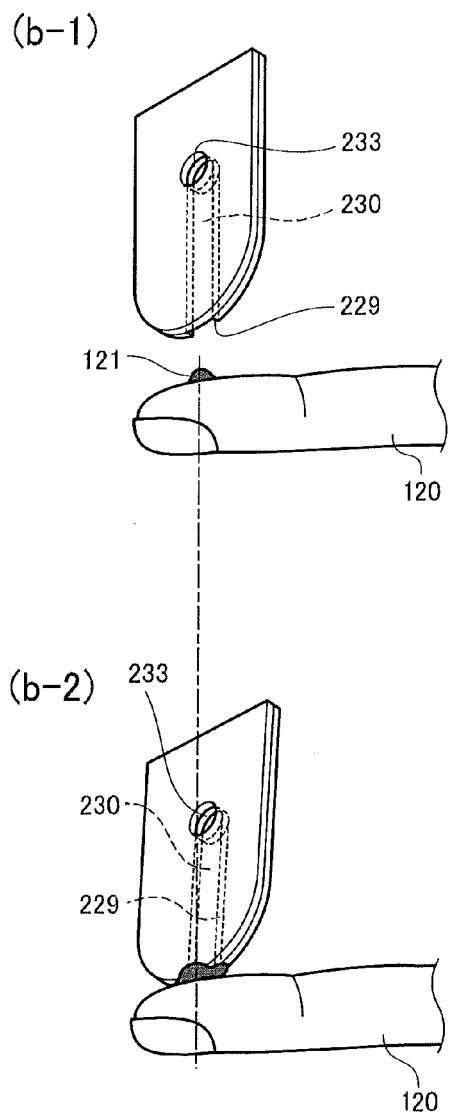
FIG. 49B is an explanatory diagram of a situation during spot application according to a conventional example.

Reference characters (a-1) and (a-2) in FIG. 49A represent the present embodiment and (b-1) and (b-2) in FIG. 49B represent a conventional example.

FIGS. 49A(a-1) and 49B(b-1) are diagrams before spot application and FIGS. 49A(a-2) and 49B(b-2) are diagrams during spot application.

In FIG. 49A(a-1), when the blood drop 121 on the fingertip 120 of a testee is spot-applied on the spot application section 13A, since a leading end of the spot application section 13A is hemispherically arranged, a sample liquid flows along the hemispherical spot application section 13A and can be spot-applied without adhering to outer walls of the analyzing device 1F. However, from FIG. 49B(b-1), it can be confirmed that when the blood drop 121 is applied to the spot application section 13A, besides being introduced to the capillary cavity 131, a sample liquid inadvertently adheres to outer walls of the analyzing device 1F. Therefore, by comparing FIG. 49A and FIG. 49B, an effect of shapes in the present embodiment has been confirmed.

Figure 50:
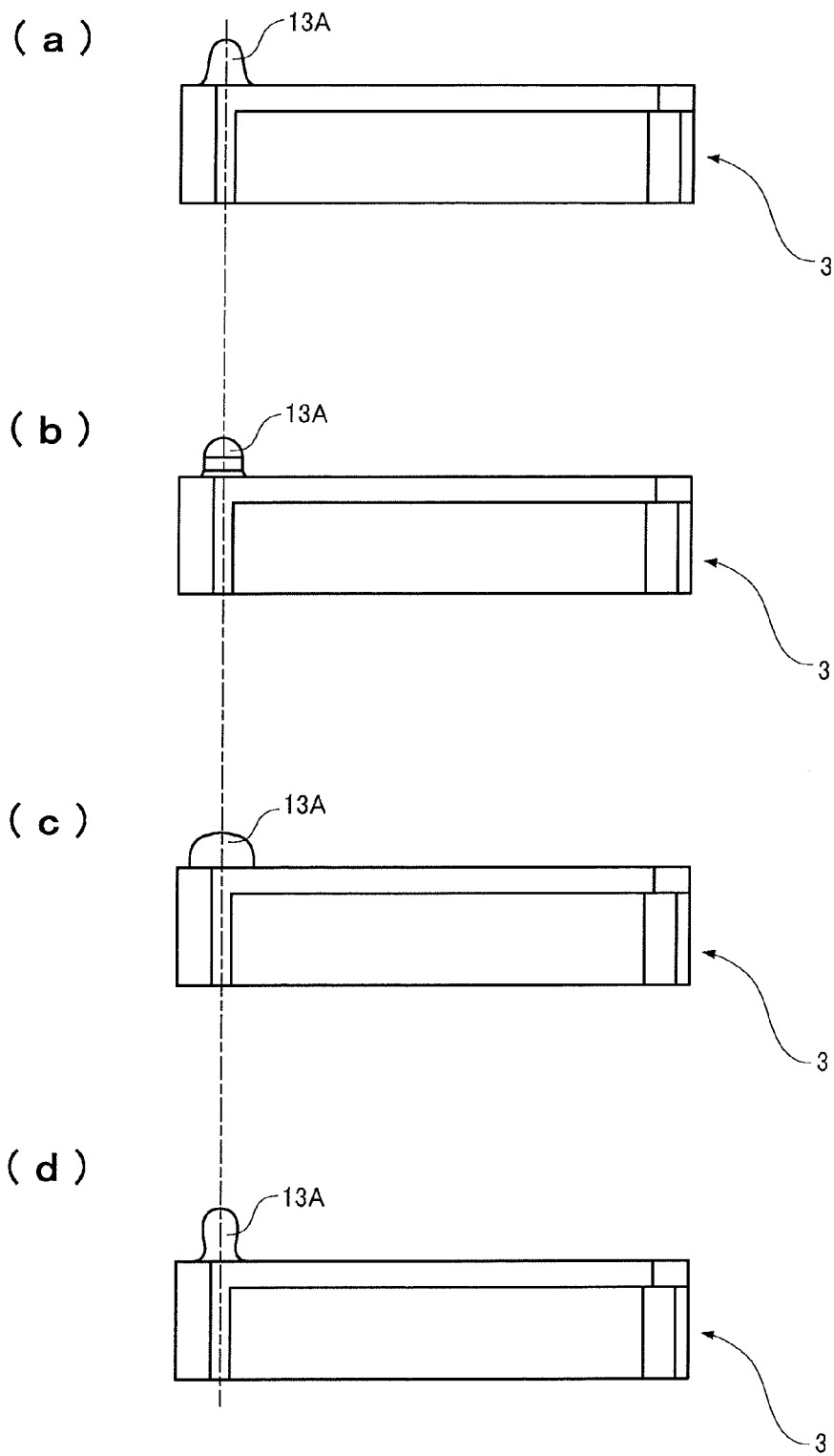
FIG. 50 is a diagram of similar shapes of a spot application section according to the eighth embodiment of the present invention.

FIG. 50 illustrates similar shapes of the spot application section 13A.

As illustrated in FIGS. 50(a) to 50(d), every shape of the leading end of the spot application section 13A is made up by smooth curves. This is to assist conformance of the sample liquid. The illustrated shapes enable a sample liquid to only adhere to a spot application section during spot application in the same manner as the spot application section 13A illustrated in FIGS. 45 to 48.

From the description above, it is confirmed that a sample liquid can be made to adhere only to a spot application section by arranging a leading end of the spot application section so as to have a hemispherical shape.

Eleventh Embodiment

With the analyzing devices according to the respective, embodiments described above, when injecting a sample from a sample injection tool such as a syringe, a dropper, or a pipette, it is required that a leading end of the sample injection tool is brought into contact with a sample inlet of the analyzing device, and the sample must be suctioned by a capillary force by spot-applying small amounts of the sample a number of times which can be held at the outside of the inlet by surface tension. Alternatively, a sample must be dropped from a sample injection tool onto a sheet-like test specimen made of plastic or glass and suctioned by bringing a sample inlet of an analyzing device into contact with the dropped sample. However, by forming a plurality of inlets as is the case with an eleventh embodiment on the analyzing devices according to the respective embodiments described above, a mode of injection using a sample injection tool can be accommodated in addition to direct spot application.

FIGS. 51 to 63 illustrate an eleventh embodiment of the present invention.

Figure 51:
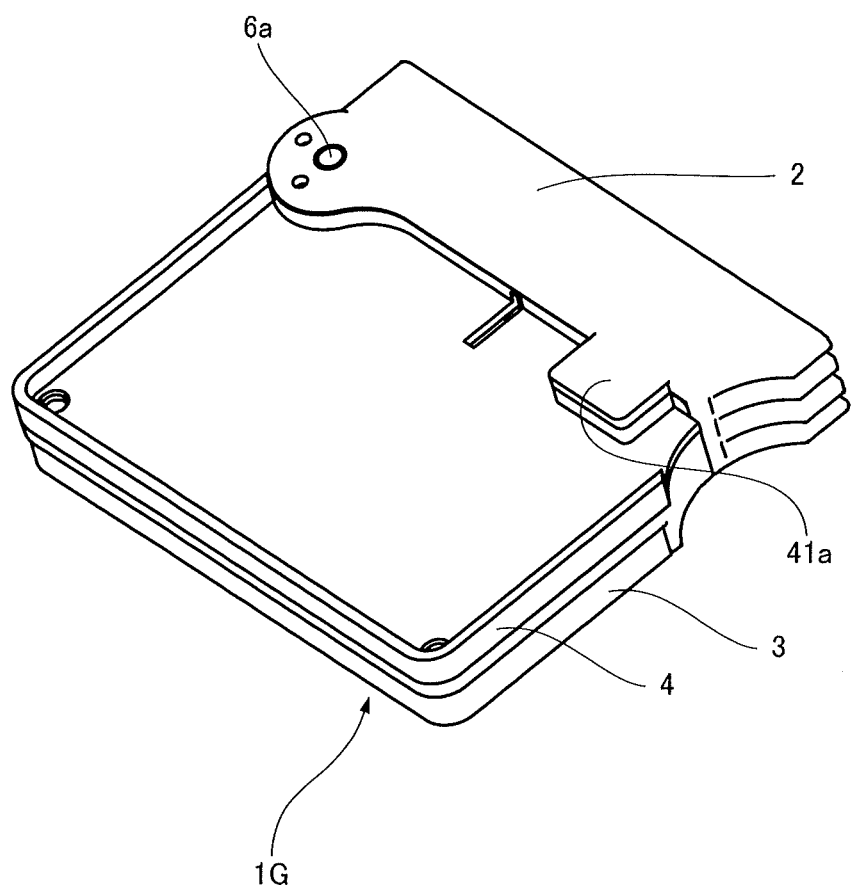
FIG. 51 is an external view of an analyzing device according to the eighth embodiment of the present invention.
Figure 52:
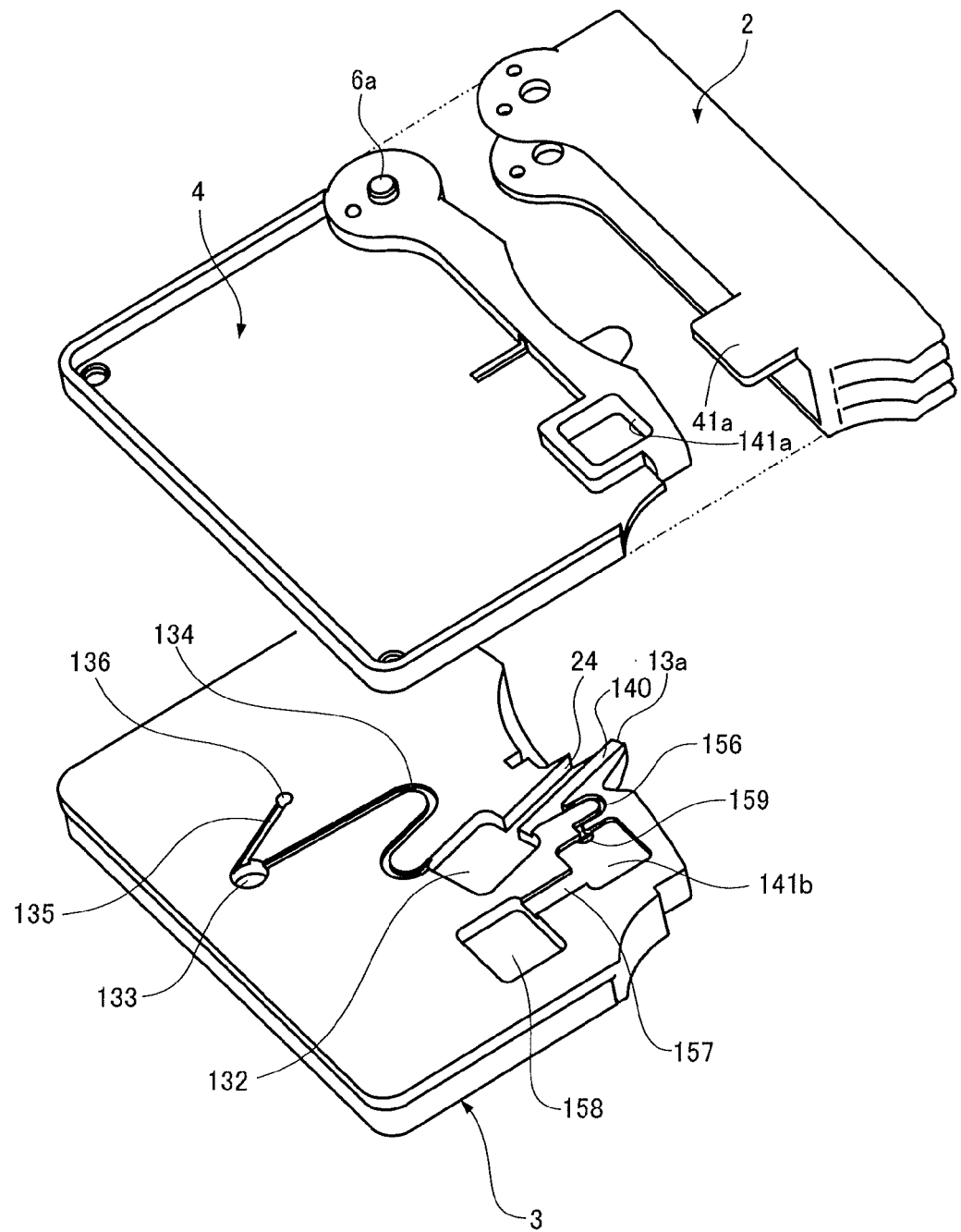
FIG. 52 is an exploded perspective view of an analyzing device according to the eighth embodiment of the present invention.

FIGS. 51 and 52 illustrate an analyzing device 1G according to an eleventh embodiment of the present invention.

The analyzing device 1G is configured by a bonding of a cover substrate 4 and a base substrate 3. A microchannel structure having minute irregularities is formed on a face of the base substrate 3 and is arranged so that various functions such as sample liquid transfer and retention of a predetermined liquid amount are carried out. The cover substrate 4 and the base substrate 3 are to be bonded by a well known bonding method such as ultrasonic bonding and UV adhesion. After bonding, a protective cap 2 is attached that is openable and closable around a shaft 6a in order to prevent scattering of a sample liquid.

A first inlet 13a is an inlet port-side opening made up of a groove-like first capillary cavity 140 formed on the base substrate 3 and a convex protrusion 4b (refer to FIG. 54) formed on the cover substrate 4 so as to close a longitudinal opening of the first capillary cavity 140.

A second inlet 141 is made up of a recess 141b formed on the base substrate 3 and a hole 141a formed on the cover substrate 4 and which communicates with the recess 141b. In an in-use state, an opening of the hole 141a is covered and closed by a lid 41a formed on the protective cap 2.

Figure 54:
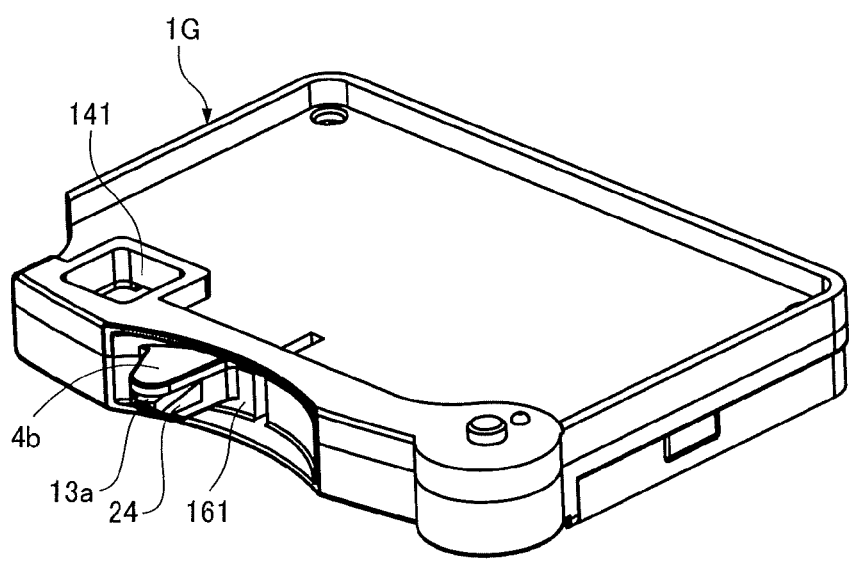
FIG. 54 is a perspective view of an analyzing device as seen from a periphery of a first inlet according to the eighth embodiment of the present invention.

FIG. 54 is a perspective view of the analyzing device 1G as seen from a periphery of the first inlet 13a. By arranging the first inlet 13a as a convex protrusion 4b protruding from a lateral face of an analyzing device main body, an effect can be achieved in that a spot application of blood by a fingertip can be more easily performed, and a finger can be prevented from coming into contact with a location other than the first inlet 13a during spot application so as to prevent blood from adhering to such a location.

Figure 53:
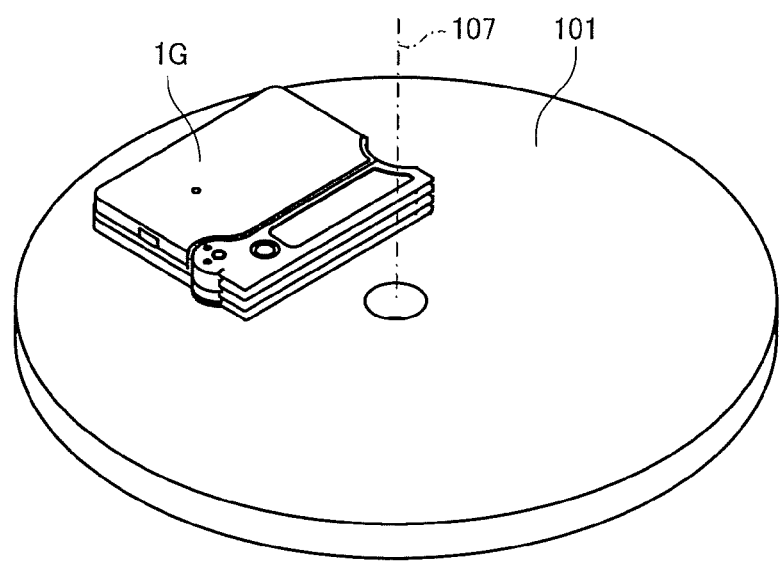
FIG. 53 is an external perspective view illustrating an image of an analyzing device being mounted on a rotor of an analyzing apparatus according to the eighth embodiment of the present invention.

FIG. 53 illustrates a state where one analyzing device 1G has been set on a rotor 101 of an analyzing apparatus 100. An analyzing apparatus-side rotation driving unit (not shown) rotationally drives the rotor 101 in a predetermined direction around a rotation axial center 107. The analyzing device 1G is set on the rotor 101 such that the first inlet 13a faces the direction of the rotation axial center 107.

As illustrated in FIG. 54, a recess 161 is formed around the first inlet 13a on a lateral face of the analyzing device 1G. When seen in a state where the recess 161 is set on the rotor 101, only a rotation axial center 107 side of the recess 161 is opened and is depressed circumferentially outward of the rotation axial center 107.

By forming the recess 161 so as to have a gently curving structure in which a sectional area of an axial center-side opening of the recess is equal to or greater than a sectional area of a circumferentially outward opening of the recess, a sample liquid having adhered to a periphery of the first inlet 13a is reliably transferred to the rear of the recess 161 by a centrifugal force accompanying a rotation of the rotor 101, and becomes more likely to be transferred to a lowermost location of the recess 161. Therefore, the sample liquid can be collected without being scattered to the outside of the recess 161.

Figure 55:
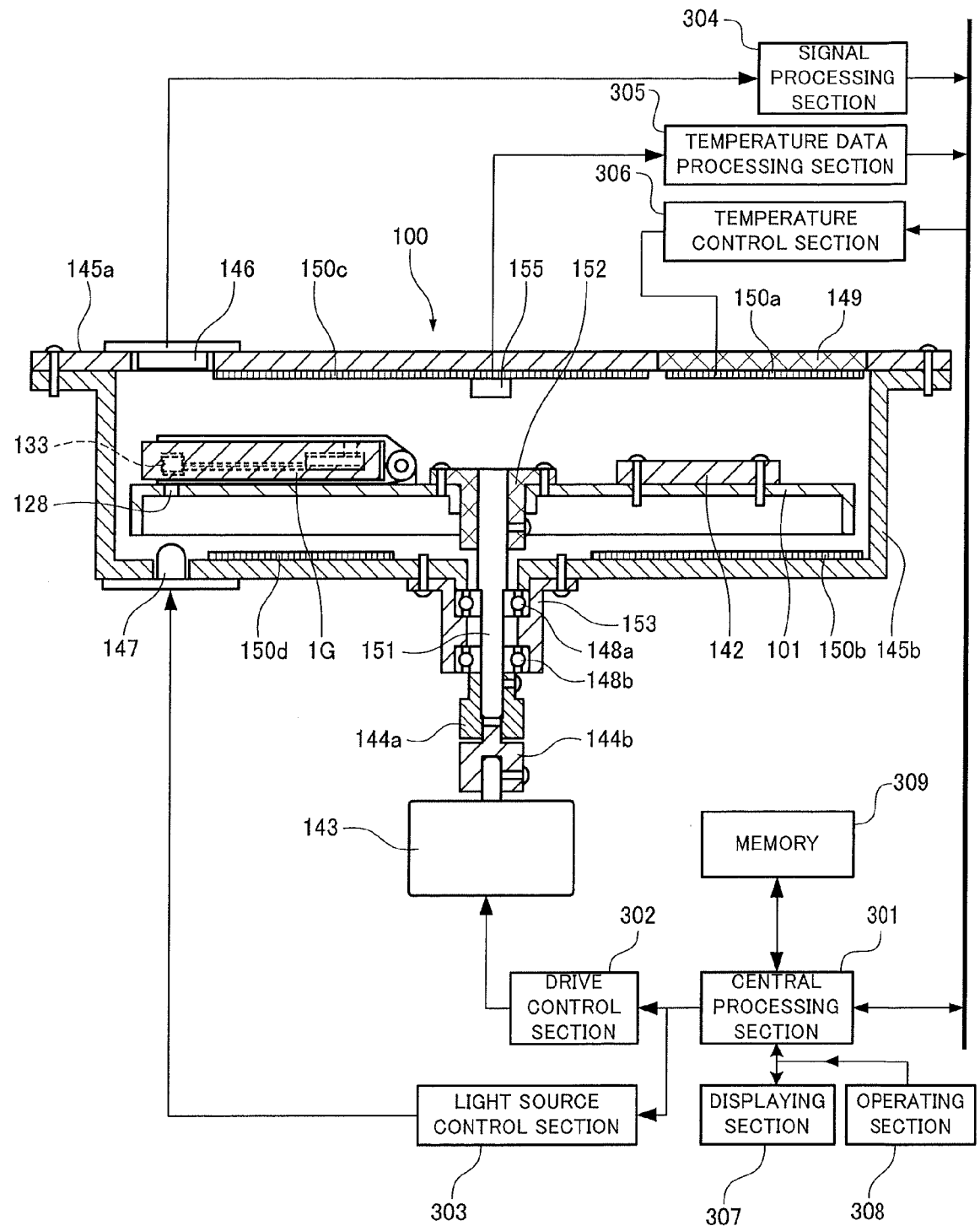
FIG. 55 is a central cross-sectional view of an analyzing apparatus in a state where an analyzing device has been mounted according to the eighth embodiment of the present invention.

As illustrated in FIG. 55, in the analyzing apparatus 100, the rotor 101 and a shaft 151 are fastened via a rotor holding member 152 and are drivingly coupled by couplings 144a and 144b respectively fixed to a motor 143, the shaft 151, and a motor shaft. The shaft 151 is rotatably supported by ball bearings 148a and 148b fixed to a bearing holding member 153. Under a drive instruction from a central processing section 301 made up of a CPU and the like, the motor 143 is rotated in a desired rotational direction at a desired rotational speed by a current applied to the motor 143 via a drive control section 302 made up of a driver IC and the like. A balancer 142 for ensuring balance during rotation with the analyzing device 1G is disposed on the rotor 101. A rotating portion including the rotor 101 and the analyzing device 1G is in a space sealed by an upper housing 145a and a lower housing 145b. The housing space is heated by heaters 150a to 150d.

Figure 56:
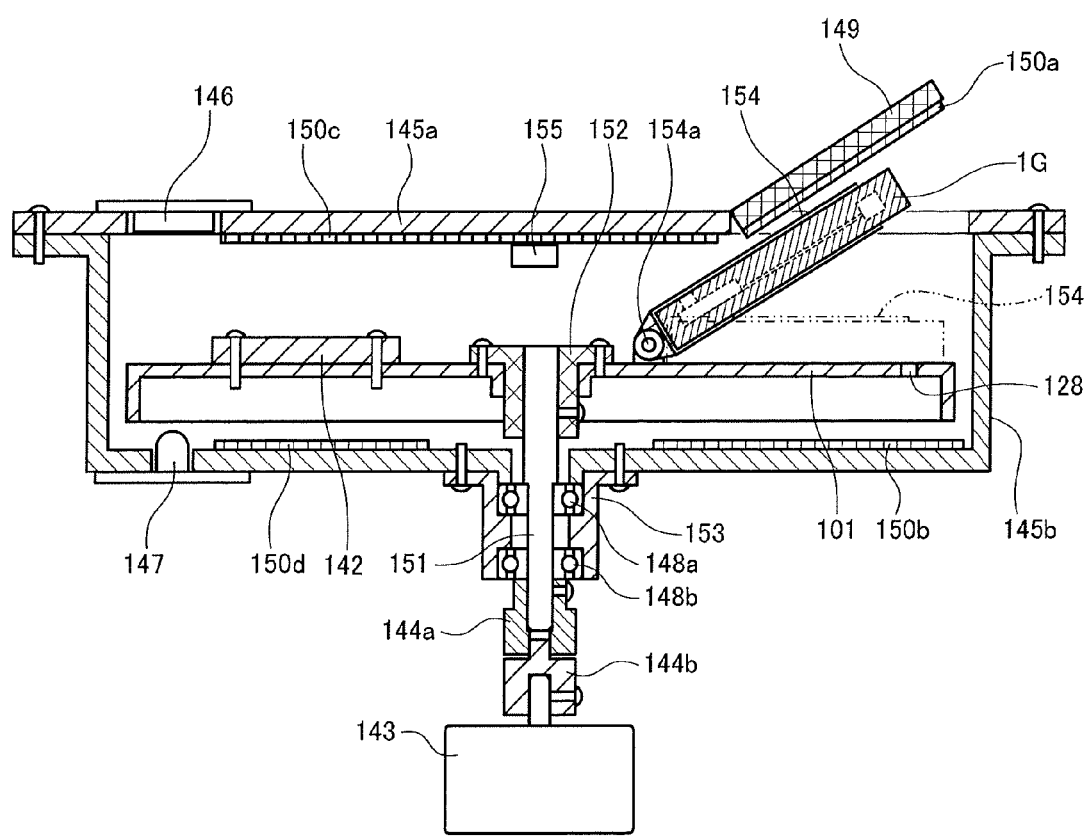
FIG. 56 is a central cross-sectional view of an analyzing apparatus during mounting of an analyzing device according to the eighth embodiment of the present invention.

Hereinafter, in regards to a specific sample liquid measurement method of the analyzing apparatus 100 according to the present invention, procedures up to an insertion of the analyzing device 1G into the analyzing apparatus will be described with reference to FIG. 56, and subsequent procedures will be described with reference to FIG. 55.

Before mounting the analyzing device 1G onto the analyzing apparatus 100, a user injects a sample liquid into the analyzing device 1G through the first inlet 13a or through the second inlet to be described later. Subsequently, as illustrated in FIG. 56, a door 149 provided on the upper housing 145a is opened. In conjunction with the opening of the door 149, a clam shell-type analyzing device holding member 154 rotationally moves around a shaft 154a of a proximal end and a state illustrated in FIG. 56 is entered in which a leading end of the analyzing device holding member 154 approaches a location opened by the door 149.

By inserting the analyzing device 1G into the analyzing device holding member 154 and closing the door 149, the analyzing device holding member 154 returns to a position depicted by an imaginary line and holds the analyzing device 1G at a predetermined position on the rotor 101.

Subsequently, the user operates an operating section 308 at which an operating button for instructing a start of measurement and the like are arranged to start a measurement of a sample liquid component. An instruction from a user is interpreted at the central processing section 301. The motor 143 is driven by the drive control section 302 to rotate and/or stop the analyzing device 1G, and utilizing a centrifugal force and/or a capillary force, an analysis object is eventually introduced into a measurement chamber 133 (refer to FIG. 52) of the analyzing device 1G.

Prior to the introduction to the measurement chamber 133, an enzymatic reaction has been caused between blood plasma and a reagent (not shown) made up of an enzyme, a pigment, a buffer and the like disposed in the holding chamber 132 of the analyzing device 1G and a color reaction is given. At this point, melting and agitation can be promoted by varying the number of revolutions of the motor 143 from, for example, 500 rpm to 1500 rpm so as to apply acceleration or by repeating positive and negative rotational movements from clockwise to counter-clockwise. The color-reacted reaction liquid is transferred to the measurement chamber 133 and irradiated by a light source 147 via the hole 128, whereby a transmitted light is detected by a detector 146. Absorbance is determined from a ratio of reflected light against incident light, and based on a calibration curve held in a memory 309, a concentration of a specific component is computed by the central processing section 301 and displayed on a displaying section 307.

In addition, when the sample liquid is a blood specimen, temperature dependence is generally high and affects measurement time and measurement accuracy. Therefore, preferably, at least the temperature after starting a reagent reaction is kept constant (30° C. to 37° C.). To this end, with the analyzing apparatus 100, heaters 150a to 150d are controlled by a temperature control section 306 based on a detection result of a temperature data processing section 305 of a temperature sensor 155 to manage the air temperature inside the housing space in order to set the temperature to at least 37° C. upon start of the reaction with the reagent. By keeping the air temperature inside the housing constant in this manner, the analyzing device 1G can be uniformly heated without unevenness.

Moreover, depending on applications, depending on configurations of chambers and channels inside the analyzing device 1G, the analyzing apparatus 100 can also become a centrifugal separator that transfers and centrifugally separates a liquid inside the analyzing device 1G utilizing a centrifugal force generated by a rotation around an axial center.

The analyzing device 1G may have a sector-like shape, a cubic shape, or any other shape. A plurality of analyzing devices 1G may be simultaneously mounted on the rotor 101.

Next, a microchannel configuration of the analyzing device 1G and a sample liquid transfer process according to the present eleventh embodiment will be described in detail.

Figure 57:
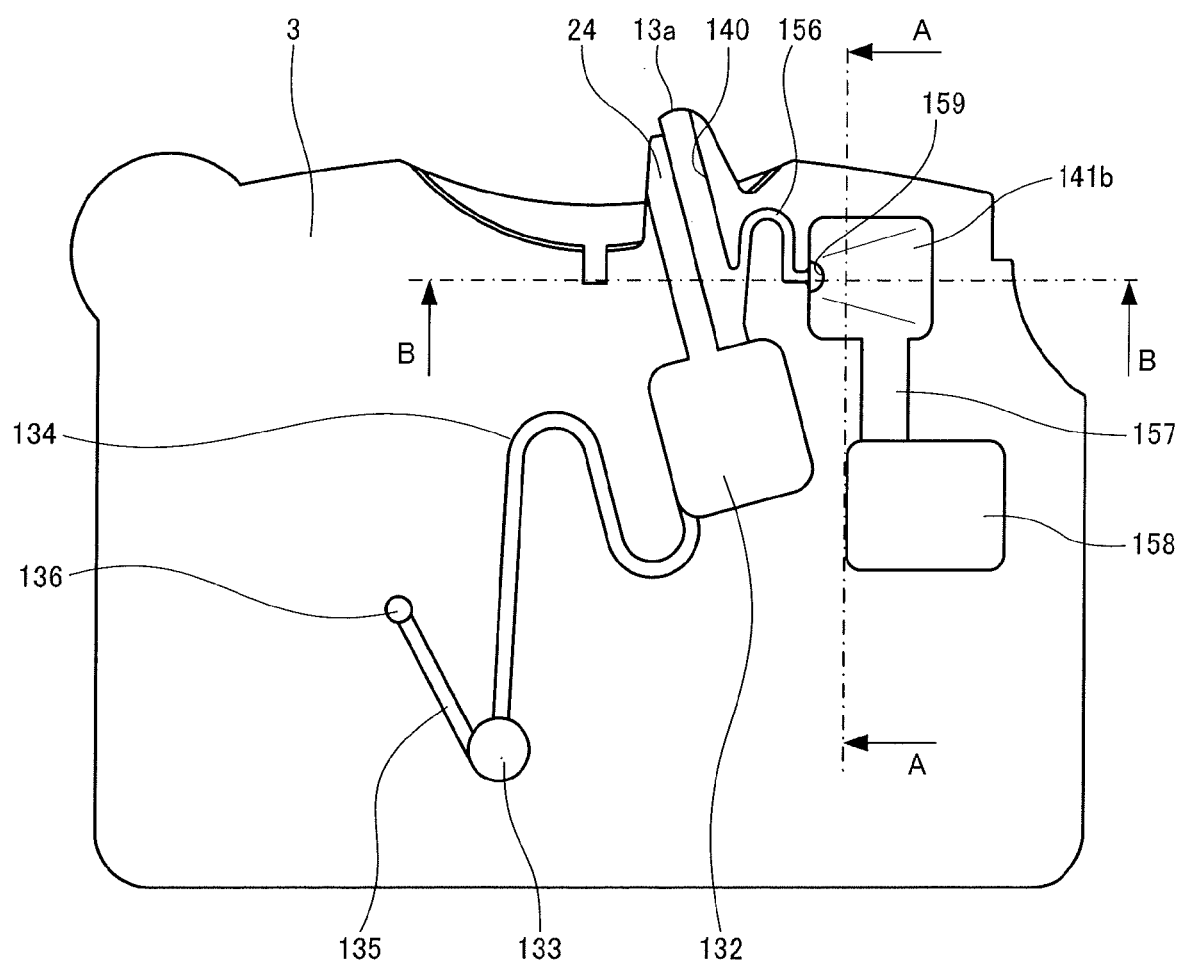
FIG. 57 is a plan view illustrating a microchannel structure of an analyzing device according to the eighth embodiment of the present invention.
Figure 58:
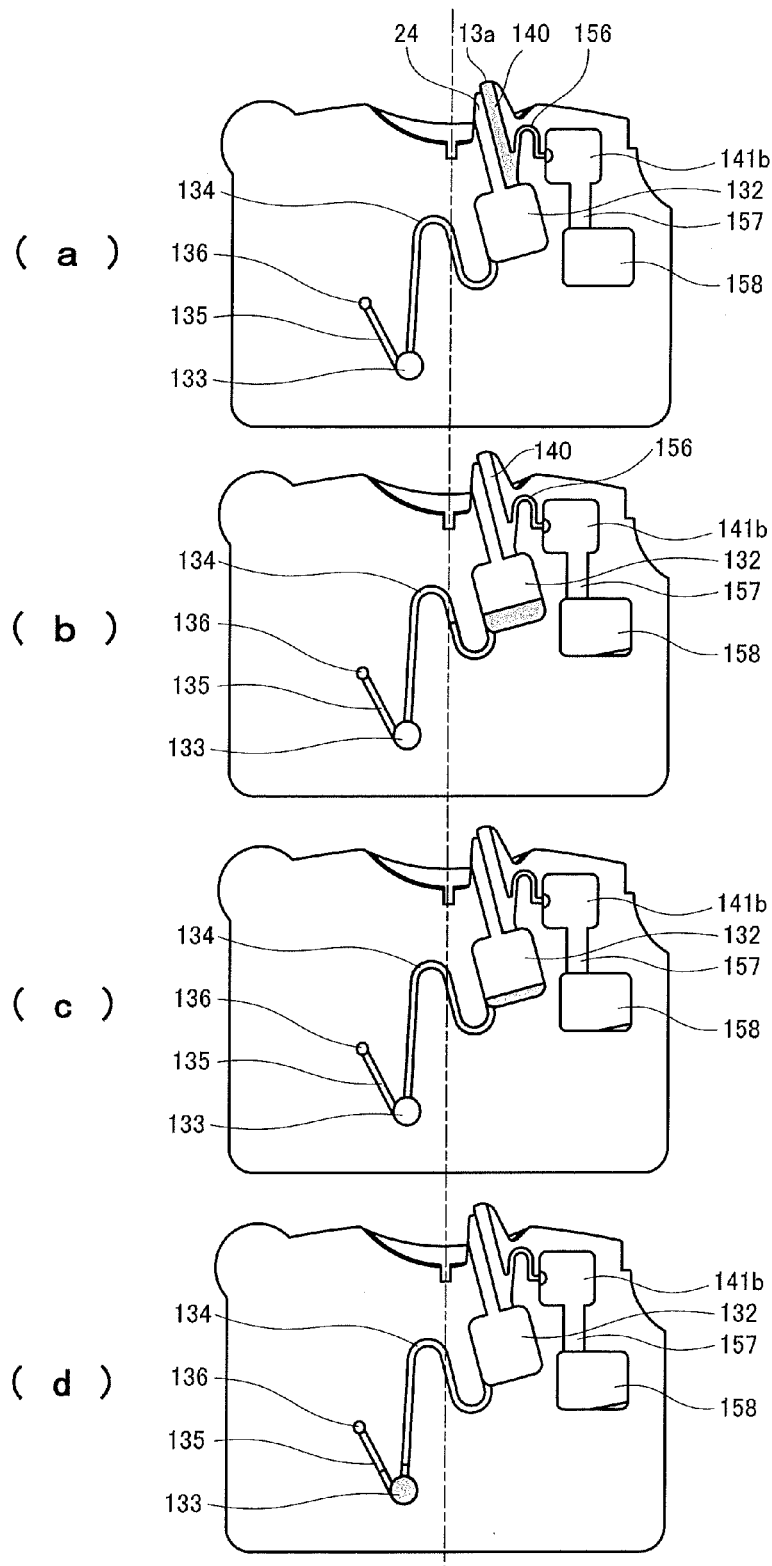
FIG. 58 is a process diagram covering from a sample liquid injection process to a measurement chamber filling process when a sample liquid is injected from a first inlet of an analyzing device according to the eighth embodiment of the present invention.
Figure 59:
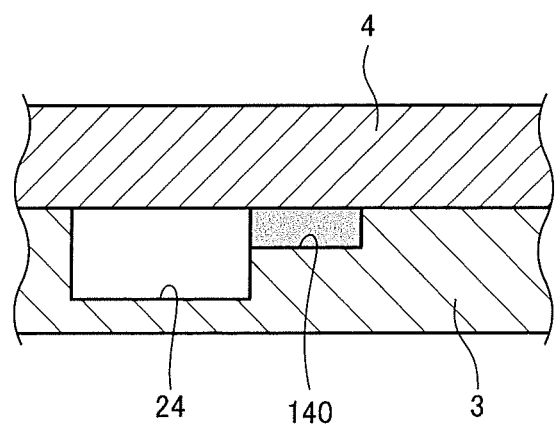
FIG. 59 is a cross-sectional view illustrating an example of shapes of a capillary cavity and a cavity of an analyzing device according to the eighth embodiment of the present invention.

FIG. 57 illustrates a microchannel structure of the analyzing device 1G illustrated in FIGS. 51 and 52. FIG. 58 illustrates a transfer process from sample liquid injection to the measurement chamber when the sample liquid is injected from the first inlet 13a. FIG. 59 illustrates an example of a capillary cavity and a cross-sectional shape of a cavity.

As illustrated in FIG. 57, the microchannel structure of the analyzing device 1G includes: the first inlet 13a for collecting a sample liquid; the first capillary cavity 140 for holding just a predetermined amount of the sample liquid injected into the first inlet 13a; a second capillary cavity 156 having a siphon structure; a cavity 24 for discharging air inside the first capillary cavity 140; the holding chamber 132 holding an analytical reagent (not shown); the measurement chamber 133 for measuring a mixture of the sample liquid and the analytical reagent; the channel 134 communicating with the holding chamber 132 and the measurement chamber 133; and a channel 135 communicating with the measurement chamber 133 and an air open hole 136.

In this case, while depths of the first capillary cavity 140 and the channels 134 and 135 are formed so as to range from 50 μm to 300 μm, such dimensions are not restrictive as long as a sample liquid flows by a capillary force. While the depths of the holding chamber 132, the measurement chamber 133, and the cavities 24 and 16 are formed so as to range from 0.3 mm to 5 mm, the depths can be adjusted according to a sample solution volume and conditions for measuring absorbance (optical path length, measured wavelength, reaction concentration of sample solution, reagent type, and the like).

In order to cause a sample liquid to flow by a capillary force, wall faces of the first capillary cavity 140 and channels 134 and 135 have been subjected to hydrophilic treatment. Methods of such hydrophilic treatment include a surface treatment method using plasma, corona, ozone, or an active gas such as fluorine, and surface treatment with a surfactant or a hydrophilic polymer. In this case, hydrophilicity refers to a contact angle of less than 90 degrees with respect to water, and more favorably, a contact angle of less than 40 degrees.

—Transfer Process when Sample Liquid is Introduced into the First Inlet 13a—

A transfer process in this case is to be executed as illustrated in FIG. 58.

In order to supply a sample liquid to the analyzing device 1G, a sample liquid is spot-applied to the first inlet 13a from a lateral face of the analyzing device 1G before setting the analyzing device 1G on the analyzing apparatus 100. Immediately after spot application, as illustrated in FIG. 58(a), quantitatively a predetermined amount of the sample liquid is injected into the first capillary cavity 140 and the second capillary cavity 156 with a siphon structure by capillary action.

At this point, since the cavity 24 for discharging air inside the first capillary cavity 140 is provided on a lateral face of the first capillary cavity 140, the sample liquid becomes a capillary flow in which a central portion of the first capillary cavity 140 precedingly flows instead of a capillary flow in which lateral face-portions of the first capillary cavity 140 precedingly flows, and fills the inside of the first capillary cavity 140. Therefore, even if the sample liquid spot-applied to the first inlet 13a runs out while the first capillary cavity 140 is being filled or if the sample liquid is inadvertently detached from the first inlet 13a while the first capillary cavity 140 is being filled, by recommencing spot-application from the first inlet 13a, the sample liquid at the central portion of the first capillary cavity 140 precedingly flows and comes into contact with a central portion of a sample liquid held in the capillary cavity, and proceeds to fill the capillary cavity while discharging air in a lateral face-direction in which the cavity 24 exists. Therefore, air bubbles are not generated, and spot-applications can be repeatedly performed until a predetermined amount of the sample liquid is held by the first capillary cavity 140.

As for the first capillary cavity 140 and the cavity 24, the cavity 24 whose cross-sectional dimension in the thickness direction is greater than the cross-sectional dimension of the first capillary cavity 140 is provided on a lateral face on one side of the rectangular first capillary cavity 140 formed on the base substrate 3 as illustrated in FIG. 59. The configurations of the first capillary cavity 140 and the cavity 24 are not limited to the aforementioned.

With the configuration illustrated in FIG. 59, by arranging the cross-sectional dimension of the cavity 24 in the thickness direction to exceed the cross-sectional dimension of the first capillary cavity 140 by 50 μm or more, influx of the sample liquid to the cavity 24 can be prevented. While an upper limit of the cross-sectional dimension of the cavity 24 in the thickness direction is not particularly prescribed, since the cover substrate 4 must have rigidity in order to maintain the cross-sectional dimension of the capillary cavity in the thickness direction, a distance from the surface of the cover substrate 4 to the cavity 24 desirably ranges from 0.5 to 1 mm. In addition, while hydrophilic treatment must be performed in order to ensure capillary action in the first capillary cavity 140, hydrophilic treatment is desirably performed only on wall faces of the first capillary cavity 140. Performing hydrophilic treatment on other wall faces such as the cavity 24 results in a flow of the sample liquid into the cavity 24.

After the first and second capillary cavities 140 and 156 are filled with the sample liquid, by setting the analyzing device 1G in a state where the protective cap 2 is closed as illustrated in FIG. 51 onto the analyzing apparatus 100 and rotating the analyzing device 1G using the driving unit of the analyzing apparatus 100, as illustrated in FIG. 58(b), the sample liquid in the first and second capillary cavities 140 and 156 is transferred by a centrifugal force into the holding chamber 132 which holds an analytical reagent in advance. In addition, at this point, a small amount of the sample liquid in the second capillary cavity 156 is transferred to the overflow chamber 158.

The sample liquid having flowed into the holding chamber 132 is mixed with the analytical reagent held in the holding chamber 132 by a swinging motion caused by acceleration of a rotation of the analyzing apparatus 100 or by liquid diffusion during suspension of rotation. However, mixing may alternatively be performed by applying an external force that directly vibrates the holding chamber itself.

Next, when mixing of the reagent and the sample liquid reaches a predetermined level, as illustrated in FIG. 58(c), the sample liquid in the holding chamber 132 is carried to an inlet port of the measurement chamber 133 by a capillary force through the channel 134.

Subsequently, as illustrated in FIG. 58(d), the sample liquid inside the channel 134 is transferred into the measurement chamber 133 by a rotation of the analyzing apparatus 100. A component concentration of the sample liquid can be measured by measuring a reactive state of the sample liquid and the analytical reagent through absorbance measurement or the like using a measuring unit (not shown) installed on the analyzing apparatus 100.

—Transfer Process when Sample Liquid is Introduced into the Second Inlet 141—

A transfer process in this case is to be executed as illustrated in FIG. 60. In addition, FIG. 61A to be used in the following description represents a cross-sectional view taken along A-A in FIG. 57, and FIG. 61B represents a cross-sectional view taken along B-B in FIG. 57.

In this case, before setting the analyzing device 1G on the analyzing apparatus 100, a user spot-applies a sample liquid into the widely opened hole 141a of the second inlet 141 using a sample injection tool such as a syringe, a dropper or a pipette. Immediately after spot application, as illustrated in FIG. 60(a), quantitatively a predetermined amount of the sample liquid is injected into the first capillary cavity 140 and the second capillary cavity 156 by capillary action. Surplus sample liquid is to remain in the second inlet 141.

Figure 61A:
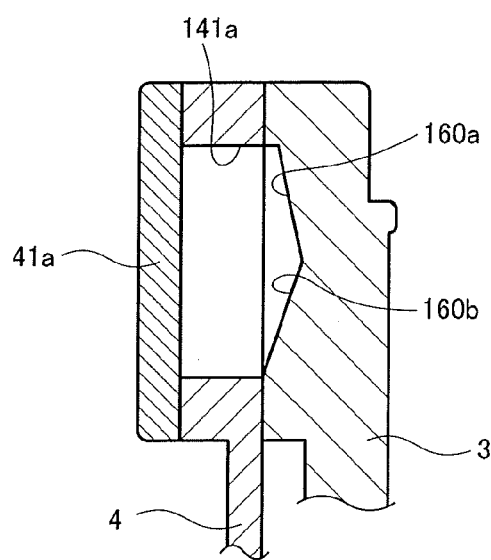
FIG. 61A is a cross-sectional view taken along A-A in FIG. 57.
Figure 61B:
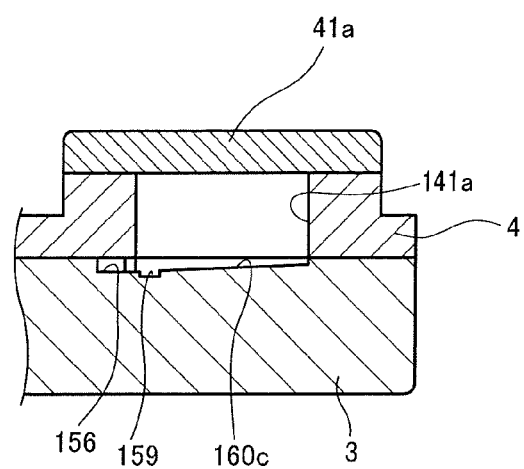
FIG. 61B is a cross-sectional view taken along B-B in FIG. 57.

At this point, as illustrated in FIGS. 61A and 61B, since the second inlet 141 includes a recess 159 and inclined faces 160a, 160b, and 160c inclined towards the second capillary cavity 156, the sample liquid spontaneously moves towards the second capillary cavity 156. As a result, the sample liquid can be transferred to the second capillary cavity 156 and the first capillary cavity 140 by a capillary force.

After the first and second capillary cavities 140 and 156 are filled with the sample liquid, by setting the analyzing device 1G in a state where the protective cap 2 is closed as illustrated in FIG. 51 onto the analyzing apparatus 100 and rotating the analyzing device 1G using the driving unit of the analyzing apparatus 100, as illustrated in FIG. 60(b), the sample liquid in the first and second capillary cavities 140 and 156 is transferred by a centrifugal force into the holding chamber 132 which holds an analytical reagent in advance. At this point, surplus sample liquid in the second capillary cavity 156 is also transferred to the overflow chamber 158 via an overflow channel 157. Since a relatively large amount of surplus sample liquid is discharged to the overflow chamber 158, a water-absorbing member such as absorbent cotton or filter paper may be positioned in the overflow chamber 158 to prevent liquid spill during disposal.

Figure 62:
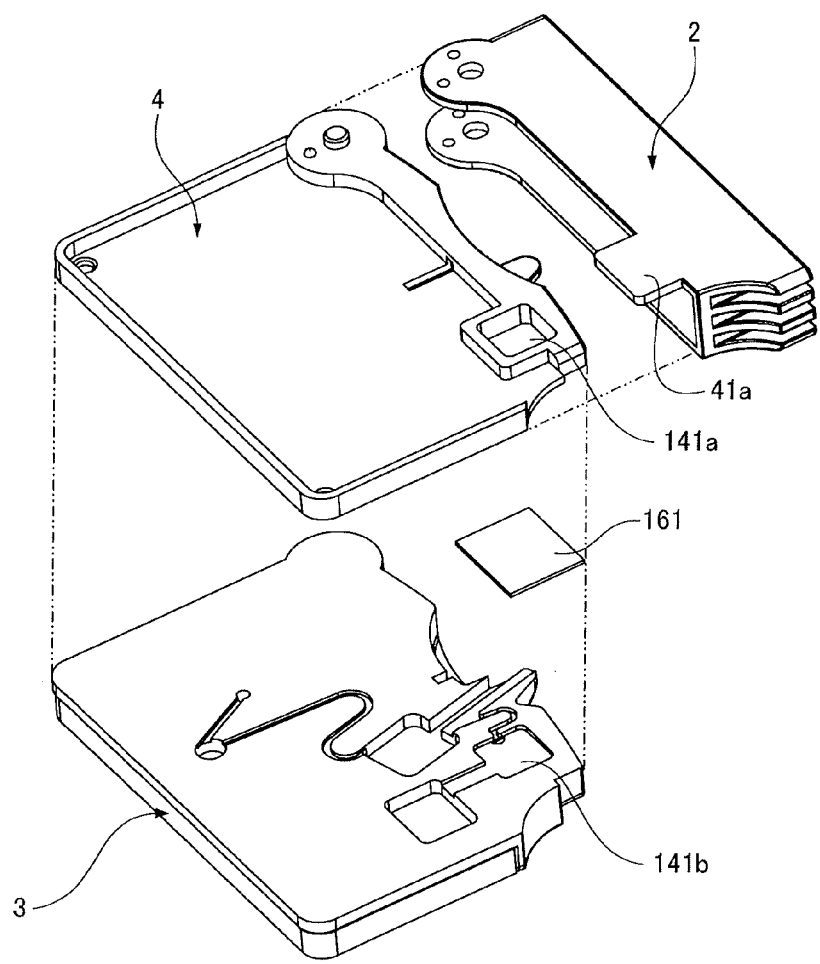
FIG. 62 is an exploded perspective view of a case where a filter is disposed at a second inlet of an analyzing device according to the eighth embodiment of the present invention.
Figure 63:
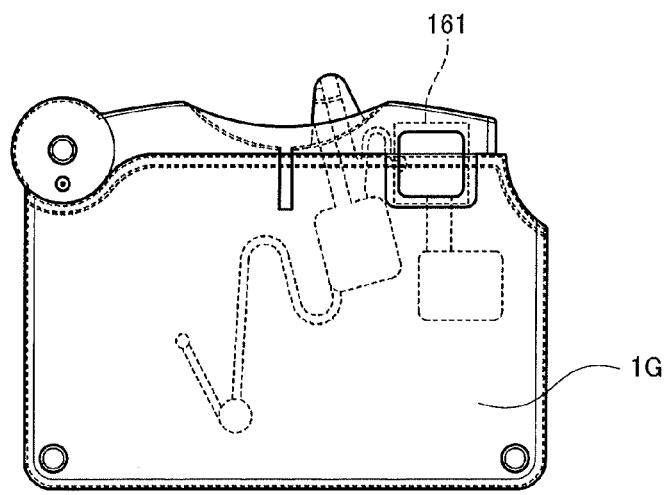
FIG. 63 is a plan view of a case where a filter is disposed at a second inlet of an analyzing device according to the eighth embodiment of the present invention.

FIGS. 62 and 63 illustrate an example in which a filter member 161 is sandwiched between the cover substrate 4 and the base substrate 3 so that the filter member 161 is disposed between the hole 141a and the recess 141b of the second inlet 141. By forming the filter member 161 with a glass filter or the like which, when using blood as a sample, only allows blood plasma to pass and blocks blood cells, the analyzing device 1G can be used for different purposes in the same mode by merely changing the reagent in the holding chamber 132, such as performing an analysis using blood plasma for blood injected from the second inlet 141 and performing an analysis using whole blood for blood spot-applied from the first inlet 13a.

Regarding subsequent transferring of a reagent liquid, since FIG. 60(c) is the same as the description of FIG. 58(c) presented above and FIG. 60(d) is the same as the description of FIG. 58(d) presented above, descriptions of FIGS. 60(c) and 60(d) will be omitted.

By providing an air open hole that communicates with a summit of the second capillary cavity 156, a quantitativity of the sample liquid to be transferred to the holding chamber 132 can be further improved.

Moreover, the motor 143, the shaft 151, couplings 144a and 144b for coupling the motor 143 and the shaft 151, the rotor 101, the rotor holding member 152, the drive control section 302 that controls the motor 143, and the central processing section 301 that controls the drive control section 302 illustrated in FIG. 55 make up a rotation driving unit.

The detector 146, the light source 147, a signal processing section 304 that converts a transmitted light detected by the detector 146 into an electrical signal, a light source control section 303 that controls outputted light of the light source 147, and the central processing section 301 that controls the signal processing section 304 and the light source control section 303 and which calculates an absorbance illustrated in FIG. 55 make up an analyzing unit.

Twelfth Embodiment

FIGS. 64 to 69 illustrate a twelfth embodiment of the present invention.

Figure 75:
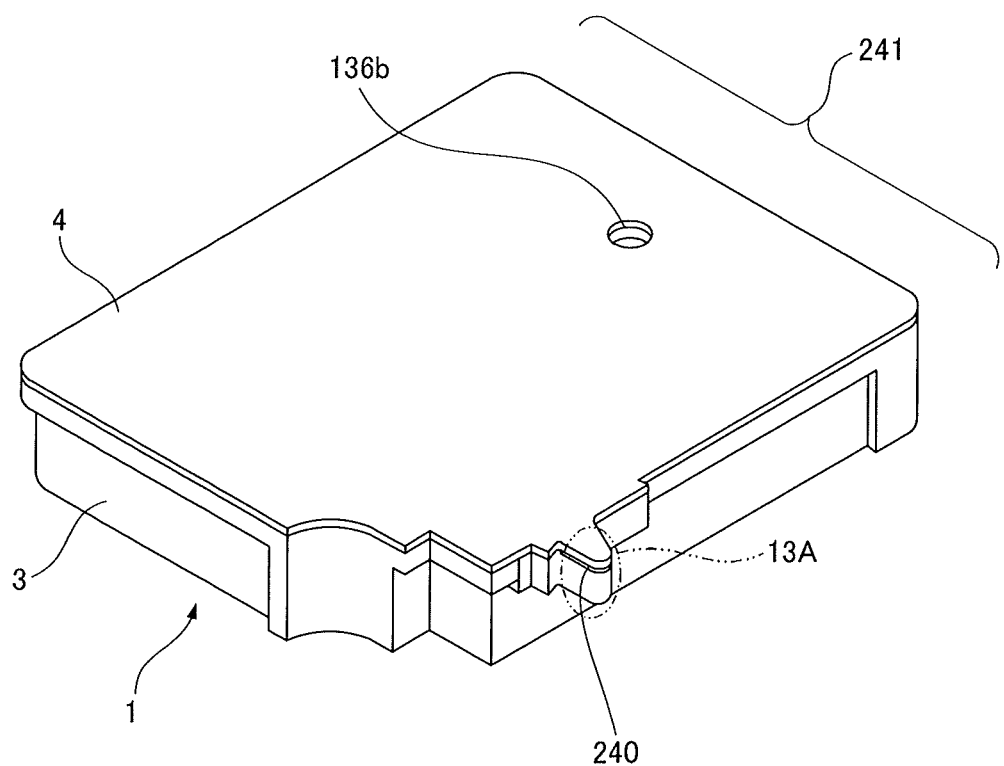
FIG. 75 is an external perspective view of an analyzing device of a type that brings an opening of a capillary channel into contact with a drop of sample liquid and performs suction by a capillary force.
Figure 76:
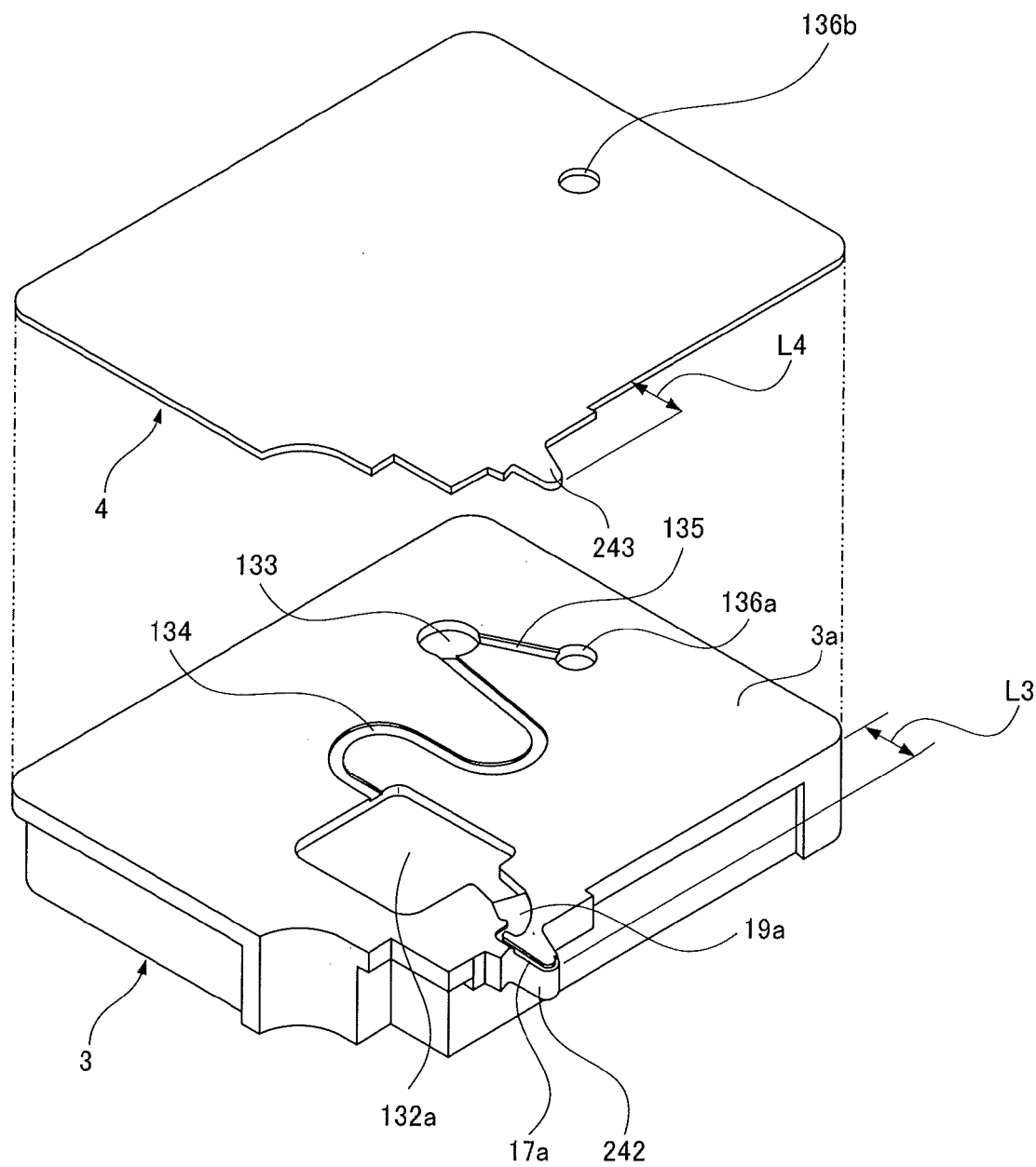
FIG. 76 is an exploded perspective view of a comparative example illustrated in FIG. 75.
Figure 77:
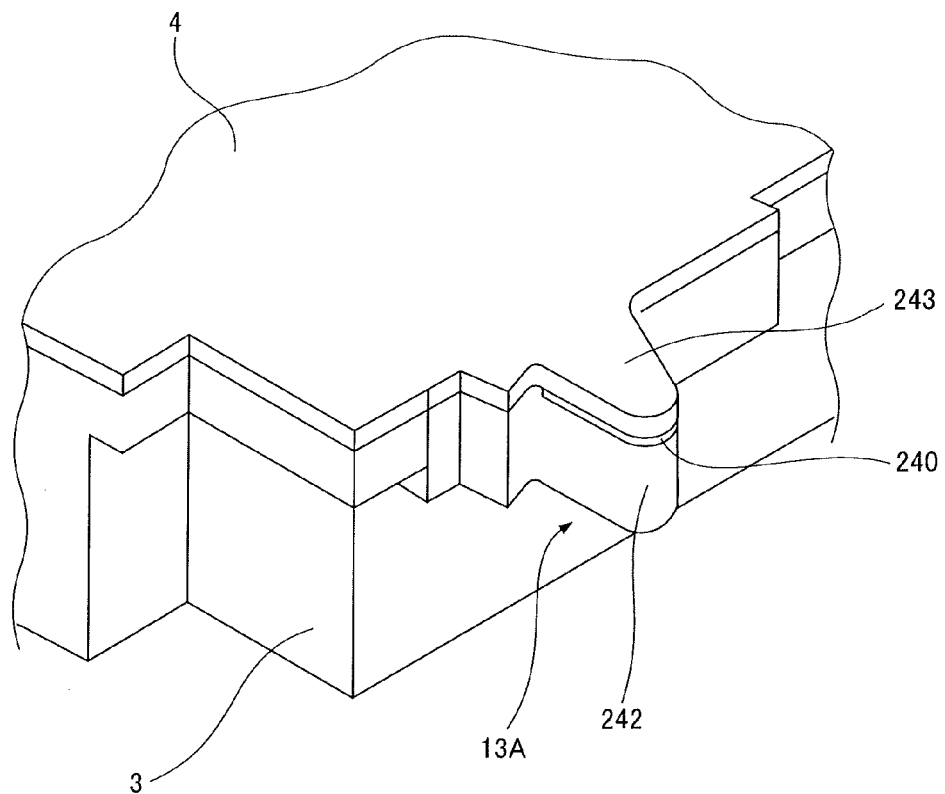
FIG. 77 is an enlarged view of substantial parts of the comparative example illustrated in FIG. 75.
Figure 78:
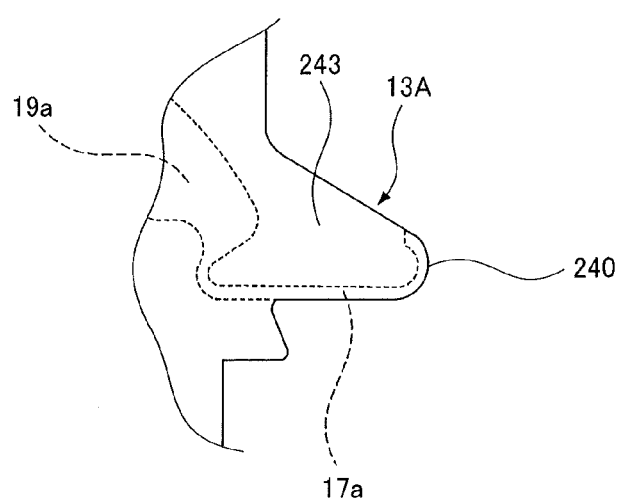
FIG. 78 is a plan view of substantial parts of the comparative example illustrated in FIG. 75.

Parts achieving the same effects as those illustrated in FIGS. 75 to 77 are to be described denoted by same reference characters.

Figure 64:
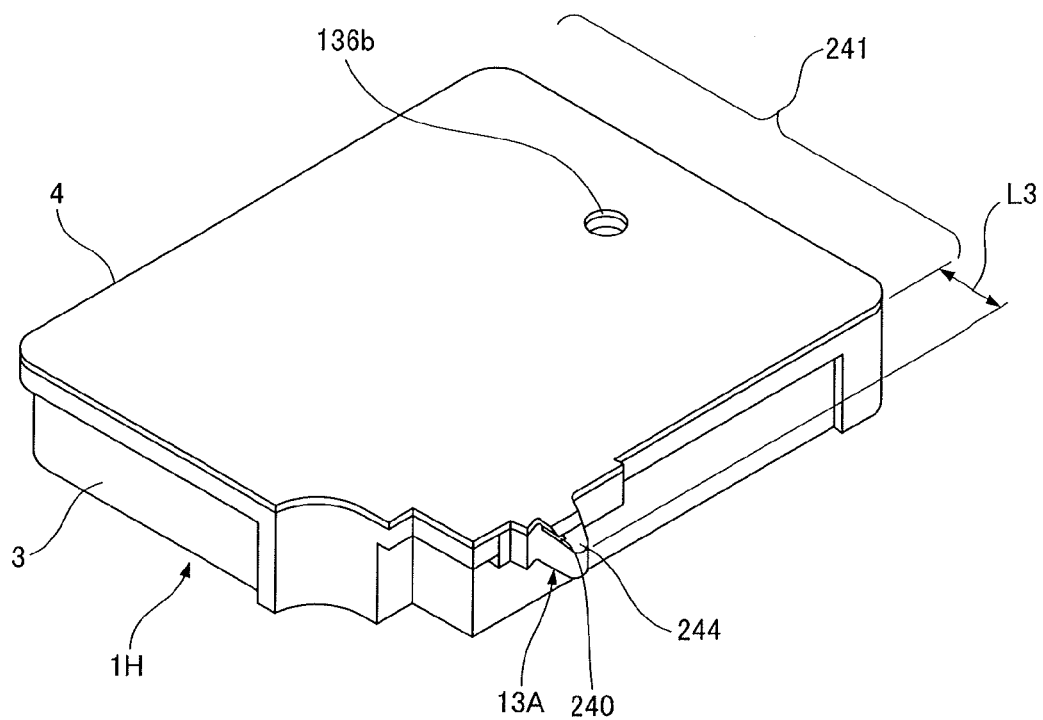
FIG. 64 is an external perspective view of an analyzing device according to the present invention (twelfth embodiment)
Figure 65:
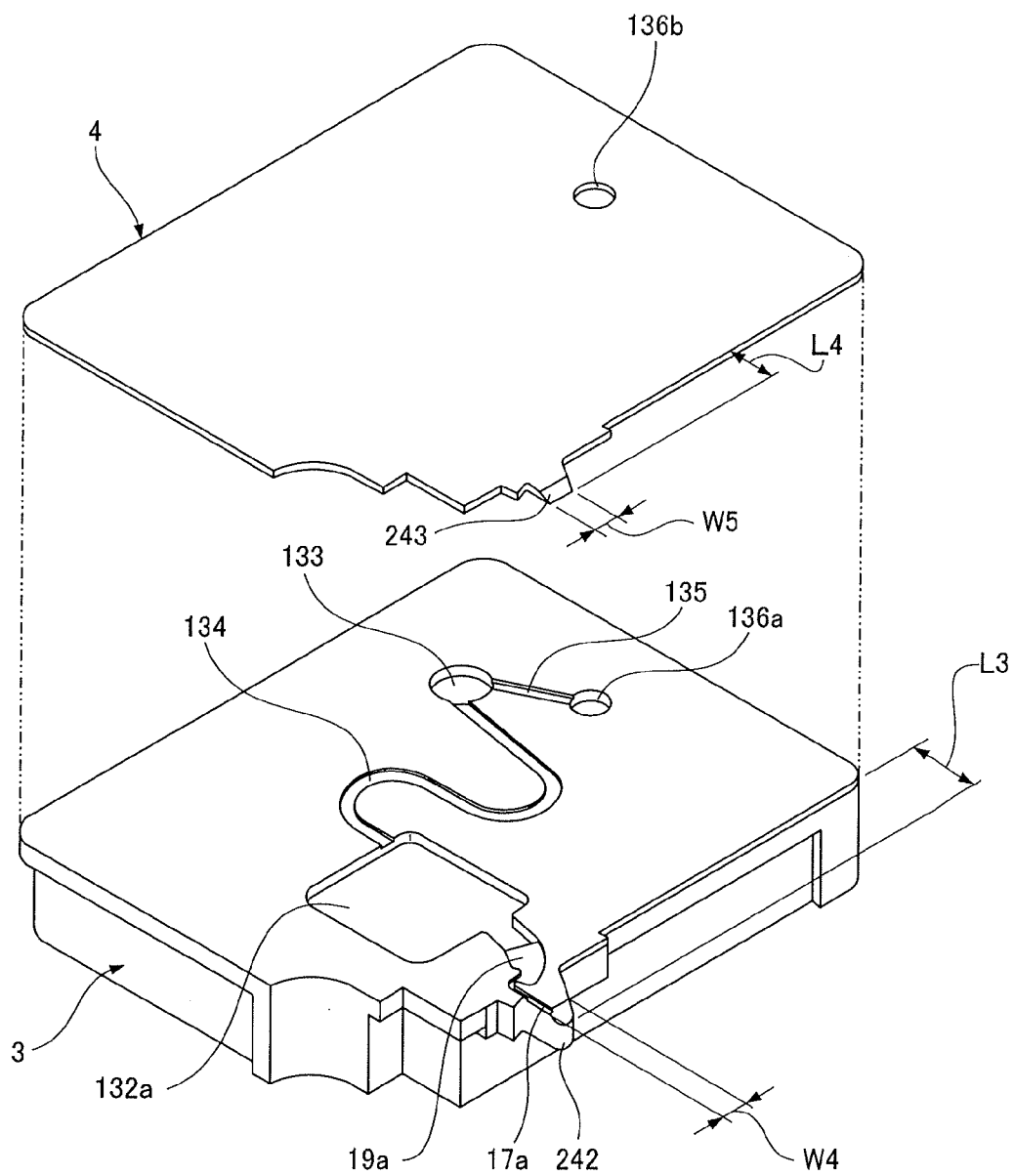
FIG. 65 is an exploded perspective view of the twelfth embodiment of the present invention.

As illustrated in FIGS. 64 and 65, an analyzing device 1H constructed by bonding together a base substrate 3 and a cover substrate 4 differs from the comparative example illustrated in FIGS. 75 and 76 in that a leading end of a spot application section 13A is formed by an inclined face 244 and an end of a supplying capillary channel 17a opens on the inclined face 244.

Figure 66:
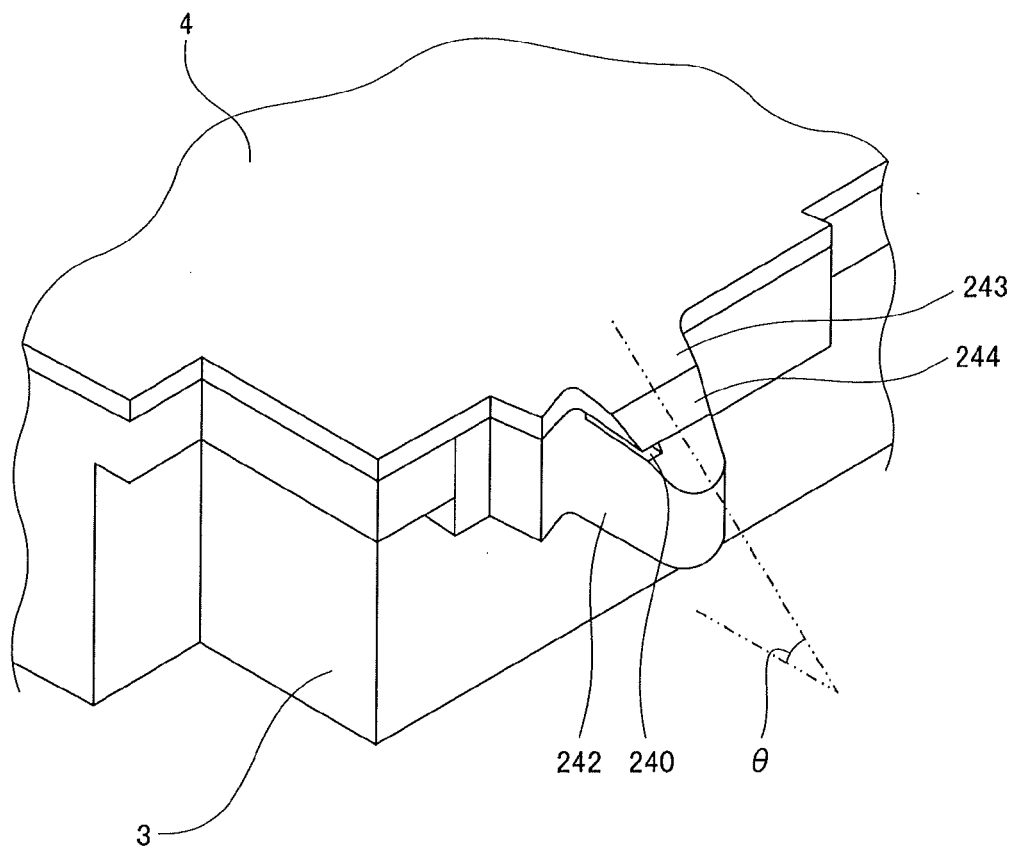
FIG. 66 is an enlarged view of substantial parts according to the twelfth embodiment of the present invention.
Figure 67:
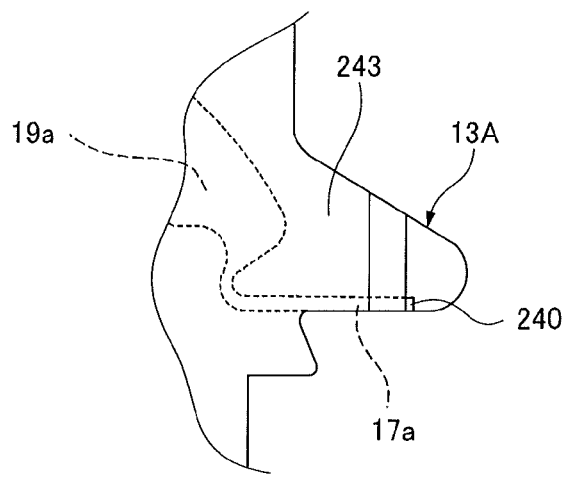
FIG. 67 is a plan view of substantial parts according to the twelfth embodiment of the present invention.

As illustrated in FIG. 65, since the leading end of the spot application section 13A is formed as the inclined face 244, in the spot application section 13A formed by a bonding of a protrusion 242 of the base substrate 3 and a protrusion 243 of the cover substrate 4, a protrusion length L4 of the protrusion 243 is smaller than a protrusion length L3 of the protrusion 242. In addition, as illustrated in FIG. 66, an angle θ of the inclined face 244 is acute. Specifically, when blood is used as a sample liquid, the angle θ preferably ranges from 30 degrees to 45 degrees. A situation where an opening 240 that is an end of the supplying capillary channel 17a is opened on the inclined face 244 is illustrated in FIGS. 66 and 67.

Moreover, in the present twelfth embodiment, a width W4 of the protrusion 242 of the base substrate 3 in a vicinity of the opening 240 and a width W5 of the protrusion 243 of the cover substrate 4 in a vicinity of the opening 240 are formed so as to equal each other.

In addition, wall faces of the supplying capillary channel 17a, a holding chamber 19a, and channels 134 and 135 have been subjected to hydrophilic treatment. Methods of hydrophilic treatment include a surface treatment method using plasma, corona, ozone, or an active gas such as fluorine, and surface treatment with a surfactant or a hydrophilic polymer. In this case, hydrophilicity refers to a contact angle with water that is less than 90 degrees.

As for specific dimensions of the analyzing device 1H, a thickness of the base substrate 3 is 15 mm, a thickness of the cover substrate 4 is 1 mm, and when the analyzing device 1H is arranged as an approximately 80 mm square, a depth of the holding chamber 19a is 0.1 mm. A depth of a reagent chamber 132a is formed deeper than a depth of the holding chamber 19a so as to range from 0.3 mm to 0.5 mm. Due to such a configuration, blood injected into the holding chamber 19a does not proceed to the reagent chamber 132a by a capillary force alone and the sample liquid is transferred utilizing a centrifugal force obtained by rotating the analyzing device 1H.

While depths of the supplying capillary channel 17a, the holding chamber 19a, and the channels 134 and 135 are formed so as to be equal to or greater than 0.02 mm and less than 0.3 mm, such dimensions are not restrictive as long as a sample liquid flows by a capillary force. Generally, since a liquid such as blood is to be measured and analyzed, depths are desirably set so as to equal to or greater than 0.02 mm and less than 0.3 mm. In addition, while the depths of the reagent chamber 132*a* and the measurement chamber 133 are formed so as to range from 0.3 mm to 0.5 mm, the depths can be adjusted according to a sample solution volume and conditions for measuring absorbance (optical path length, measured wavelength, reaction concentration of sample solution, reagent type, and the like). Subsequently, a sample liquid transferred to the measurement chamber 133 is optically measured.

The width W4 of the protrusion 242 of the base substrate 3 and the width W5 of the protrusion 243 of the cover substrate 4 are set so as to range from 3 to 5 mm, and a protrusion length L3 of the spot application section 13A from an analyzing device main body 241 is set to 8 mm.

Figure 68:
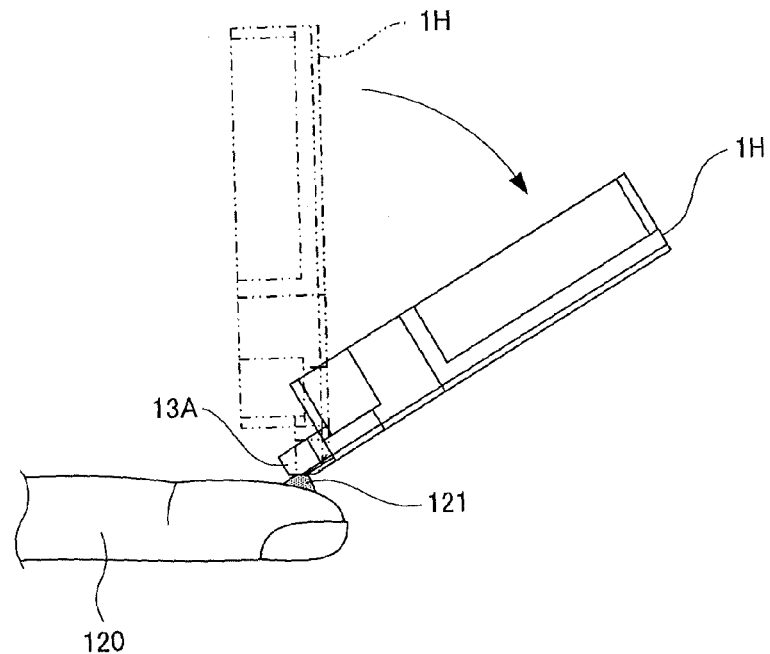
FIG. 68 is an explanatory diagram of an in-use state according to the twelfth embodiment of the present invention.

Due to such a configuration, when performing an analysis of blood as a sample liquid, as is the case with the analyzing device 1H depicted by an imaginary line in FIG. 68, even if the analyzing device 1H is set to a vertical posture and a leading end of the spot application section 13A is brought into contact with a blood drop 121 on a fingertip 120 of a testee, since the opening 240 on one end of the supplying capillary channel 17*a* that is opened on the inclined face 244 does not come into contact with the blood drop 121, blood is not suctioned from the supplying capillary channel 17*a* to the holding chamber 19*a*.

Therefore, by inclining the analyzing device 1H as depicted by a solid line in FIG. 68 and bringing the inclined face 244 alongside the fingertip 120, the opening 240 that opens on the inclined face 244 comes into contact with the blood drop 121 and blood is suctioned from the supplying capillary channel 17*a* to the holding chamber 19*a*.

Figure 69:
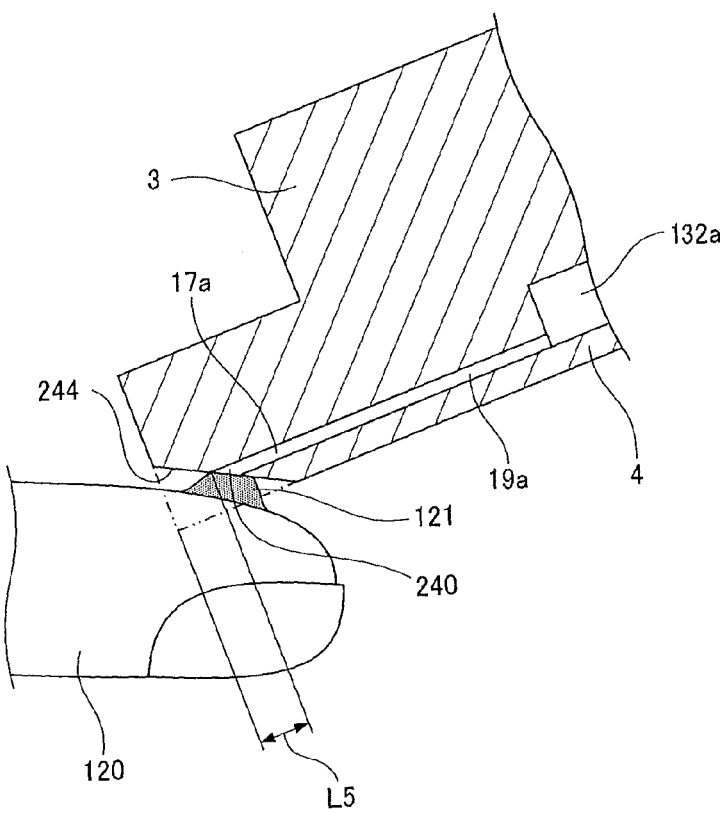
FIG. 69 is an enlarged view of an in-use state according to the twelfth embodiment of the present invention.
Figure 79:
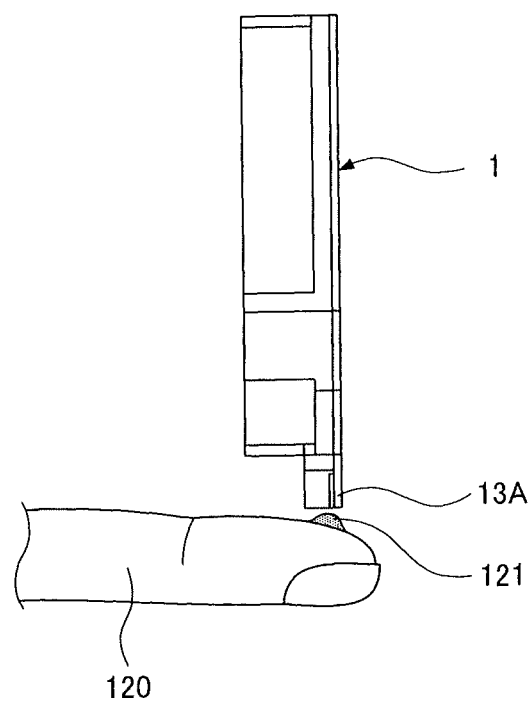
FIG. 79 is an explanatory diagram of an in-use state of the comparative example illustrated in FIG. 75.

As shown, by forming the shape of the leading end of the spot application section 13A as the inclined face 244, as illustrated in FIG. 69, the length of the supplying capillary channel 17*a* is reduced by a distance L5 in comparison to the comparative example illustrated in FIGS. 75 and 76. In addition, since an angle formed by the supplying capillary channel 17*a* and the holding chamber 19*a* during suction is set so as to range from 30 degrees to 45 degrees which is the same as the angle θ of the inclined face 244, a magnitude of gravity affecting the speed of suctioned blood can be reduced and a period of time required to sample a fixed amount of blood into the holding chamber 19*a* can be shortened in comparison to a case such as the comparative example illustrated in FIG. 79 in which the angle formed by the supplying capillary channel 17*a* and the holding chamber 19*a* is a right angle.

Accordingly, occurrences of situations of insufficiency where blood held in the holding chamber 19*b* fails to reach a fixed amount can be reduced, and an accurate analysis can be performed when blood held in the holding chamber 19*a* is transferred towards the measurement chamber 133 by a centrifugal force and a solution in the measurement chamber 133 is optically accessed and analyzed.

Thirteenth Embodiment

Figure 70:
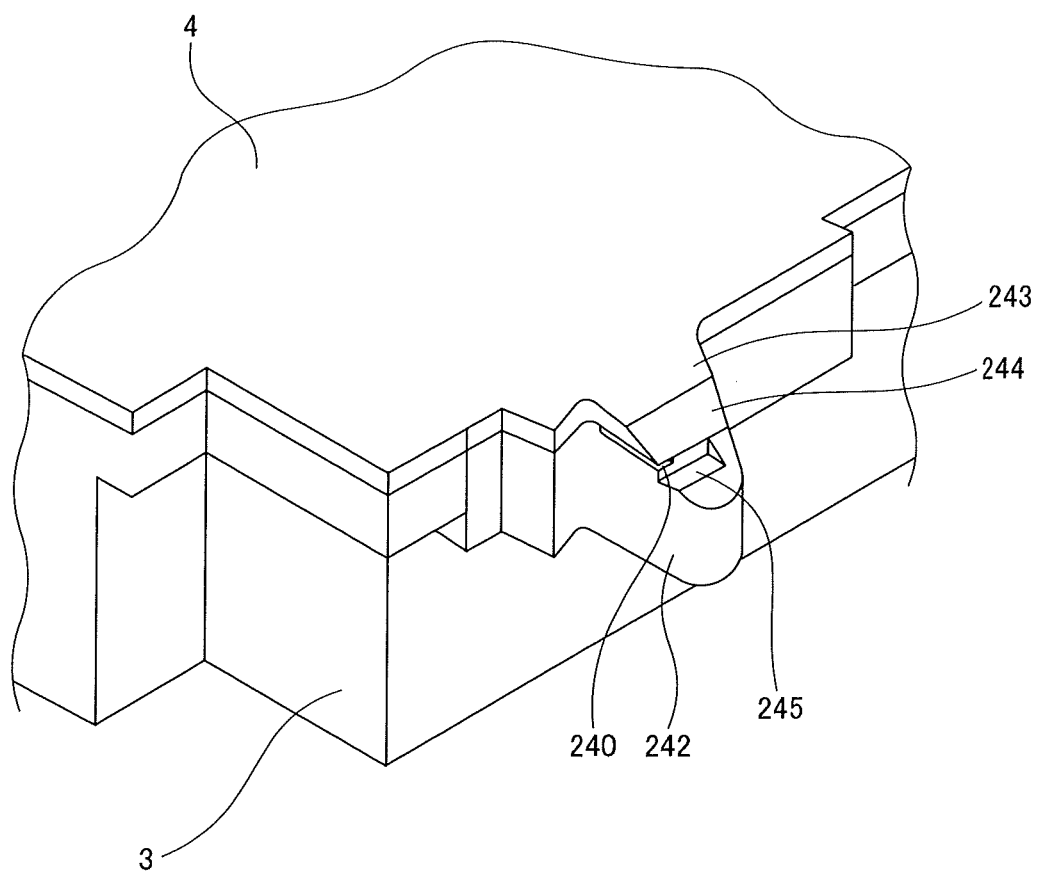
FIG. 70 is an enlarged perspective view of substantial parts of an analyzing device according to the present invention (thirteenth embodiment)
Figure 71:
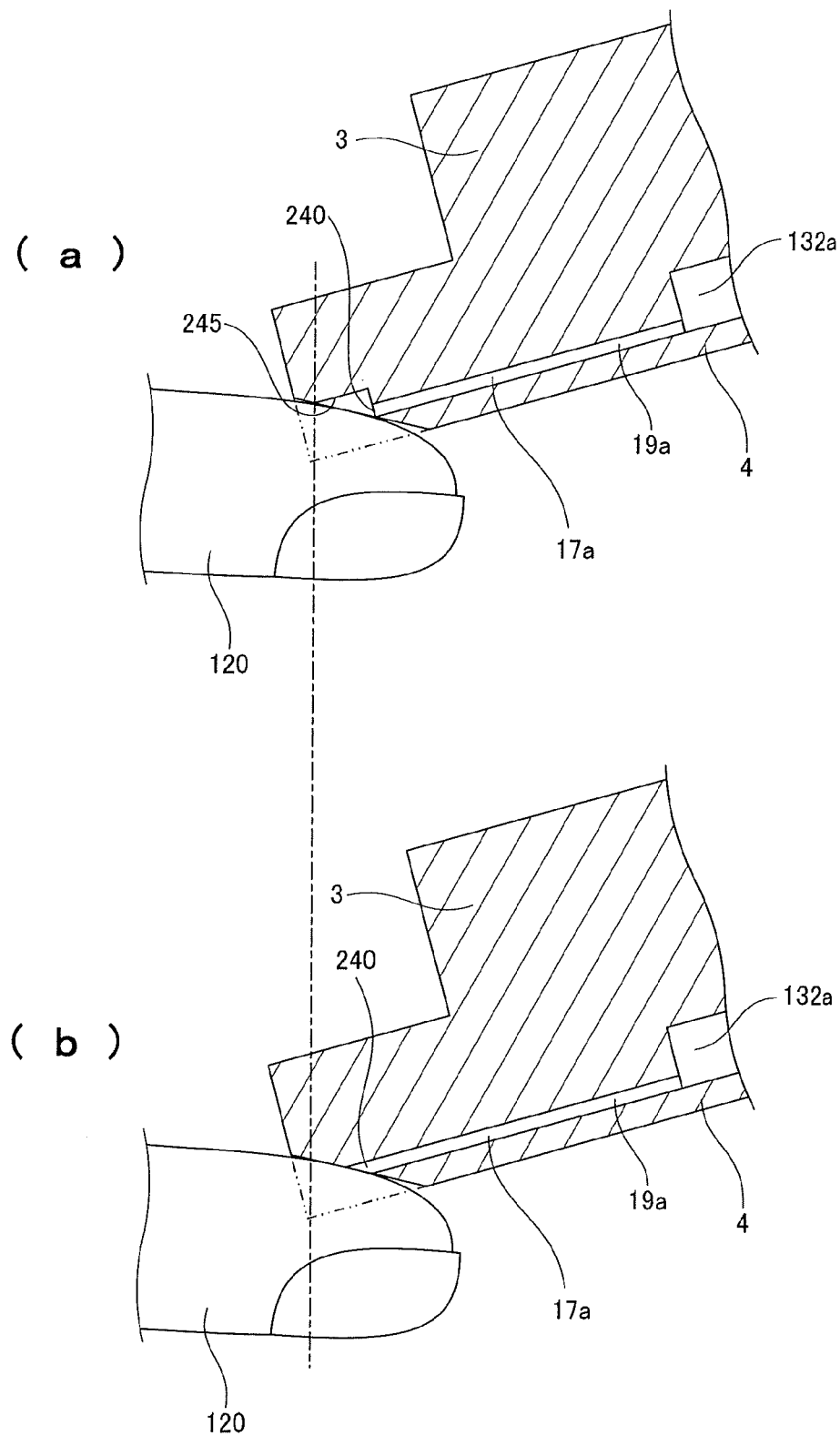
FIG. 71 is an enlarged cross-sectional view of an in-use state according to the thirteenth embodiment of the present invention and an enlarged cross-sectional view of an in-use state (according to the twelfth embodiment)

FIGS. 70 and 71 illustrate a thirteenth embodiment of the present invention.

In the case of the twelfth embodiment, it is conceivable that when the analyzing device 1H is excessively pressed against the fingertip 120 of a testee as illustrated in FIG. 71(*b*), the opening 240 opened on the inclined face 244 ends up being closed by the fingertip 120 and the suction speed of blood declines. In contrast, a thirteenth embodiment differs from the twelfth embodiment in that, as illustrated in FIG. 70, a closure prevention recess 245 that communicates with an opening 240 is formed on the inclined face 244. Specifically, while a cover substrate 4 is the same as in the twelfth embodiment, the closure prevention recess 245 is formed on a base substrate 3.

Due to such a configuration, even when the analyzing device 1H is excessively pressed against a fingertip 120 of a testee, as illustrated in FIG. 71(*a*), the closure prevention recess 245 acts to prevent the fingertip 120 from coming into contact with the opening 240. Therefore, even in this case, a decline in the suction speed of blood does not occur.

Fourteenth Embodiment

Figure 72:
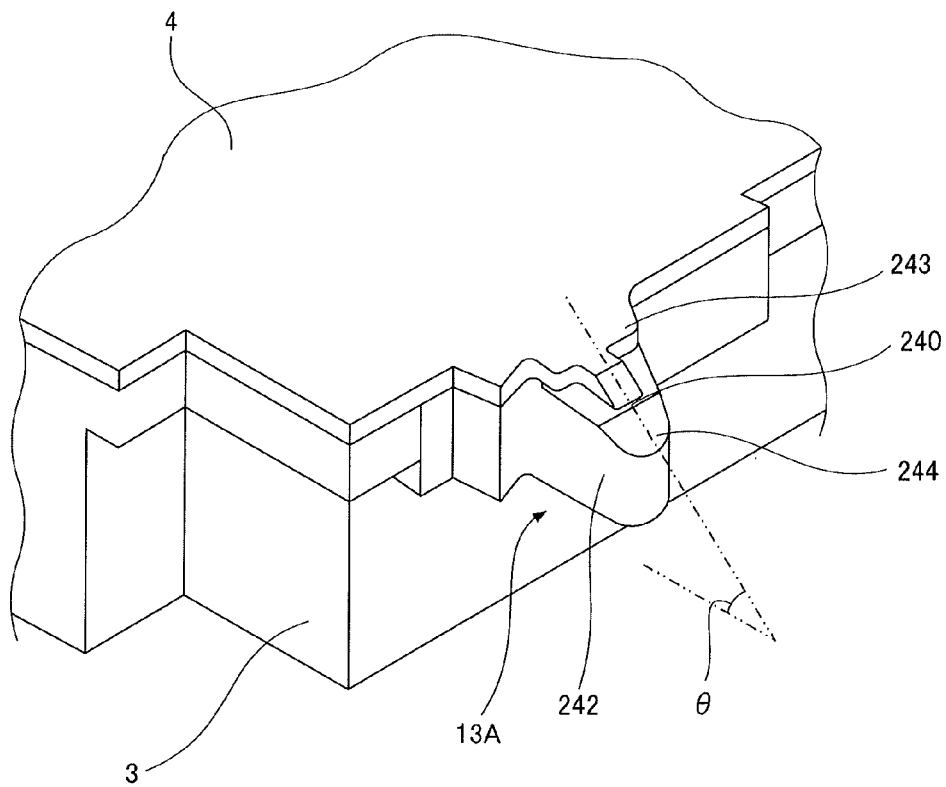
FIG. 72 is an enlarged perspective view of substantial parts of an analyzing device according to the present invention (fourteenth embodiment)
Figure 73:
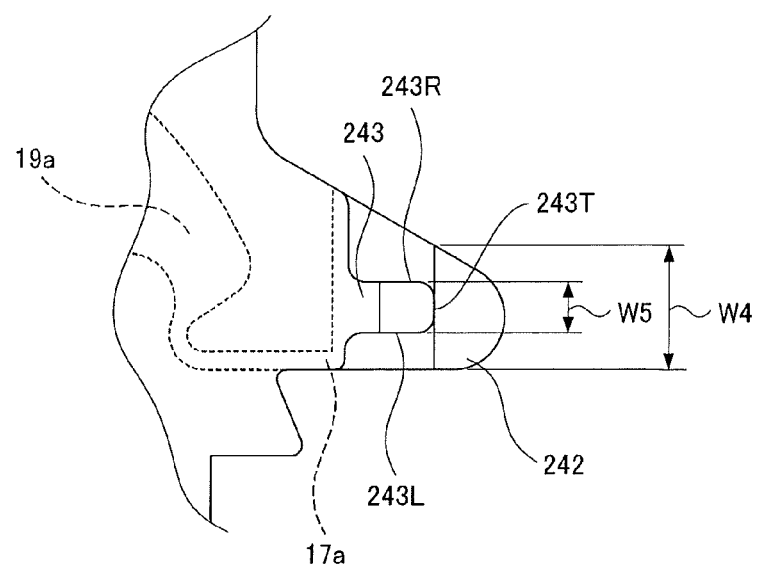
FIG. 73 is a plan view of substantial parts according to the fourteenth embodiment of the present invention.
Figure 74:
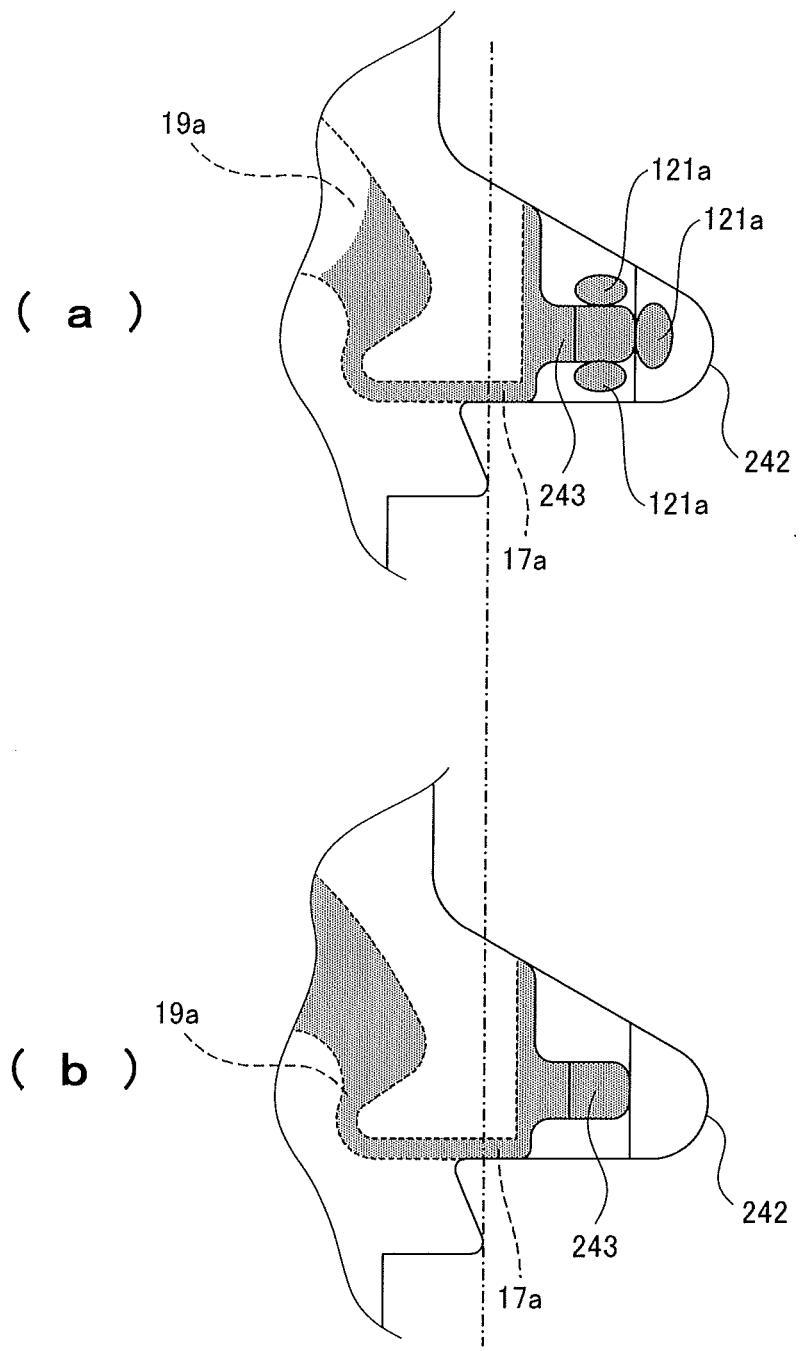
FIG. 74 is a plan view of an in-use state according to the fourteenth embodiment of the present invention.

FIGS. 72 to 74 illustrate a fourteenth embodiment of the present invention.

In the twelfth embodiment, since the inclined face 244 is formed at the spot application section 13A, an area wetted by blood when the inclined face 244 is brought into contact with the blood drop 121 increases in comparison to a comparative example illustrated in FIG. 77 and blood not suctioned by a capillary force into the supplying capillary channel 17*a* remains on the leading end of the base substrate 3 and solidifies. However, the present fourteenth embodiment is capable of reducing blood remaining on the leading end of the base substrate 3.

In the twelfth embodiment, the width W4 of the protrusion 242 of the base substrate 3 and the width W5 of the protrusion 243 of the cover substrate 4 are formed so as to equal each other. However, in the present fourteenth embodiment, while an incline of the inclined face 244 of the spot application section 13A is the same, a width W5 of a protrusion 243 of a cover substrate 4 in a vicinity of the opening 240 is formed narrower than a width W4 of a protrusion 242 of a base substrate 3. In FIG. 72, a leading end of the protrusion 243 of the cover substrate 4 is positioned in a vicinity of the center of the protrusion 242 of the base substrate 3. As illustrated in FIG. 73, the one end of the supplying capillary channel 17*a* is opened on both sides 243R and 243L of the protrusion 243 and at a leading end 243T of the protrusion 243.

Due to such a configuration, blood is first suctioned by a capillary force into a holding chamber 19*a* via a supplying capillary channel 17*a* as illustrated in FIG. 74(*a*), and a major portion of blood 121*a* remaining in a portion of the inclined face 244 of the protrusion 242 of the base substrate 3 can be suctioned by a capillary force as illustrated in FIG. 74(*b*) via the supplying capillary channel 17*a* formed between a leading end of the protrusion 243 of the cover substrate 4 whose leading end is narrower than the protrusion 242 of the base substrate 3 and the protrusion 242 of the base substrate 3.

In the twelfth, thirteenth, and fourteenth embodiments, the more acute the incline of the spot application section, the more the analyzing device 1H can be inclined horizontally, which is effective in reducing filling time. While an incline of the spot application section 13A ranging from 30 to 45 degrees has been confirmed effective when blood is used as a sample liquid, the angle is not restricted thereto if an angle of 45 degrees or greater is effective in regards to filling time depending on the sample liquid.

While the case of an analyzing device to be used for reading involving optically accessing a solution in the measurement chamber 133 has been described as an example in the twelfth, thirteenth, and fourteenth embodiments, an analyzing device to be used for reading involving accessing a solution in the measurement chamber 133 provided with an electrochemical sensor can be similarly implemented.

In addition, while the case where blood suctioned by a capillary force into the holding chamber 19a is transferred by a centrifugal force to the measurement chamber 133 has been described as an example in the twelfth, thirteenth, and fourteenth embodiments, even in a case of an analyzing device to be used for reading involving directly suctioning a sample liquid from the opening 240 into a measurement chamber having a capillary force and accessing a test object in the measurement chamber, the fixed amount of blood can be sampled and an accurate analysis can be realized by forming a shape of a leading end of the spot application section 13A as the inclined face 244 as described in the twelfth, thirteenth, and fourteenth embodiments.

Fifteenth Embodiment

In a case where a spot application section of an analyzing device is directly brought into contact with a blood drop 121 to suction and sample blood by a capillary force, an insufficient amount of blood is sampled to an analyzing device when the contact time of the spot application section to the blood drop is short. Fifteenth to twenty-first embodiments will describe, based on specific examples, specific configurations in which analyzing devices according to the respective embodiments described above are provided with a confirmation window that enables a sampling amount to be visually confirmed.

FIGS. 80 to 85 illustrate a fifteenth embodiment of the present invention.

Figure 80:
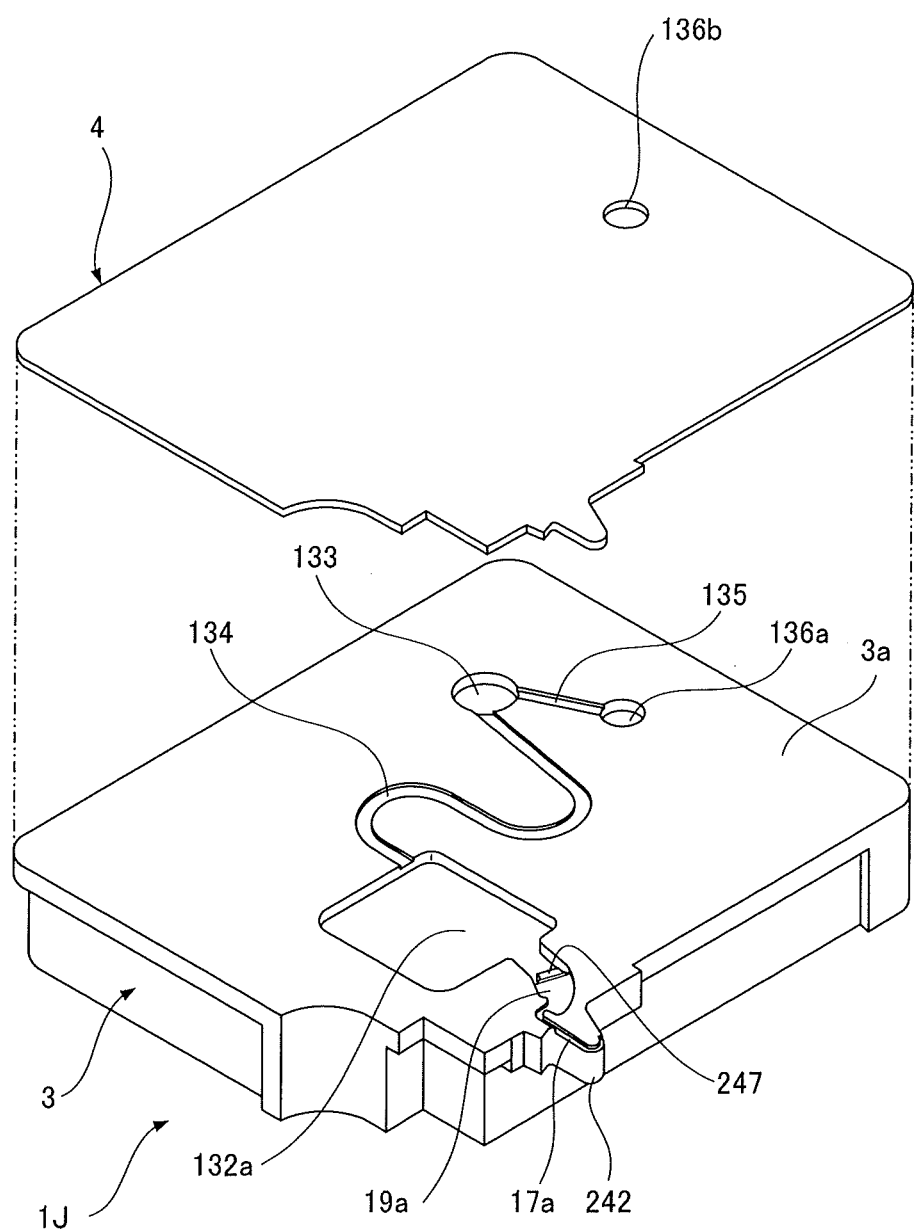
FIG. 80 is an external perspective view of an analyzing device according to the present invention (fifteenth embodiment)

An analyzing device 1J is constructed by a bonding of a base substrate 3 and a cover substrate 4 illustrated in FIG. 80. Specifically, the base substrate 3 and the cover substrate 4 are molded from a transparent synthetic resin such as acrylic resin.

An internal recess to become a holding chamber 19a, a reagent chamber 132a, a channel 134, a measurement chamber 133, and a channel 135 is formed on a bonding face 3a of the base substrate 3 with the cover substrate 4. The reagent chamber 132a holds an analytical reagent (not shown). The cover substrate 4 molded from a transparent synthetic resin covers respective opening faces of the internal recess so as to form a cavity having a predetermined gap so as to realize respective functions such as transferring of a sample liquid by a capillary force and retention of a predetermined liquid volume. Reference character 136b denotes an air open hole formed on the cover substrate 4 in correspondence to a position of an outlet port 136a on a side of the base substrate 3.

In addition, wall faces of a supplying capillary channel 17a, the holding chamber 19a, and the channels 134 and 135 have been subjected to hydrophilic treatment. Methods of hydrophilic treatment include a surface treatment method using plasma, corona, ozone, or an active gas such as fluorine, and surface treatment with a surfactant or a hydrophilic polymer. In this case, hydrophilicity refers to a contact angle with water that is less than 90 degrees.

As for specific dimensions of the analyzing device 1J, a thickness of the base substrate 3 is 15 mm, a thickness of the cover substrate 4 is 1 mm, and when the analyzing device 1J is arranged as an approximately 80 mm square, a depth of the holding chamber 19a is formed so as to be equal to or greater than 0.02 mm and less than 0.3 mm. The depth of the holding chamber 19a when measuring and analyzing a liquid such as blood is preferably 0.1 mm. A depth of the reagent chamber 132a is formed deeper than the depth of the holding chamber 19a so as to be greater than 0.3 mm and equal to or less than 0.5 mm. Due to such a configuration, blood injected into the holding chamber 19a does not proceed to the reagent chamber 132a by a capillary force alone and the sample liquid is transferred utilizing a centrifugal force obtained by rotating the analyzing device 1J.

While depths of the supplying capillary channel 17a, the holding chamber 19a, and the channels 134 and 135 are formed so as to be equal to or greater than 0.02 mm and less than 0.3 mm, such dimensions are not restrictive as long as a sample liquid flows by a capillary force. In addition, while the depths of the reagent chamber 132a and the measurement chamber 133 are formed so as to be greater than 0.3 mm and equal to or less than 0.5 mm, the depths can be adjusted according to a sample solution volume and conditions for measuring absorbance (optical path length, measured wavelength, reaction concentration of sample solution, reagent type, and the like). Subsequently, a sample liquid transferred to the measurement chamber 133 is optically measured.

Figure 81:
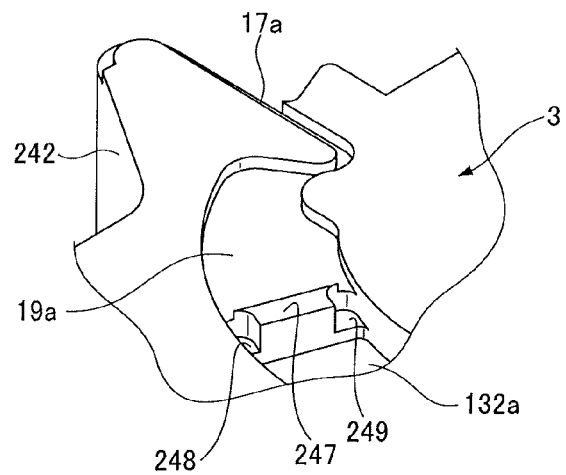
FIG. 81 is an enlarged perspective view of substantial parts of a base substrate according to the fifteenth embodiment of the present invention.
Figure 82:
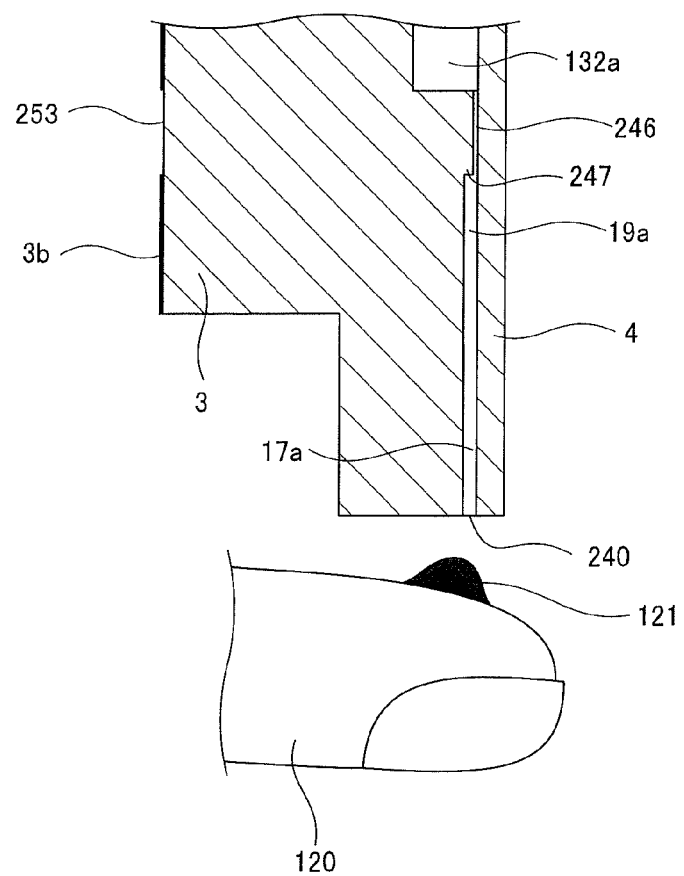
FIG. 82 is an explanatory diagram of an in-use state according to the fifteenth embodiment of the present invention.

The spot application section 13A is formed by a bonding of a protrusion 242 of the base substrate 3 and a protrusion 243 of the cover substrate 4. As illustrated in FIGS. 81 and 82, a leading end of the spot application section 13A and the holding chamber 19a is connected by the supplying capillary channel 17a formed between the base substrate 3 and the cover substrate 4.

When blood is used as a sample liquid, all of gaps of the supplying capillary channel 17a and most gaps of the holding chamber 19a are formed so as to be, for example, less than 0.3 mm, and a gap of the reagent chamber 132a is formed so as to be greater than 0.3 mm and equal to or less than 0.5 mm.

The only difference from the comparative example illustrated in FIGS. 75 and 76 is as described below.

Figure 83:
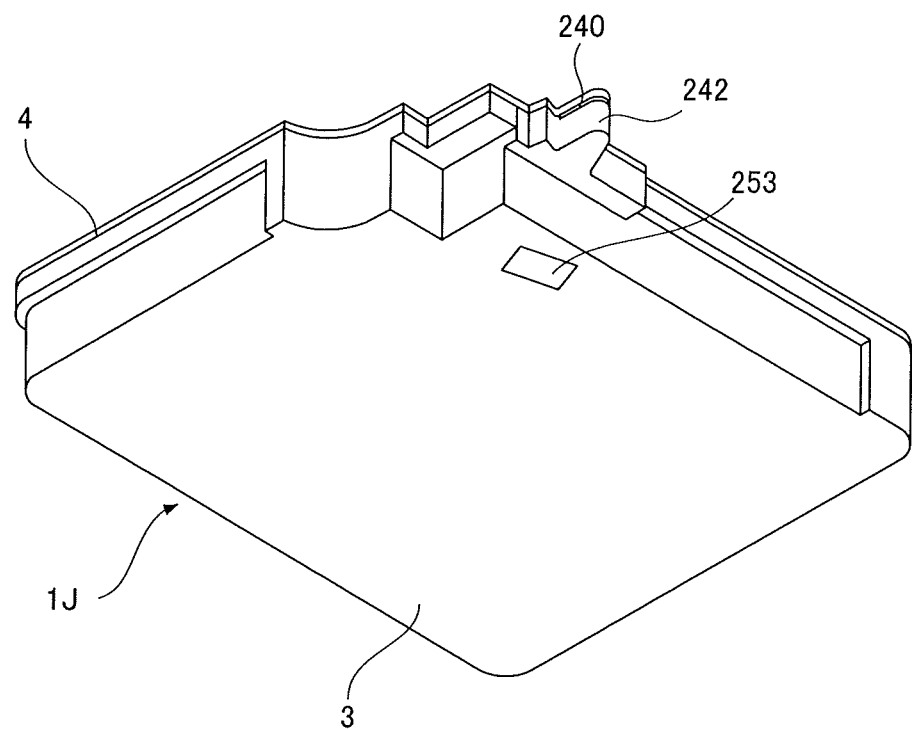
FIG. 83 is an external perspective view of an analyzing device according to the fifteenth embodiment of the present invention.
Figure 84:
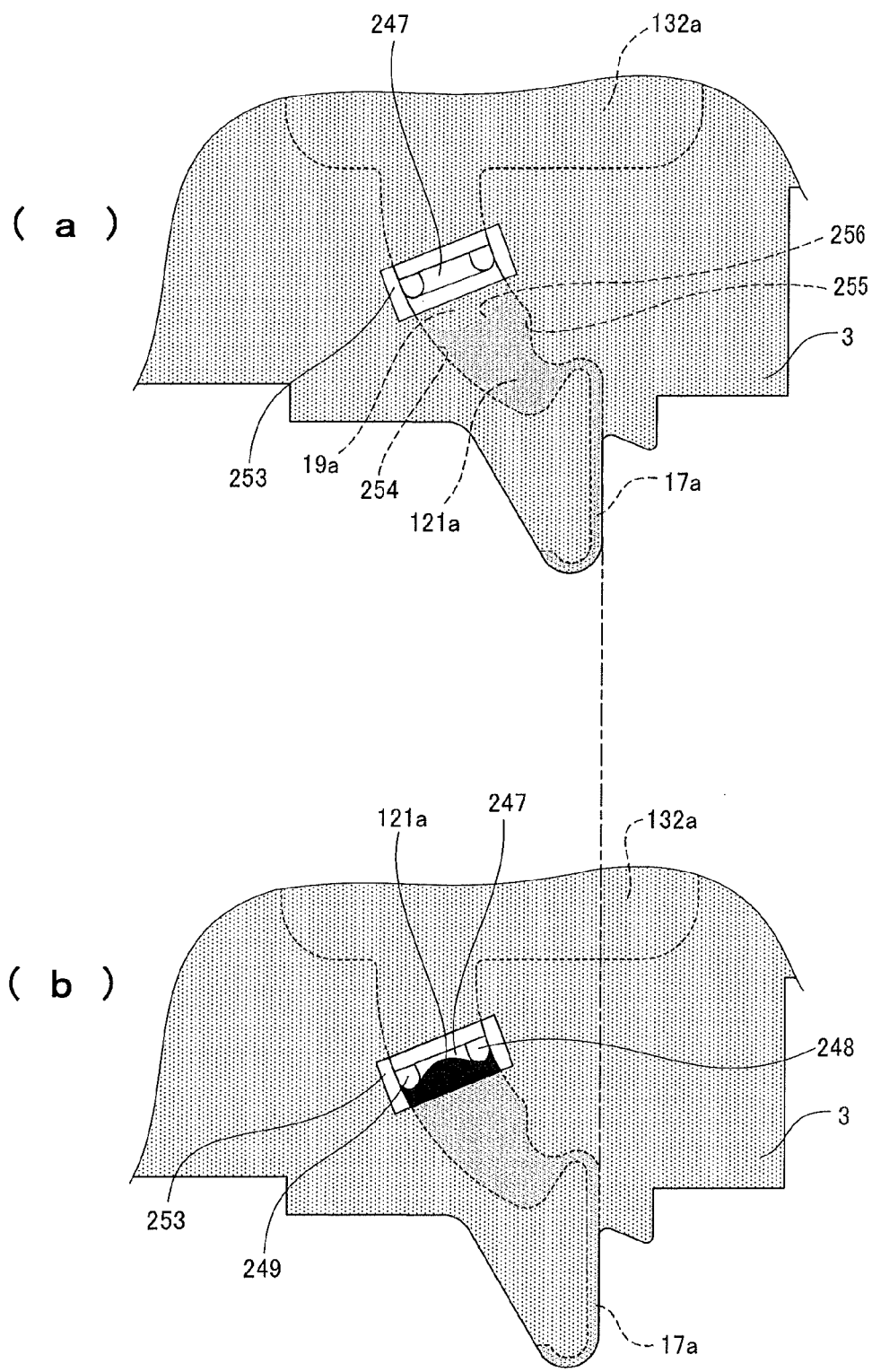
FIG. 84 is an enlarged view of a vicinity of a confirmation window in an in-use state according to the fifteenth embodiment of the present invention.
Figure 85:
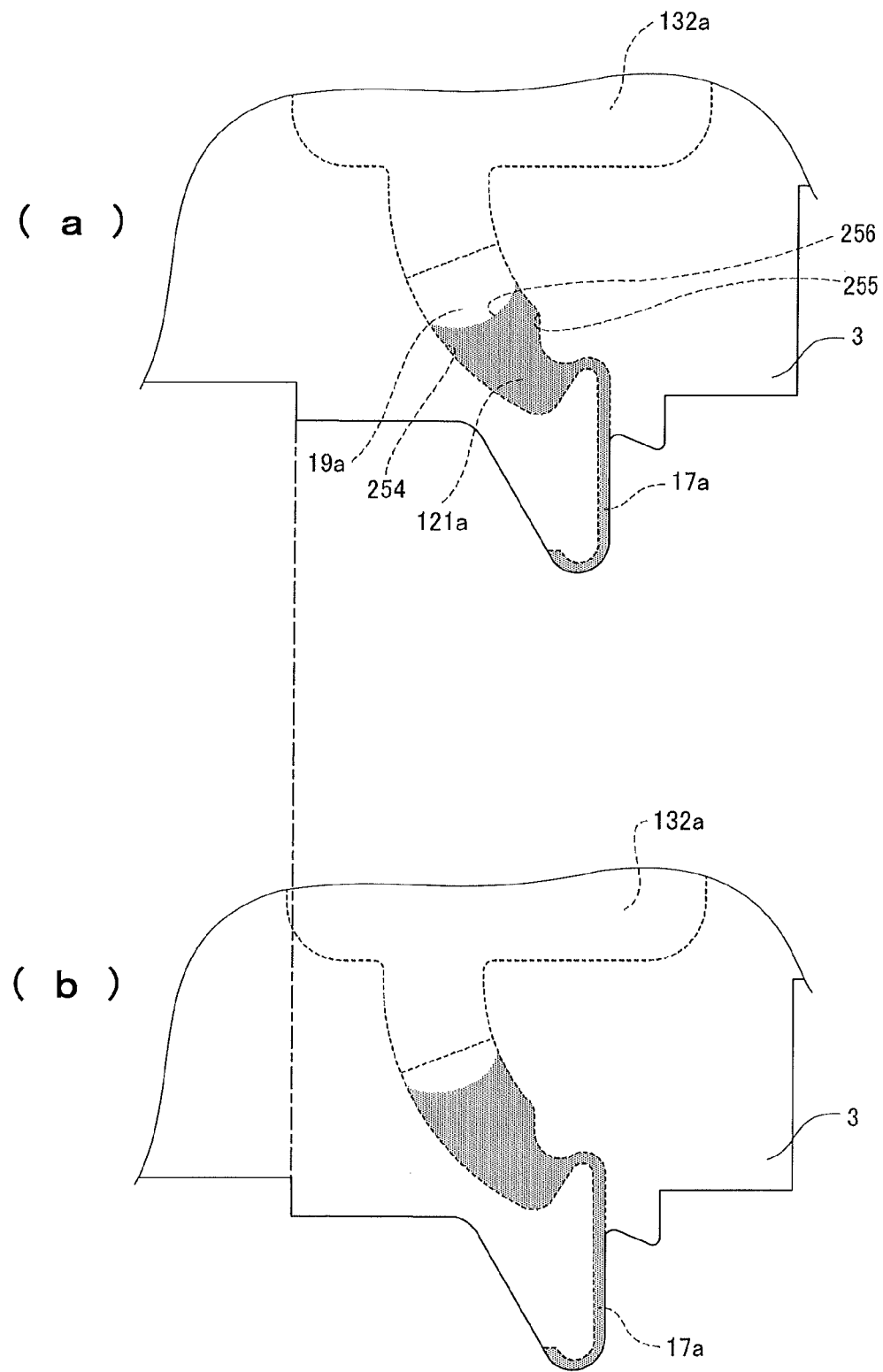
FIG. 85 is an enlarged view of an in-use state of a comparative example.

The difference from the comparative example is that, as illustrated in FIGS. 82 and 83, a protrusion 247 that forms a filling confirmation region 246 having a smaller gap (0.1 mm) than the capillary force-generating gap (0.3 mm) of the holding chamber 19a is formed on the base substrate 3 on a trailing end of the holding chamber 19a. Recesses 248 and 249 are formed on both sides of the protrusion 247.

In addition, as illustrated in FIGS. 82 and 83, a confirmation window 253 is formed in correspondence to the filling confirmation region 246 on a face 3b on an opposite side of the bonding face 3a of the base substrate 3. A periphery of the confirmation window 253 on the face 3b of the base substrate 3 is subjected to, for example, surface texturing so as to reduce translucency in comparison to the confirmation window 253. Specifically, a pearskin pattern is applied to the surface.

Due to such a configuration, when performing an analysis of blood as a sample liquid, by setting the analyzing device 1J to a vertical posture and bringing the spot application section 13A into contact with a blood drop 121 on a fingertip 120 of a testee, as illustrated in FIG. 84(a), capillary forces of the supplying capillary channel 17a and the holding chamber 19a initially cause blood 121a as a sample to flow along wall faces 254 and 255 of the holding chamber 19a to be suctioned in a shape in which a central part 256 lags behind sides of the wall faces 254 and 255. In such a state where suction is in progress, suctioned blood cannot be confirmed through the confirmation window 253.

Once suctioned blood reaches a fixed amount, the suctioned blood reaches the filling confirmation region 246 as illustrated in FIG. 84(b). By forming the protrusion 247 at the filling confirmation region 246, a shape of a leading end of the suctioned blood changes from a shape where the central part 256 lags behind as illustrated in FIG. 84(a) to a shape where the central part 256 protrudes towards the reagent chamber 132a so as to enable confirmation through the confirmation window 253. Therefore, it can be clearly recognized that a sampled amount has reached a fixed amount.

Figure 106:
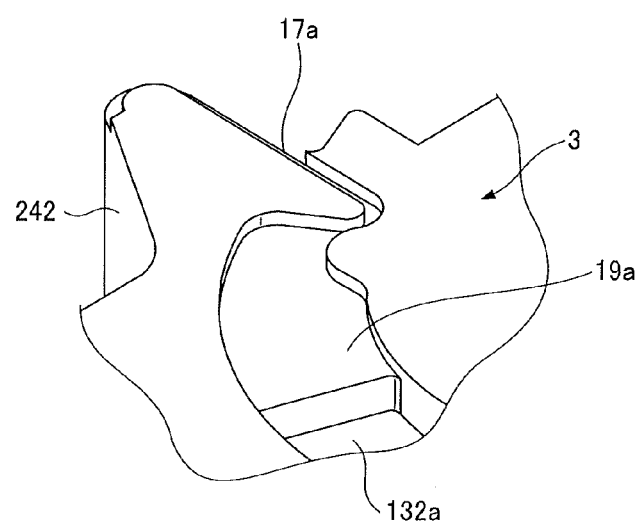
FIG. 106 is an enlarged perspective view of substantial parts of a base substrate of a comparative example of the twenty-first embodiment of the present invention.
Figure 107:
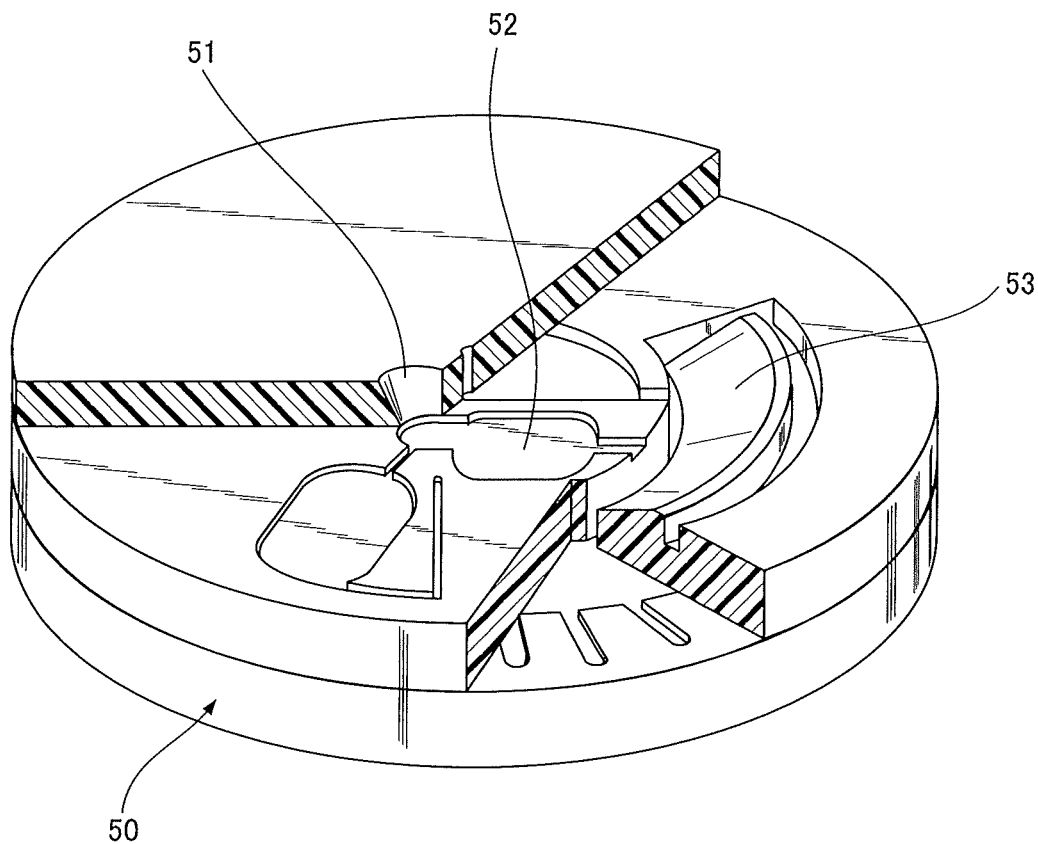
FIG. 107 is a partial cutaway perspective view of an analyzing device according to Patent Document 1.
Figure 108A:
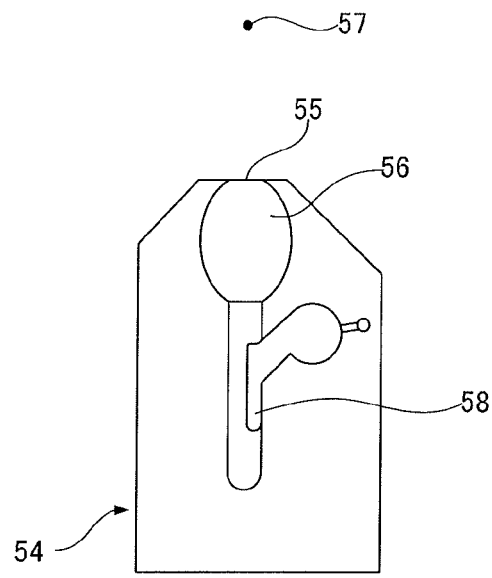
FIG. 108A is a plan view of an analyzing device according to Patent Document 2.
Figure 108B:
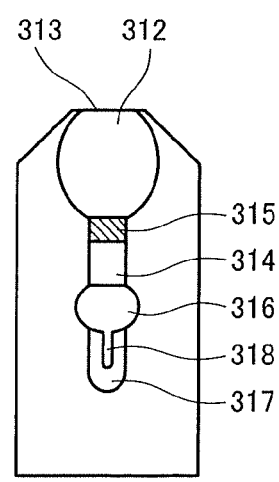
FIG. 108B is a plan view of another analyzing device according to Patent Document 2.
Figure 109:
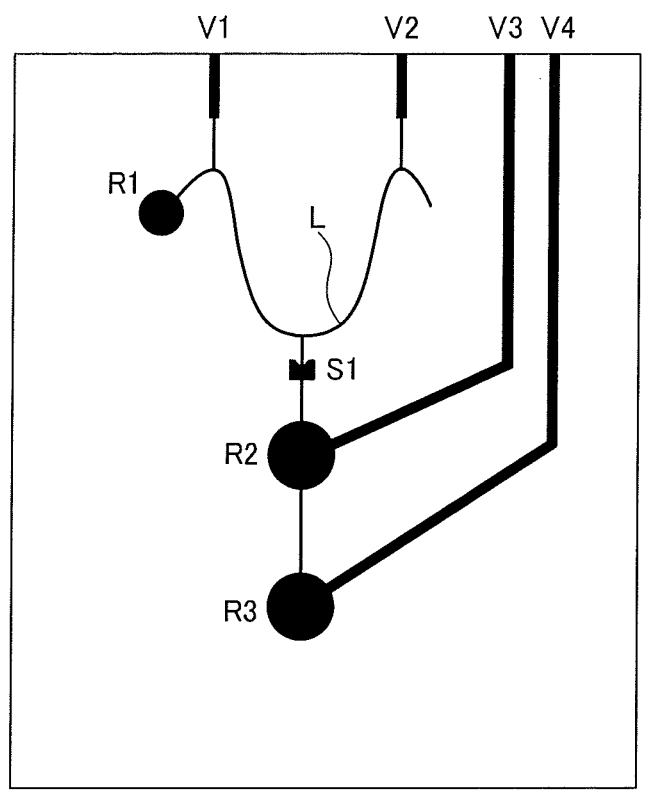
Figure 110:
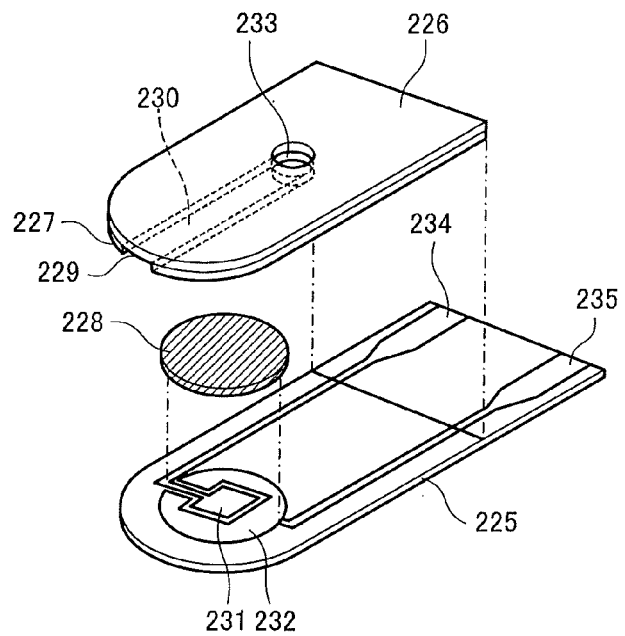
Figure 111:
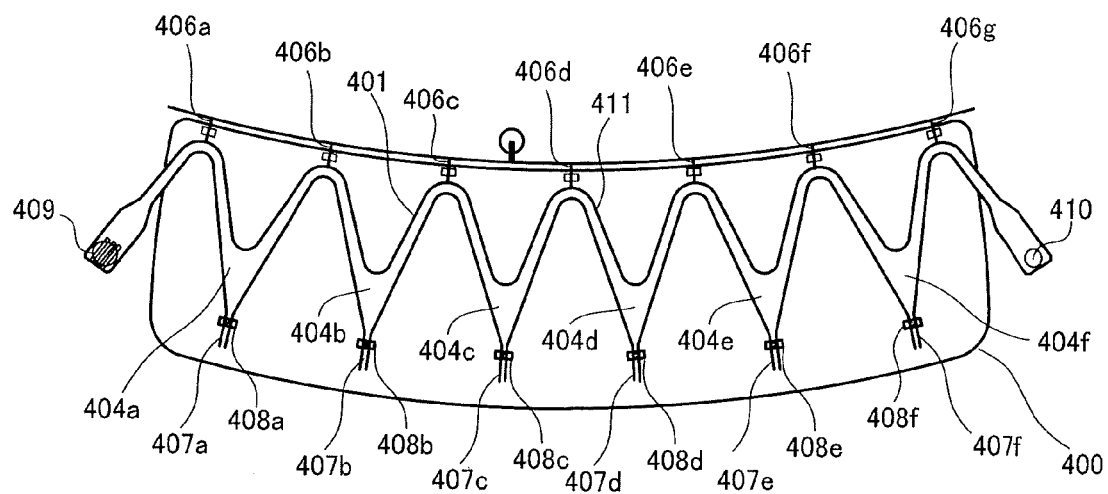

In the case of the comparative example illustrated in FIG. 106, it is difficult to visually confirm from the face 3*b* a state where suctioned blood has reached a fixed value.

While the protrusion 247 is provided on the side of the base substrate 3 and the gap is formed so as to be 0.1 mm in the present fifteenth embodiment, the protrusion 247 may alternatively be provided on the side of the cover substrate 4 and an 0.1 mm gap may be formed on a trailing end of the holding chamber 19*a*.

Sixteenth Embodiment

FIGS. 86 to 92 illustrate a sixteenth embodiment of the present invention.

Figure 86:
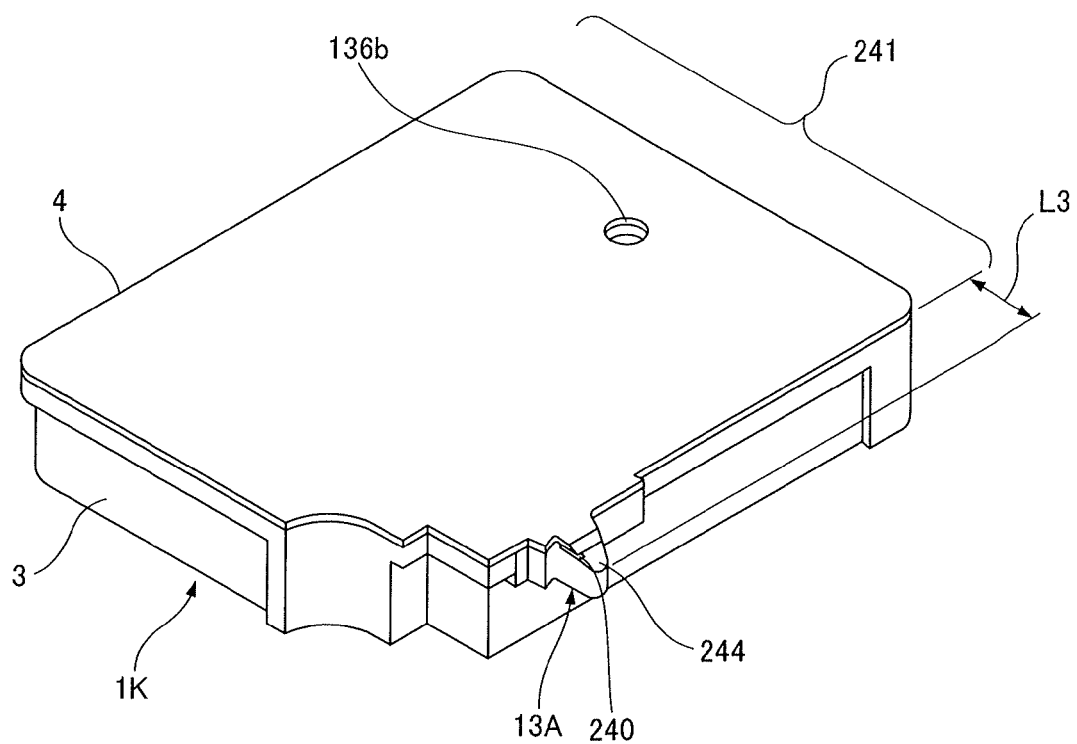
FIG. 86 is an external perspective view of an analyzing device according to the present invention (sixteenth embodiment)
Figure 87:
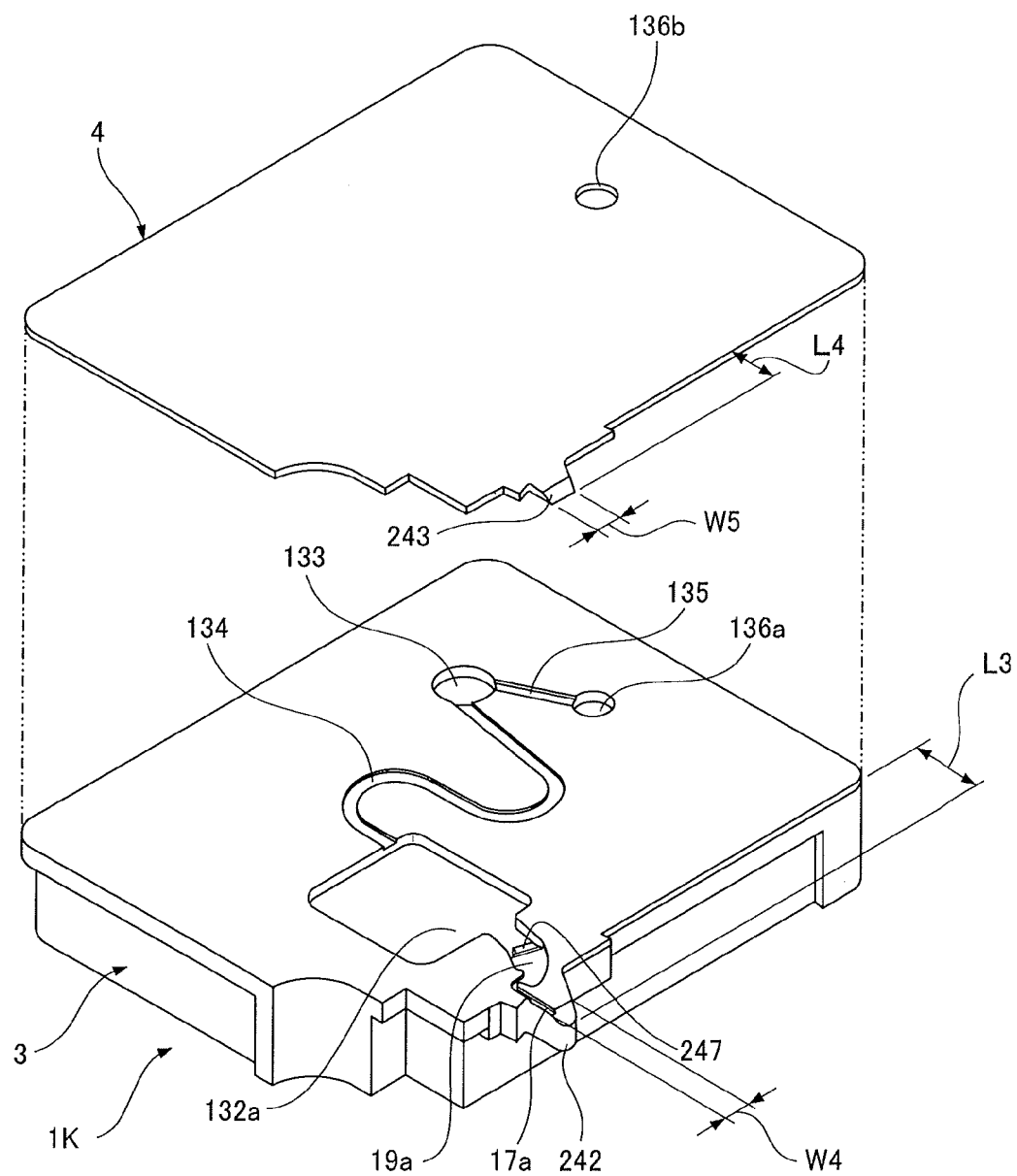
FIG. 87 is an exploded perspective view of an analyzing device according to the sixteenth embodiment of the present invention.

As illustrated in FIGS. 86 and 87, an analyzing device 1K constructed by bonding together a base substrate 3 and a cover substrate 4 differs from the fifteenth embodiment in that a leading end of a spot application section 13A is formed by an inclined face 244 and an end of a supplying capillary channel 17*a* opens on the inclined face 244.

Figure 88:
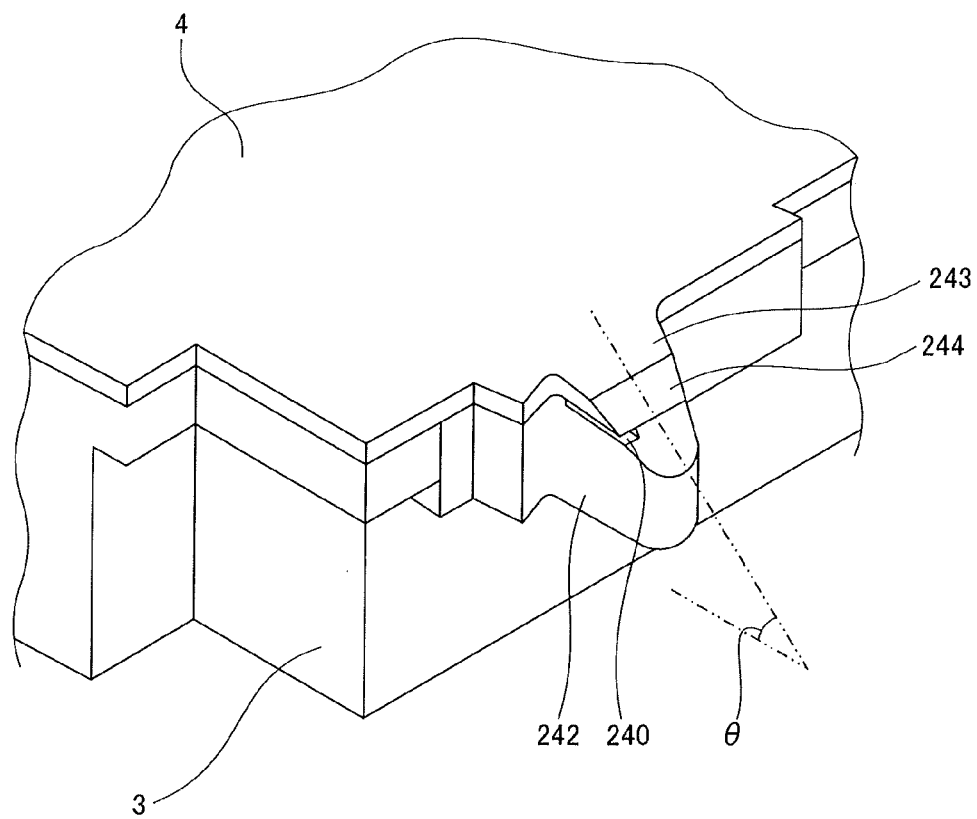
FIG. 88 is an enlarged perspective view of substantial parts according to the sixteenth embodiment of the present invention.
Figure 89:
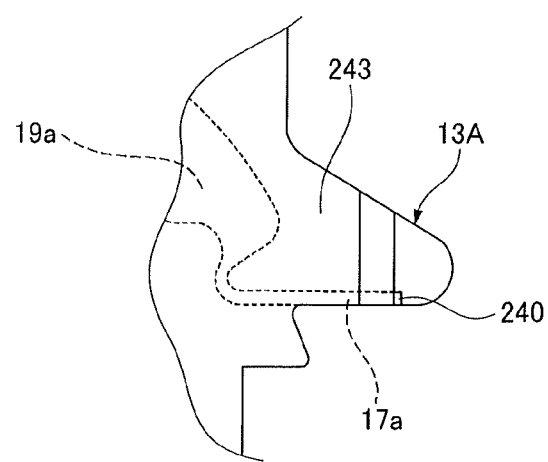
FIG. 89 is an enlarged plan view of substantial parts according to the sixteenth embodiment of the present invention.

Since the leading end of the spot application section 13A is formed on the inclined face 244, in the spot application section 13A formed by a bonding of a protrusion 242 of the base substrate 3 and a protrusion 243 of the cover substrate 4, a protrusion length L4 of the protrusion 243 is smaller than a protrusion length L3 of the protrusion 242. In addition, as illustrated in FIG. 88, an angle θ of the inclined face 244 is acute. Specifically, when blood is used as a sample liquid, the angle θ preferably ranges from 30 degrees to 45 degrees. A situation where an opening 240 that is an end of the supplying capillary channel 17*a* is opened on the inclined face 244 is illustrated in FIG. 89.

Moreover, a width W4 of the protrusion 242 of the base substrate 3 in a vicinity of the opening 240 and a width W5 of the protrusion 243 of the cover substrate 4 in a vicinity of the opening 240 are formed so as to equal each other.

The width W4 of the protrusion 242 of the base substrate 3 and the width W5 of the protrusion 243 of the cover substrate 4 are set so as to range from 3 to 5 mm, and a protrusion length L3 of the spot application section 13A from an analyzing device main body 241 is set to 8 mm.

Figure 90:
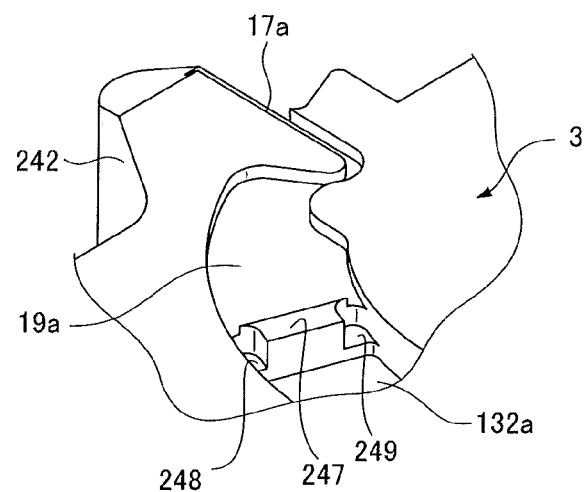
FIG. 90 is an enlarged perspective view of substantial parts of a base substrate according to the sixteenth embodiment of the present invention.

The spot application section 13A is formed by a bonding of the protrusion 242 of the base substrate 3 and the protrusion 243 of the cover substrate 4. Configurations of a filling confirmation region 246 on a trailing end of the holding chamber 19*a* and a confirmation window 253 are the same as the fifteenth embodiment, and as illustrated in FIGS. 90 and 92, a leading end of the spot application section 13A and the holding chamber 19*a* is connected by the supplying capillary channel 17*a* formed between the base substrate 3 and the cover substrate 4.

Figure 91:
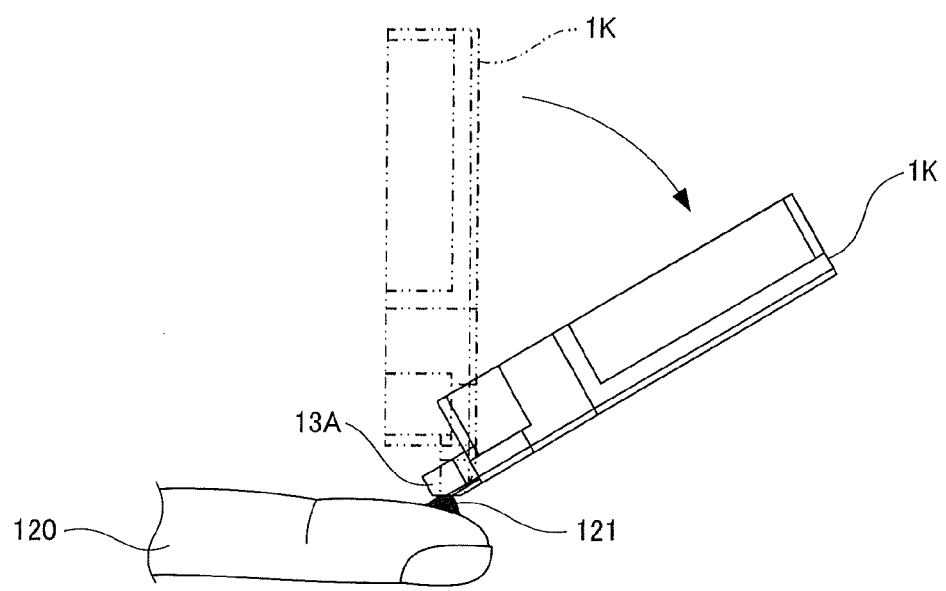
FIG. 91 is an explanatory diagram of an in-use state according to the sixteenth embodiment of the present invention.

Due to such a configuration, when performing an analysis of blood as a sample liquid, as is the case with the analyzing device 1K depicted by an imaginary line in FIG. 91, even if the analyzing device 1K is set to a vertical posture and a leading end of the spot application section 13A is brought into contact with a blood drop 121 on a fingertip 120 of a testee, since the opening 240 on one end of the supplying capillary channel 17*a* that is opened on the inclined face 244 does not come into contact with the blood drop 121, blood is not suctioned from the supplying capillary channel 17*a* to the holding chamber 19*a*.

Therefore, by inclining the analyzing device 1K as depicted by a solid line in FIG. 91 and bringing the inclined face 244 alongside the fingertip 120, the opening 240 that opens on the inclined face 244 comes into contact with the blood drop 121 and blood is suctioned from the supplying capillary channel 17*a* to the holding chamber 19*a*.

Figure 92:
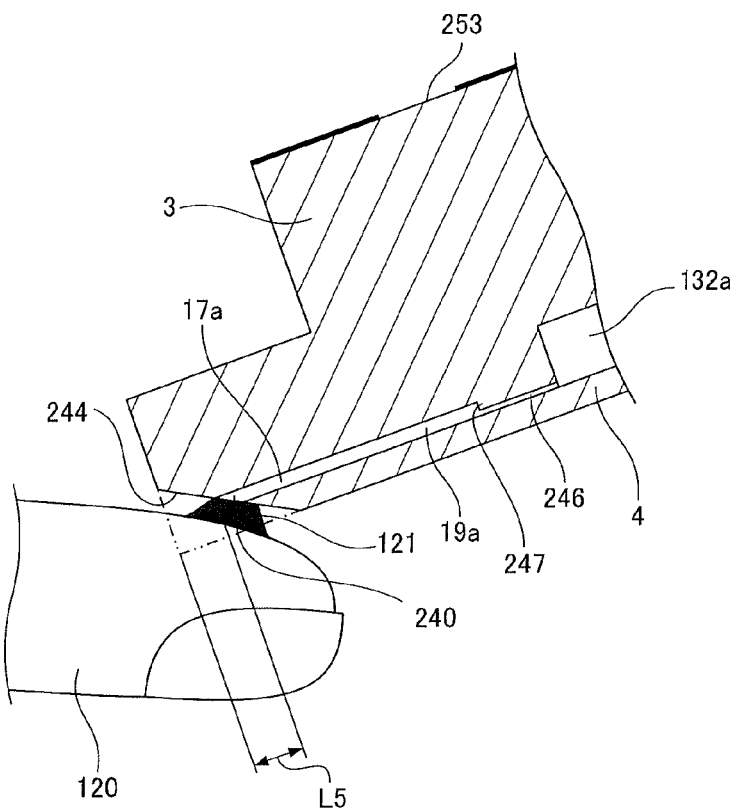
FIG. 92 is an enlarged cross-sectional view of substantial parts illustrated in FIG. 91.
Figure 105:
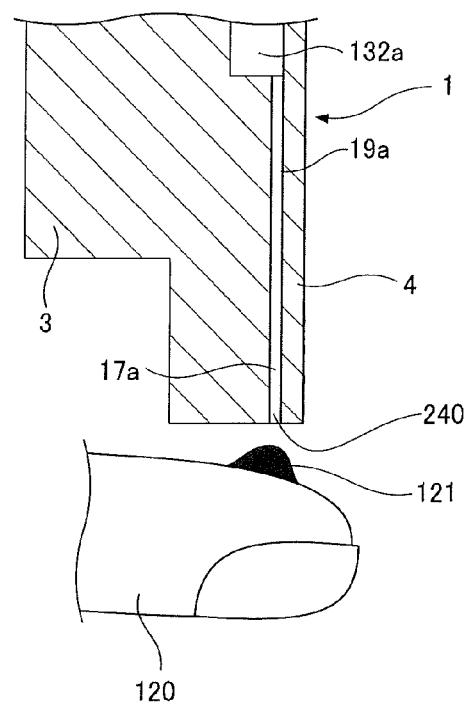
FIG. 105 is an enlarged cross-sectional view of an in-use state of a comparative example of the twenty-first embodiment of the present invention.

As shown, by forming the shape of the leading end of the spot application section 13A on the inclined, face 244, as illustrated in FIG. 92, the length of the supplying capillary channel 17*a* is reduced by a distance L5 in comparison to the comparative example illustrated in FIG. 77. In addition, since an angle formed by the supplying capillary channel 17*a* and the holding chamber 19*a* during suction is set so as to range from 30 degrees to 45 degrees which is the same as the angle θ of the inclined face 244, a magnitude of gravity affecting the speed of suctioned blood can be reduced and a period of time required to sample a fixed amount of blood into the holding chamber 19*a* can be shortened in comparison to a case such as the comparative example illustrated in FIG. 105 in which the angle formed by the supplying capillary channel 17*a* and the holding chamber 19*a* is a right angle.

Furthermore, when suctioned blood reaches a fixed amount, the suctioned blood reaches the filling confirmation region 246, thereby enabling the suctioned blood to be confirmed from the confirmation window 253. Therefore, an accurate analysis can be performed when blood held in the holding chamber 19*a* is transferred towards the measurement chamber 133 by a centrifugal force and a solution in the measurement chamber 133 is optically accessed and analyzed.

Seventeenth Embodiment

Figure 93:
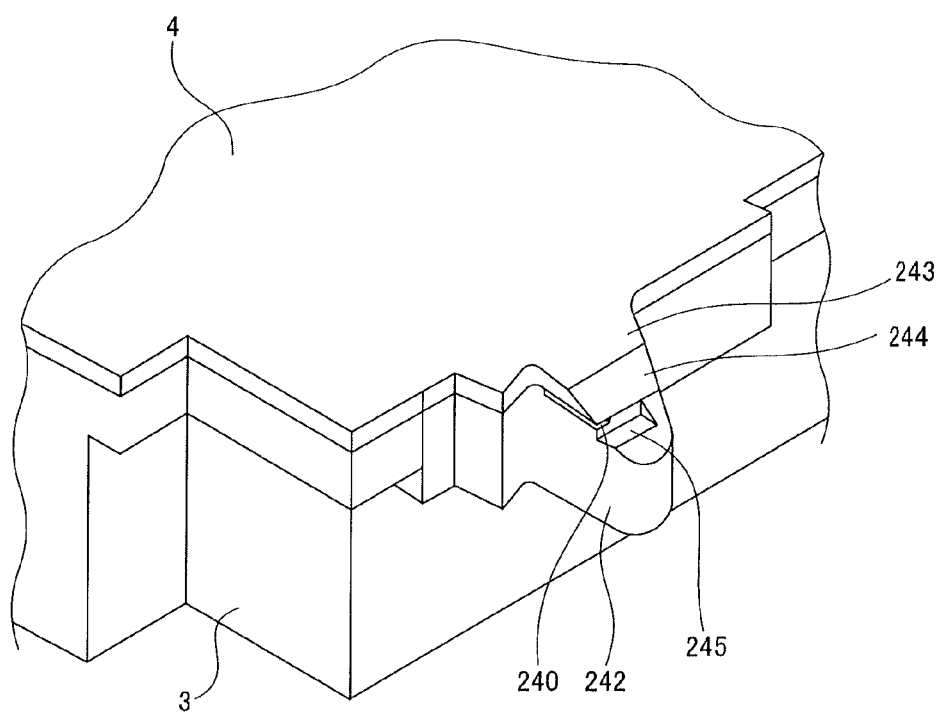
FIG. 93 is an enlarged perspective view of substantial parts according to the present invention (seventeenth embodiment)
Figure 94:
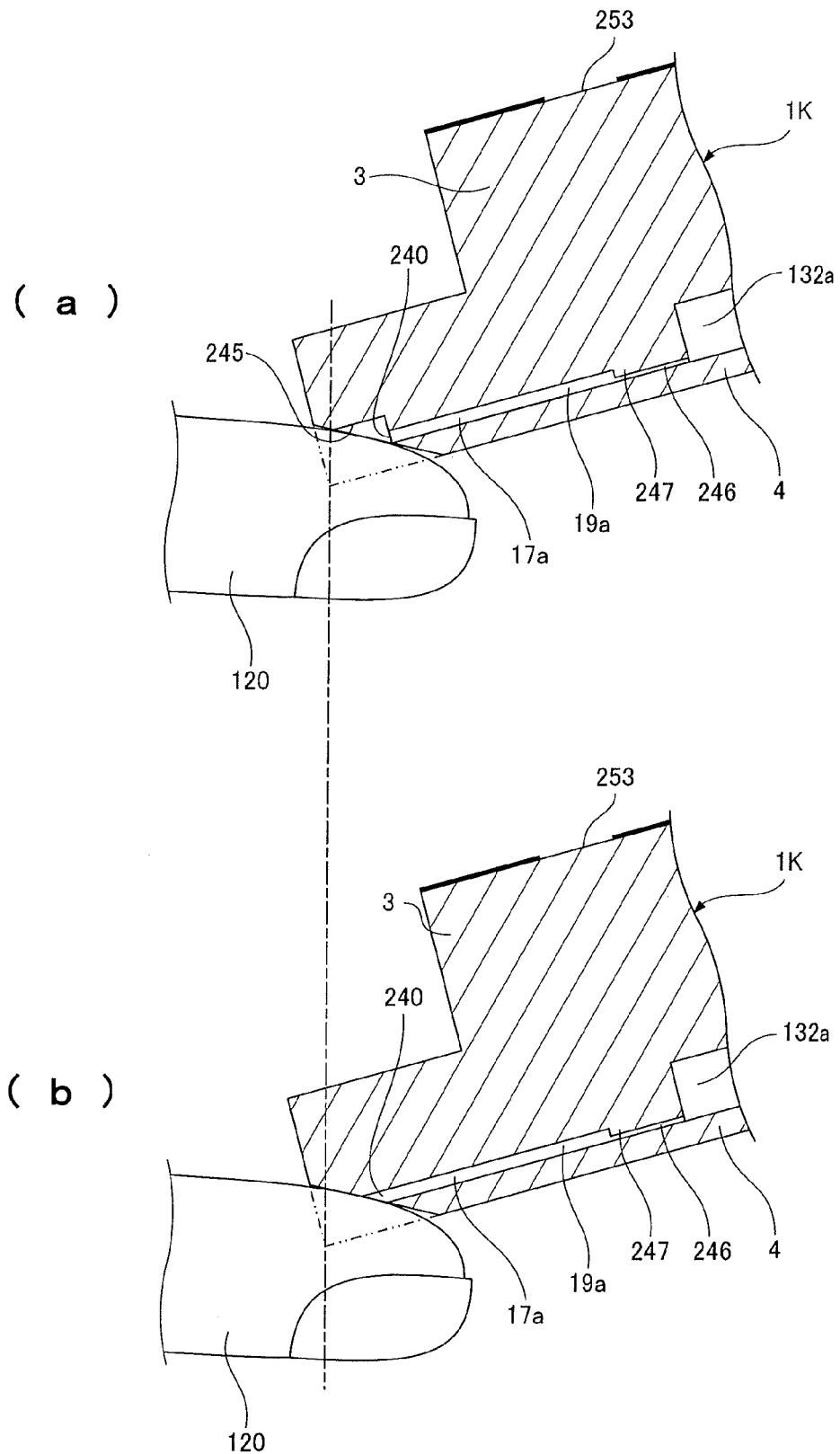
FIG. 94 is an enlarged cross-sectional view of an in-use state according to the seventeenth embodiment of the present invention and an enlarged cross-sectional view of an in-use state according to a comparative example.

FIGS. 93 and 94 illustrate a seventeenth embodiment of the present invention.

In the case of the sixteenth embodiment, it is conceivable that when the analyzing device 1K is excessively pressed against the fingertip 120 of a testee as illustrated in FIG. 94(*b*), the opening 240 opened on the inclined face 244 ends up being closed by the fingertip 120 and the suction speed of blood declines. In contrast, a seventeenth embodiment differs from the sixteenth embodiment in that, as illustrated in FIG. 93, a closure prevention recess 245 that communicates with an opening 240 is formed on the inclined face 244. Specifically, while a cover substrate 4 is the same as in the fifteenth embodiment, the closure prevention recess 245 is formed on a base substrate 3.

Configurations of a filling confirmation region 246 on a trailing end of a holding chamber 19*a* and the confirmation window 253 are the same as the fifteenth embodiment, and as illustrated in FIG. 94, a leading end of the spot application section 13A and the holding chamber 19*a* is connected by a supplying capillary channel 17*a* formed between the base substrate 3 and the cover substrate 4.

Due to such a configuration, even when the analyzing device 1K is excessively pressed against a fingertip 120 of a testee, as illustrated in FIG. 94(*a*), the closure prevention recess 245 acts to prevent the fingertip 120 from coming into contact with the opening 240. Therefore, even in this case, a decline in the suction speed of blood does not occur.

Eighteenth Embodiment

FIGS. 95 to 98 illustrate an eighteenth embodiment of the present invention.

In the sixteenth embodiment, since the inclined face 244 is formed at the spot application section 13A, an area wetted by blood when the inclined face 244 is brought into contact with the blood drop 121 increases in comparison to a comparative example illustrated in FIG. 75 and blood not suctioned by a capillary force into the supplying capillary channel 17a remains on the leading end of the base substrate 3 and solidifies. However, the present eighteenth embodiment is capable of reducing blood remaining on the leading end of the base substrate 3.

Figure 95:
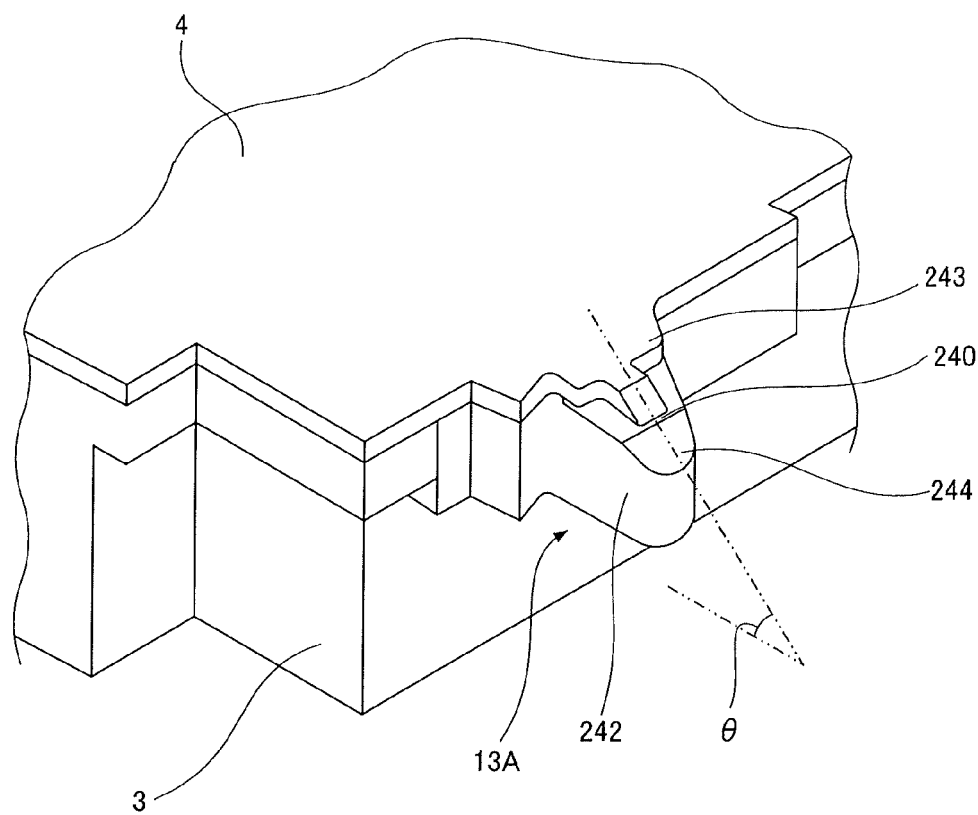
FIG. 95 is an enlarged perspective view of substantial parts according to the present invention (eighteenth embodiment)
Figure 96:
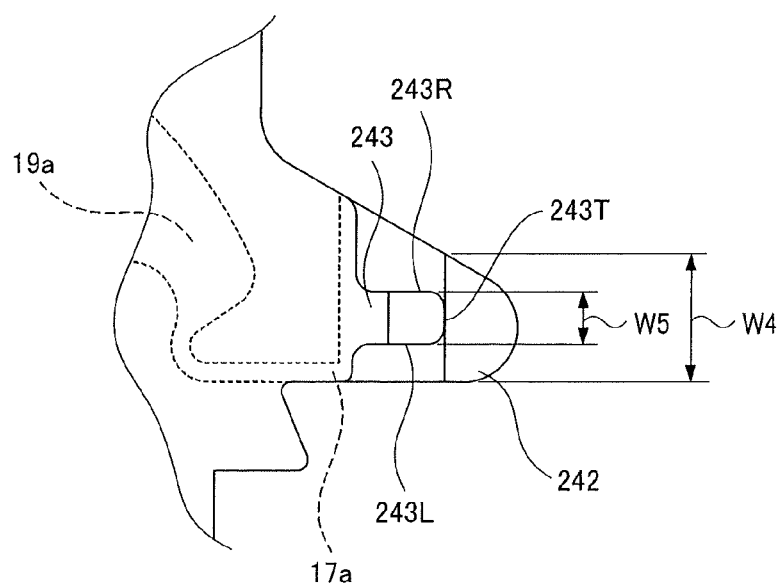
FIG. 96 is an enlarged plan view of substantial parts according to the eighteenth embodiment of the present invention.

In the sixteenth embodiment, the width W4 of the protrusion 242 of the base substrate 3 and the width W5 of the protrusion 243 of the cover substrate 4 are formed so as to equal each other. However, in the present seventeenth embodiment, while an incline of the inclined face 244 of the spot application section 13A is the same, a width W5 of a protrusion 243 of a cover substrate 4 in a vicinity of the opening 240 is formed narrower than a width W4 of a protrusion 242 of a base substrate 3. In FIG. 95, a leading end of the protrusion 243 of the cover substrate 4 is positioned in a vicinity of the center of the protrusion 242 of the base substrate 3. As illustrated in FIG. 96, the one end of the supplying capillary channel 17a is opened on both sides 243R and 243L of the protrusion 243 and at a leading end 243T of the protrusion 243.

Figure 97:
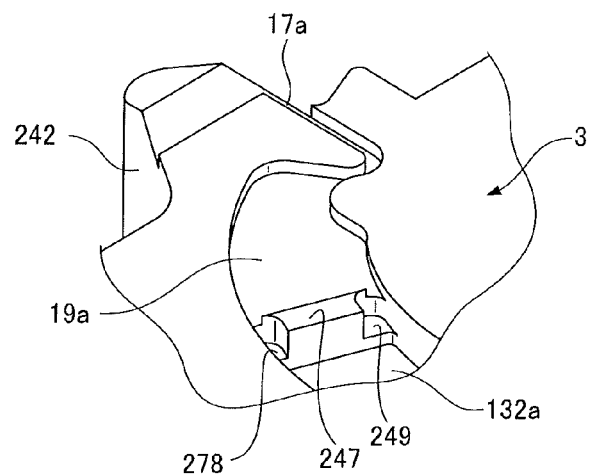
FIG. 97 is an enlarged perspective view of substantial parts of a base substrate according to the eighteenth embodiment of the present invention.
Figure 98:
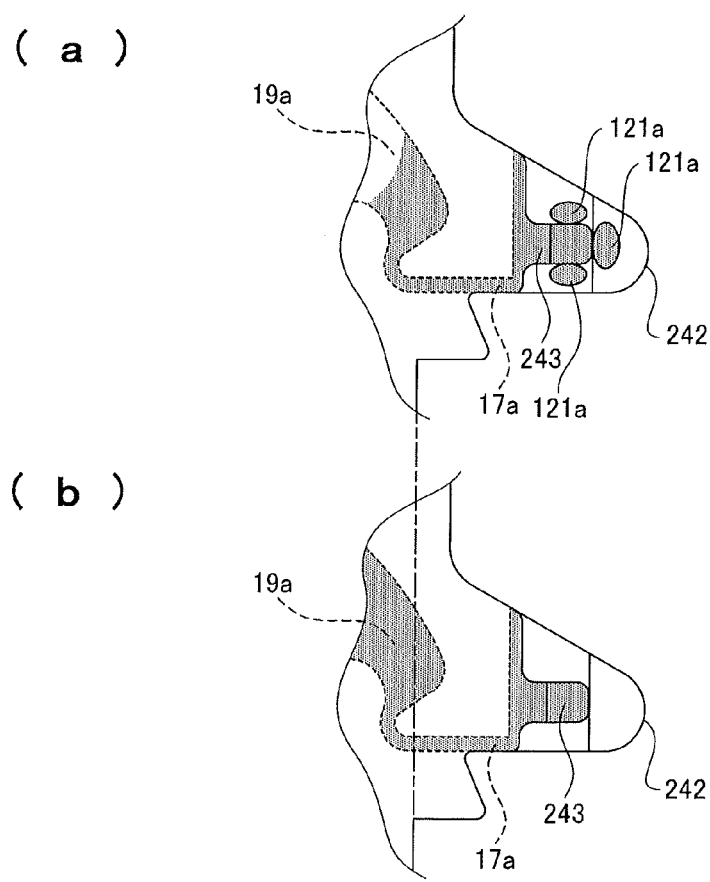
FIG. 98 is a plan view of an in-use state according to the eighteenth embodiment of the present invention.

Configurations of a filling confirmation region 246 on a trailing end of a holding chamber 19a and the confirmation window 253 are the same as the fifteenth embodiment, and as illustrated in FIG. 97, a leading end of the spot application section 13A and the holding chamber 19a is connected by the supplying capillary channel 17a formed between the base substrate 3 and the cover substrate 4.

Due to such a configuration, blood is first suctioned by a capillary force into a holding chamber 19a via a supplying capillary channel 17a as illustrated in FIG. 98(a), and a major portion of blood 121a remaining in a portion of the inclined face 244 in the protrusion 242 of the base substrate 3 can be suctioned by a capillary force as illustrated in FIG. 98(b) via the supplying capillary channel 17a formed between a leading end of the protrusion 243 of the cover substrate 4 whose leading end is narrower than the protrusion 242 of the base substrate 3 and the protrusion 242 of the base substrate 3.

In the respective embodiments described above, the more acute the incline of the spot application section, the more the analyzing device 1K can be inclined horizontally, which is effective in reducing filling time. While an incline of the spot application section 13A ranging from 30 to 45 degrees has been confirmed as being effective when blood is used as a sample liquid, the angle is not restricted thereto if an angle of 45 degrees or greater is effective in regards to filling time depending on the sample liquid.

Nineteenth Embodiment

FIGS. 99 to 102 illustrate a nineteenth embodiment of the present invention.

Figure 99:
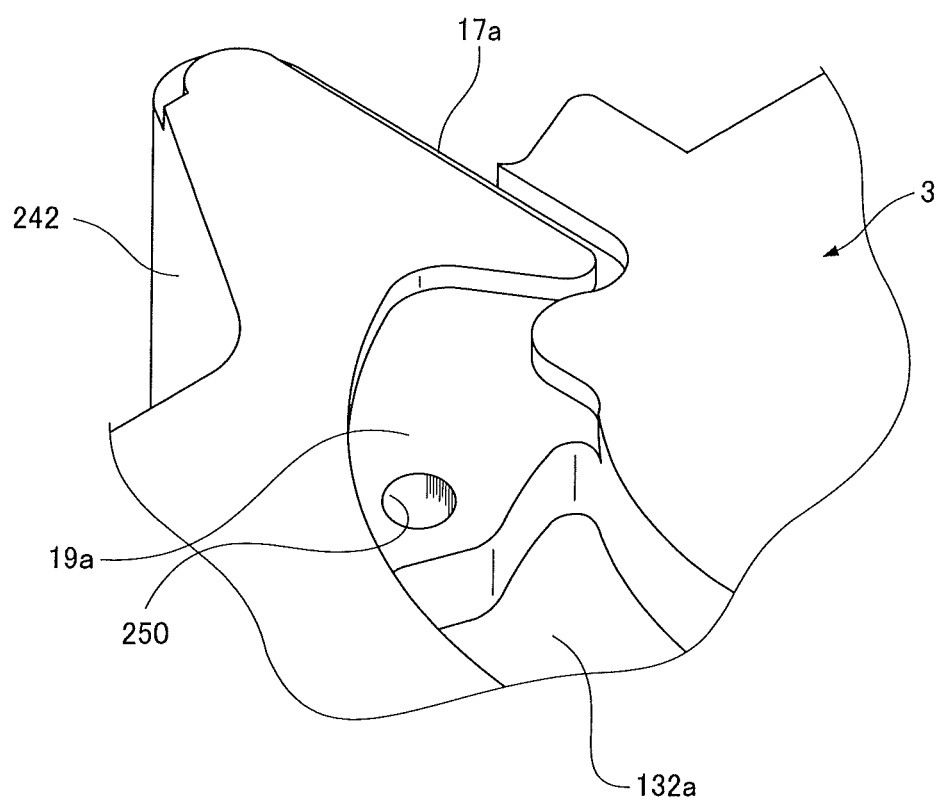
FIG. 99 is an enlarged perspective view of substantial parts of a base substrate according to the present invention (nineteenth embodiment)
Figure 100:
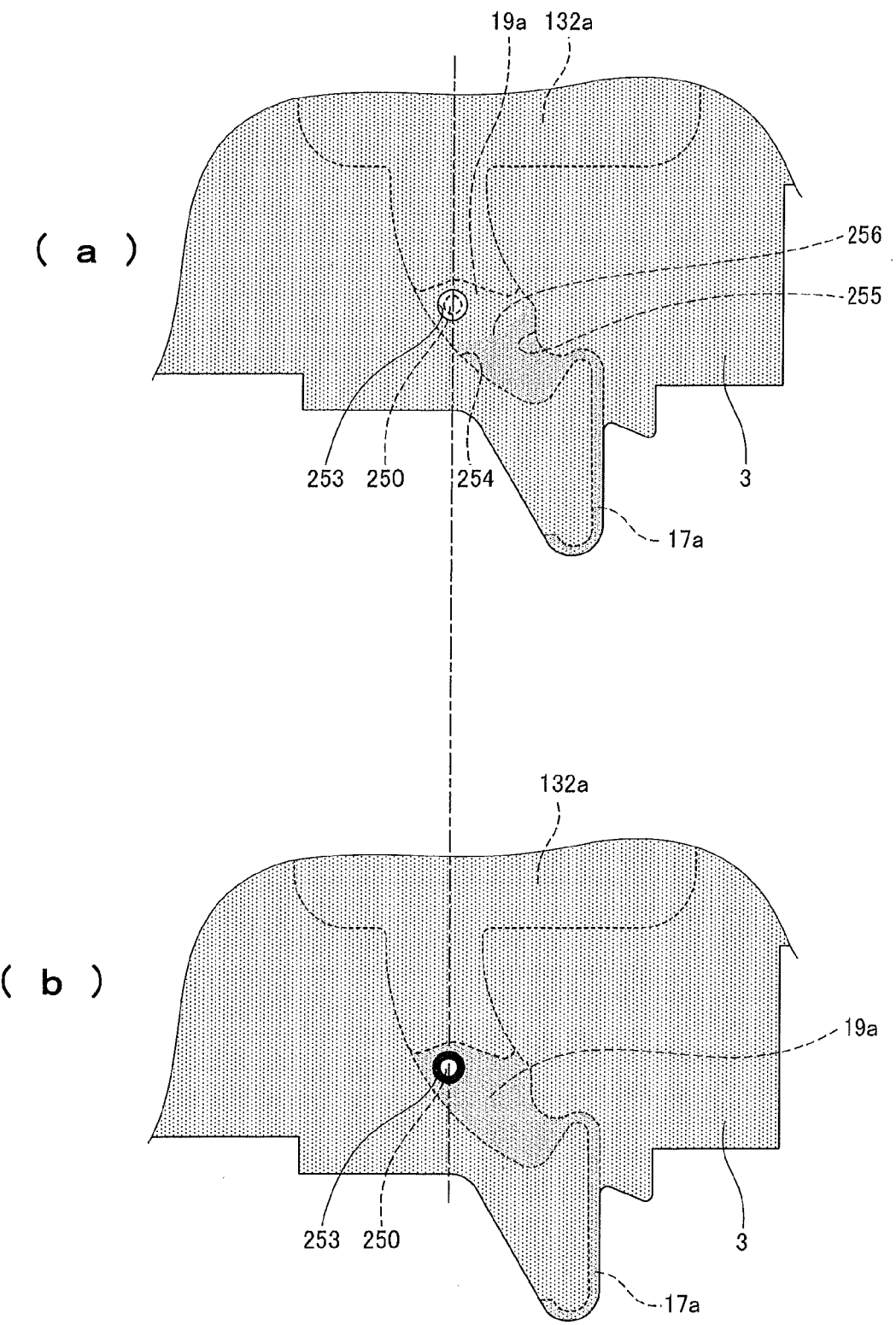
FIG. 100 is an explanatory diagram of an in-use state according to the nineteenth embodiment of the present invention.
Figure 101:
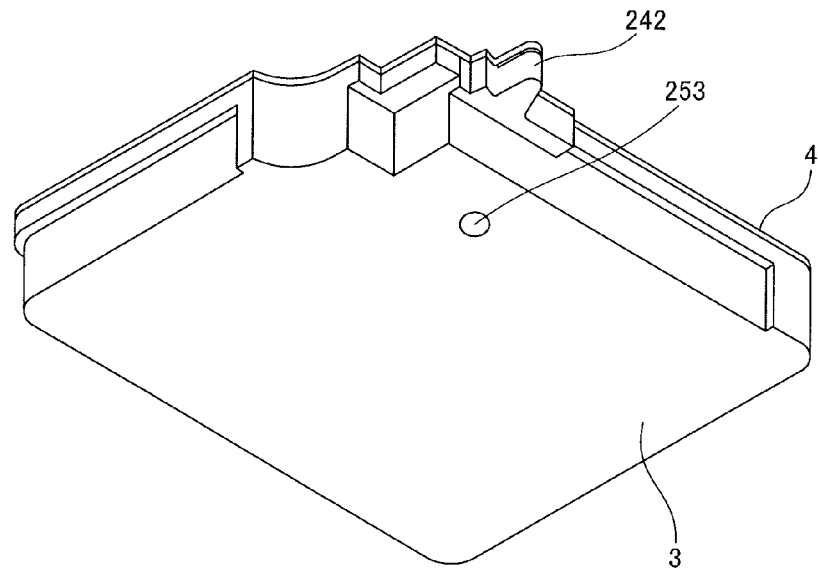
FIG. 101 is an external perspective view of an analyzing device according to the nineteenth embodiment of the present invention.
Figure 102:
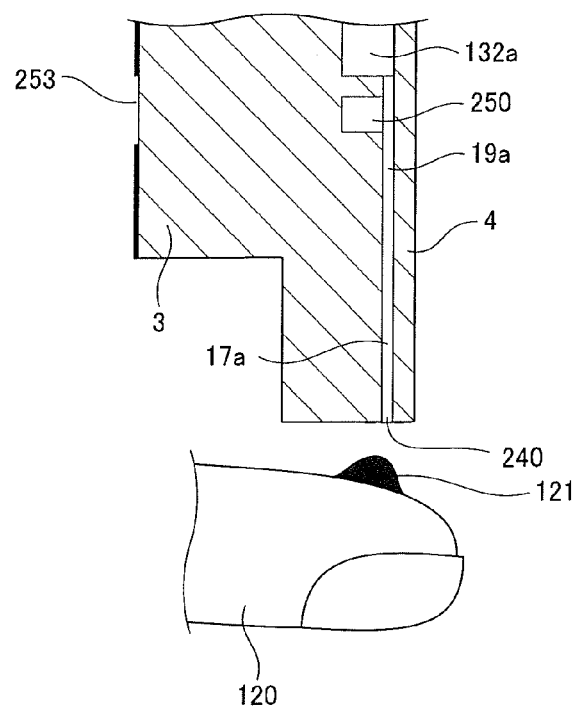
FIG. 102 is an enlarged cross-sectional view of an in-use state according to the nineteenth embodiment of the present invention.

In the fifteenth embodiment, the protrusion 247 that forms the filling confirmation region 246 having a smaller gap (0.1 mm) than the capillary force-generating gap (0.3 mm) of the holding chamber 19a is formed on a trailing end of the holding chamber 19a. However, the present nineteenth embodiment differs from the fifteenth embodiment in that, as illustrated in FIGS. 99 and 102, a recess 250 forming a filling confirmation region 246 having a greater gap than the capillary force-generating gap (0.3 mm) of the holding chamber 19a is formed on a trailing end of a holding chamber 19a.

Due to such a configuration, as illustrated in FIG. 100(a), blood 121a as a sample initially flows along wall faces 254 and 255 of the holding chamber 19a and is suctioned in a shape in which a central part 256 lags behind sides of the wall faces 254 and 255. In such a state where suction is in progress, suctioned blood cannot be confirmed through the confirmation window 253 illustrated in FIG. 101.

Once the suctioned blood reaches a fixed amount, as illustrated in FIG. 100(b), the suctioned blood reaches the filling confirmation region 246, thereby enabling the suctioned blood to be confirmed through the confirmation window 253.

Moreover, while the nineteenth embodiment is an embodiment in which the filling confirmation region 246 formed as the protrusion 247 in the fifteenth embodiment is now formed as the recess 250, the nineteenth embodiment may alternatively be implemented by forming the filling confirmation region 246 formed as the protrusion 247 in the sixteenth, seventeenth, and eighteenth embodiments as the recess 250.

Twentieth Embodiment

Figure 103:
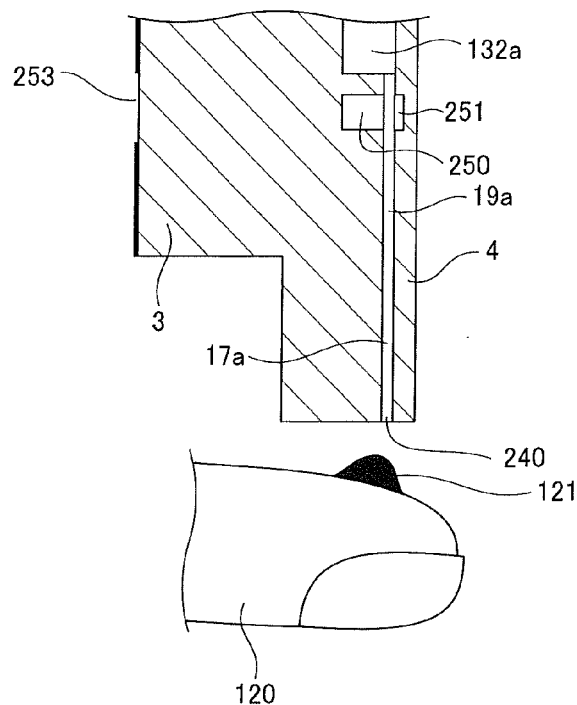
FIG. 103 is an enlarged cross-sectional view of an in-use state according to the present invention (twentieth embodiment)

FIG. 103 illustrates a twentieth embodiment of the present invention.

In the nineteenth embodiment, the gap provided on the trailing end of a holding chamber 19a and which is greater than the capillary force-generating gap of the holding chamber 19a is formed between the bottom of the recess 250 that penetrates on a side of the base substrate 3 towards an opposite side to the cover substrate 4 and the cover substrate 4. However, the present twentieth embodiment differs from the nineteenth embodiment in that a recess 251 is formed on the cover substrate 4 so as to correspond to a recess 250 formed on a side of a base substrate 3.

As illustrated in FIG. 102 according to the nineteenth embodiment, when a face of the cover substrate 4 corresponding to the recess 250 provided on a side of the base substrate 3 is flat, blood that is a sample liquid may penetrate into the recess 250 if a diameter of the recess 250 is small. In this case, a fixed amount display viewed from a confirmation window 253 may be blurry.

In contrast, by forming the recess 251 on the cover substrate 4 as is the case with the twentieth embodiment, occurrences of situations where blood that is a sample liquid flows along a face of the cover substrate 4 and penetrates into the recess 250 can be avoided even when a diameter of the recess 250 is small. As a result, a fixed amount display viewed from a confirmation window 253 can be clarified.

Twenty-First Embodiment

Figure 104:
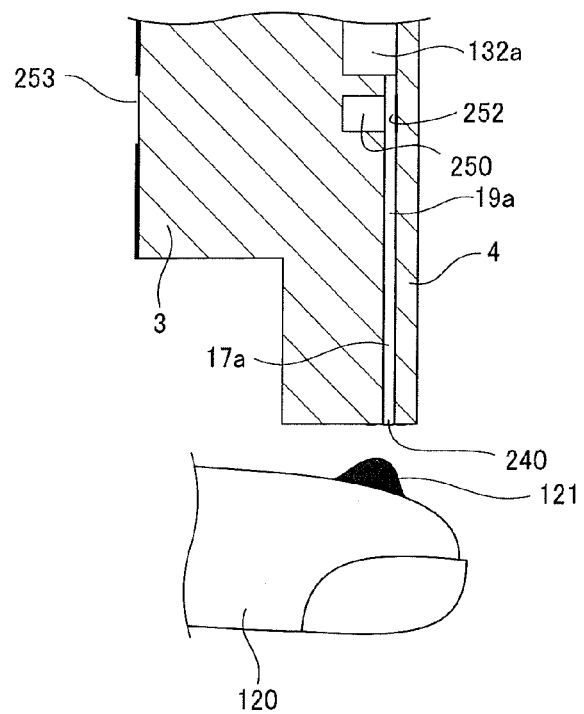
FIG. 104 is an enlarged cross-sectional view of an in-use state according to the present invention (twenty-first embodiment)

FIG. 104 illustrates a twenty-first embodiment of the present invention.

In the twentieth embodiment illustrated in FIG. 103, the recess 251 is formed on the cover substrate 4 in correspondence to the recess 250 formed on the side of the base substrate 3 in order to prevent blood as a sample liquid from flowing along the cover substrate 4 and penetrating into the recess 250. However, in FIG. 104, a hydrophobically treated section 252 is provided on a surface of the cover substrate 4 in correspondence to the recess 250 formed on the side of the base substrate 3 while the recess 251 shown in the twentieth embodiment is not provided. Specifically, when the base substrate 3 and the cover substrate 4 are molded from a transparent synthetic resin such as acrylic resin, the hydrophobically treated section 252 is realized by a method such as coating a surface of the cover substrate 4 which is flat with biodegradable hydrophobic polyester processed by high temperature and pressure water.

Even in this case, a fixed amount display viewed from a confirmation window 253 can be clarified in the same manner as in the twentieth embodiment.

In the respective embodiments described above, the confirmation window 253 is provided on a side of the base substrate 3. Alternatively, the respective embodiments described above may be arranged such that the confirmation window 253 is provided on a side of the cover substrate 4 in correspondence to the filling confirmation region 246.

While the case of an analyzing device to be used for reading involving optically accessing a solution in the measurement chamber 133 has been described as an example in the respective embodiments described above, an analyzing device to be used for reading involving accessing a solution in the measurement chamber 133 provided with an electrochemical sensor can be similarly implemented.

In addition, while the case where blood suctioned by a capillary force into the holding chamber 19a is transferred by a centrifugal force to the measurement chamber 133 has been described as an example in the fifteenth to twenty-first embodiments, even in a case of an analyzing device to be used for reading involving directly suctioning a sample liquid from the opening 240 into a measurement chamber having a capillary force and accessing a test object in the measurement chamber, the fixed amount of blood can be sampled and an accurate analysis can be realized by enabling blood suctioned into the holding chamber 19a to be confirmed from the confirmation window 253 as described in the fifteenth to twenty-first embodiments.

INDUSTRIAL APPLICABILITY

The present invention is useful as, for example, a transfer control unit of an analyzing device to be used for component analysis of a liquid collected from a living organism or the like.

The invention claimed is:

1. An analyzing device having a microchannel structure, the analyzing device comprising:
   an axial center around which the microchannel structure is rotationally driven;
   a sample inlet;
   a guide section, in which a capillary force acts, extending from the sample inlet toward the axial center, the guide section having a first end and a second end with the second end connected to the sample inlet, the first end is positioned closer to the axial center than the second end;
   a first cavity, in which a capillary force acts, configured to measure a certain amount of sample liquid;
   a bent section, in which a capillary force acts, connecting the first end of the guide section to the first cavity;
   a receiving cavity, in which a capillary force does not act, located adjacent to the first cavity and configured to receive a sample liquid from the first cavity; and
   a second cavity connected to the receiving cavity and extending along a side of the guide section and a side of the first cavity, the second cavity being directly opened to air,
   wherein a sample liquid is transferred from the sample inlet to the receiving cavity in a continuous flow pathway by a centrifugal force caused by rotating the analyzing device about the axial center, the flow pathway is a capillary pathway with a constant depth from the guide section to the first cavity, the bent section being configured to change a direction of the flow pathway from a direction extending toward the axial center to a direction extending away from the axial center.

2. The analyzing device according to claim 1, wherein when the analyzing device is rotated about the axial center, a sample liquid retained in the guide section and the first cavity is divided at the position of the bent section by action of a centrifugal force, thereby allowing the sample liquid retained in the first cavity to be transferred to the receiving cavity, and the sample liquid retained in the guide section to be scattered toward the sample inlet.

3. The analyzing device according to claim 1, wherein a wall of the first cavity has a recessed portion recessed away from the axial center, the bent section being formed closer to the axial center than the recessed portion of the wall of the first cavity.

4. The analyzing device according to claim 2, further comprising:
   a protective cap configured to hold a sample liquid scattered from the sample inlet.

5. The analyzing device according to claim 1, further comprising an internal measurement spot where a sample component after treatment in the receiving cavity is transferred for measurement.

6. An analyzing apparatus, comprising:
   the analyzing device according to claim 5;
   a rotation driving unit that rotates the analyzing device around the axial center; and
   an analysis unit configured to access and analyze a reactant inside the analyzing device based on a solution transferred by the rotation driving unit,
   wherein a sample liquid in the first cavity is transferred to the receiving cavity by a rotation of the rotation driving unit.

7. An analyzing method comprising rotating the analyzing device of claim 1 around the axial center.

8. An analyzing method, comprising:
   spot applying a sample liquid to a sample inlet of the analyzing device of claim 1; and
   rotating the analyzing device about the axial center, thereby:
      transferring the sample liquid from the sample inlet to the receiving cavity by a centrifugal force caused by rotation of the analyzing device, and
      allowing the sample liquid to pass through the continuous capillary flow pathway.

* * * * *